(12) United States Patent
Li et al.

(10) Patent No.: US 8,735,553 B1
(45) Date of Patent: May 27, 2014

(54) ANTI-PD1 ANTIBODIES AND THEIR USE AS THERAPEUTICS AND DIAGNOSTICS

(71) Applicant: BeiGene, Ltd., Grand Cayman (KY)

(72) Inventors: Kang Li, Beijing (CN); Tong Zhang, Beijing (CN); Jing Song, Beijing (CN); Lanlan Xu, Beijing (CN); Qi Liu, Beijing (CN); Hao Peng, Beijing (CN)

(73) Assignee: Beigene, Ltd., George Town (KY)

( * ) Notice: Subject to any disclaimer, the term of this patent is extended or adjusted under 35 U.S.C. 154(b) by 0 days.

(21) Appl. No.: 14/076,214

(22) Filed: Nov. 10, 2013

Related U.S. Application Data

(63) Continuation of application No. PCT/CN2013/083467, filed on Sep. 13, 2013.

(51) Int. Cl.
  *C07K 16/28* (2006.01)
  *A61K 39/395* (2006.01)
(52) U.S. Cl.
  USPC .............. 530/388.22; 530/388.75; 424/144.1; 424/154.1
(58) Field of Classification Search
  CPC ........... C07K 16/2818; C07K 16/2896; C07K 2316/96; C07K 2317/565; C07K 2317/56; C07K 2316/52; C07K 2317/71; C07K 2317/76
  See application file for complete search history.

(56) References Cited

U.S. PATENT DOCUMENTS

| | | | | |
|---|---|---|---|---|
| 6,632,927 | B2 * | 10/2003 | Adair et al. | 530/387.3 |
| 2004/0038339 | A1 * | 2/2004 | Kufer et al. | 435/69.1 |
| 2012/0076726 | A1 * | 3/2012 | Gellerfors et al. | 424/1.49 |

OTHER PUBLICATIONS

Rudikoff et al. 1982, Proc. Natl. Acad. Sci. USA, 79: 1979-1983.*
Panka et al., 1988, Proc. Natl. Acad. Sci. USA, 85: 3080-3084.*
Sequence Alignment, 2014, 1 page.*

* cited by examiner

*Primary Examiner* — Ilia Ouspenski
(74) *Attorney, Agent, or Firm* — Richard Aron Osman

(57) ABSTRACT

Provided are antibodies that specifically bind to Programmed Death-1 (PD1, Pdcd-1, or CD279) and inhibit PD1-mediated cellular signaling and activities in immune cells, antibodies binding to a set of amino acid residues required for its ligand binding, and uses of these antibodies to treat or diagnose cancer, infectious diseases or other pathological disorders modulated by PD1-mediated functions.

35 Claims, 7 Drawing Sheets

(B)

SEQUENCE LISTING

<160> NUMBER OF SEQ ID NOS: 90

<210> SEQ ID NO 1
<211> LENGTH: 444
<212> TYPE: DNA
<213> ORGANISM: Homo sapiens

<400> SEQUENCE: 1
ccaggatggt tcttagactc cccagacagg ccctggaacc cccccacctt ctccccagcc     60
ctgctcgtgg tgaccgaagg ggacaacgcc accttcacct gcagcttctc caacacatcg    120
gagagcttcg tgctaaactg gtaccgcatg agccccagca accagacgga caagctggcc    180
gccttccccg aggaccgcag ccagcccggc caggactgcc gcttccgtgt cacacaactg    240
cccaacgggc gtgacttcca catgagcgtg gtcagggccc ggcgcaatga cagcggcacc    300
tacctctgtg gggccatctc cctggccccc aaggcgcaga tcaaagagag cctgcgggca    360
gagctcaggg tgacagagag aagggcagaa gtgcccacag cccaccccag ccctcacccc    420
aggccagccg gccagttcca aacc                                            444

<210> SEQ ID NO 2
<211> LENGTH: 148
<212> TYPE: PRT
<213> ORGANISM: Homo sapiens

<400> SEQUENCE: 2

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr
145

<210> SEQ ID NO 3
<211> LENGTH: 354
<212> TYPE: DNA
<213> ORGANISM: Mus musculus

<400> SEQUENCE: 3
caggtgcagc tgaaggagtc aggacctggc ctggtggcgc cctcaaagaa cctgtccatc     60
acttgcactg tctctgggtt ttcattaacc agctatggtg tacactggat tcgccagcct    120
ccaggaaagg gactggaatg gctgggagta atatgggccg gtggaagcac aaattataat    180

```
tcggctctca tgtccagact gagcatcagc aaagacaact ccaggagcca agttttctta      240
agaatgaaca gtctgcaaac tgatgacaca gccatgtact actgtgccag agcctatggt      300
aactactggt acatcgatgt ctggggcgca gggaccacgg tcaccgtctc ctca            354
```

<210> SEQ ID NO 4
<211> LENGTH: 118
<212> TYPE: PRT
<213> ORGANISM: Mus musculus

<400> SEQUENCE: 4

```
Gln Val Gln Leu Lys Glu Ser Gly Pro Gly Leu Val Ala Pro Ser Lys
1               5                   10                  15

Asn Leu Ser Ile Thr Cys Thr Val Ser Gly Phe Ser Leu Thr Ser Tyr
            20                  25                  30

Gly Val His Trp Ile Arg Gln Pro Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Ser Ile Ser Lys Asp Asn Ser Arg Ser Gln Val Phe Leu
65                  70                  75                  80

Arg Met Asn Ser Leu Gln Thr Asp Asp Thr Ala Met Tyr Tyr Cys Ala
                85                  90                  95

Arg Ala Tyr Gly Asn Tyr Trp Tyr Ile Asp Val Trp Gly Ala Gly Thr
            100                 105                 110

Thr Val Thr Val Ser Ser
        115
```

<210> SEQ ID NO 5
<211> LENGTH: 321
<212> TYPE: DNA
<213> ORGANISM: Mus musculus

<400> SEQUENCE: 5

```
gacattgtga tgacccagac tcccaaattc ctgcttgtat cagcaggaga cagggttacc      60
ataacctgca aggccagtca gagtgtgagt aatgatgtag cttggtacca acagaagcca      120
gggcagtctc ctaaactgct gataaactat gcatttcatc gcttcactgg agtccctgat      180
cgtttcactg gcagtggata tgggacggat ttcattttca ccatcagcac tgtgcaggct      240
gaagacctgg cagtttattt ctgtcaccag gcttatagtt ctccgtacac gttcggaggg      300
gggaccaagc tggaaatgaa a                                                321
```

<210> SEQ ID NO 6
<211> LENGTH: 107
<212> TYPE: PRT
<213> ORGANISM: Mus musculus

<400> SEQUENCE: 6

```
Asp Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Asn Tyr Ala Phe His Arg Phe Thr Gly Val Pro Asp Arg Phe Thr Gly
    50                  55                  60

Ser Gly Tyr Gly Thr Asp Phe Ile Phe Thr Ile Ser Thr Val Gln Ala
65                  70                  75                  80
```

Glu Asp Leu Ala Val Tyr Phe Cys His Gln Ala Tyr Ser Ser Pro Tyr
                85                  90                  95

Thr Phe Gly Gly Gly Thr Lys Leu Glu Met Lys
                100                 105

<210> SEQ ID NO 7
<211> LENGTH: 342
<212> TYPE: DNA
<213> ORGANISM: Mus musculus

<400> SEQUENCE: 7
cagatccagt tggtgcagtc tggacctgag ctgaagaagc tggagagac agtcaagatc        60 tcctgcaagg cttctgggta taccttcaca aactatggaa tgaactgggt gaagcaggct     120
ccaggaaagg gtttaaagtg gatgggctgg ataaacaata ataatggaga gccaacatat     180
gctgaagagt tcaagggacg gtttgccttc tctttggaaa cctctgccag cactgcctat     240
ttgcagatca caaacctcaa aaatgaggac acggctacat atttctgtgc aagagatgtt     300
atggactatt ggggtcaagg aacctcagtc accgtctcct ca                        342

<210> SEQ ID NO 8
<211> LENGTH: 114
<212> TYPE: PRT
<213> ORGANISM: Mus musculus

<400> SEQUENCE: 8

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Asn Asn Asn Gly Glu Pro Thr Tyr Ala Glu Glu Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Asp Val Met Asp Tyr Trp Gly Gln Gly Thr Ser Val Thr Val
            100                 105                 110

Ser Ser

<210> SEQ ID NO 9
<211> LENGTH: 330
<212> TYPE: DNA
<213> ORGANISM: Mus musculus

<400> SEQUENCE: 9
gacattgtgc tgacccaatc tccagcttct ttggctgtgt ctctagggca gagggccacc        60
atatcctgca gagccagtga aagtgttgat aattatggct atagttttat gcactggtac     120
cagcagaaac caggacagcc accccaactc ctcatctatc gtgcatccaa cctagaatct     180
gggatccctg ccaggttcag tggcagtggg tctaggacag gcttcaccct caccattaat     240
cctgtggagg ctgatgatgt tgcaacctat tactgtcagc aaagtaaaga atatccgacg     300
ttcggtggag gcaccaagct ggaagtcaaa                                      330

<210> SEQ ID NO 10

-continued

```
<211> LENGTH: 110
<212> TYPE: PRT
<213> ORGANISM: Mus musculus

<400> SEQUENCE: 10

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Tyr Ser Phe Met His Trp Tyr Gln Gln Lys Pro Gly Gln Pro Pro
        35                  40                  45

Gln Leu Leu Ile Tyr Arg Ala Ser Asn Leu Glu Ser Gly Ile Pro Ala
    50                  55                  60

Arg Phe Ser Gly Ser Gly Ser Arg Thr Gly Phe Thr Leu Thr Ile Asn
65                  70                  75                  80

Pro Val Glu Ala Asp Asp Val Ala Thr Tyr Tyr Cys Gln Gln Ser Lys
                85                  90                  95

Glu Tyr Pro Thr Phe Gly Gly Gly Thr Lys Leu Glu Val Lys
            100                 105                 110

<210> SEQ ID NO 11
<211> LENGTH: 10
<212> TYPE: PRT
<213> ORGANISM: Mus musculus

<400> SEQUENCE: 11

Gly Phe Ser Leu Thr Ser Tyr Gly Val His
1               5                   10

<210> SEQ ID NO 12
<211> LENGTH: 16
<212> TYPE: PRT
<213> ORGANISM: Mus musculus

<400> SEQUENCE: 12

Val Ile Trp Ala Gly Gly Ser Thr Asn Tyr Asn Ser Ala Leu Met Ser
1               5                   10                  15

<210> SEQ ID NO 13
<211> LENGTH: 12
<212> TYPE: PRT
<213> ORGANISM: Mus musculus

<400> SEQUENCE: 13

Ala Arg Ala Tyr Gly Asn Tyr Trp Tyr Ile Asp Val
1               5                   10

<210> SEQ ID NO 14
<211> LENGTH: 11
<212> TYPE: PRT
<213> ORGANISM: Mus musculus

<400> SEQUENCE: 14

Lys Ala Ser Gln Ser Val Ser Asn Asp Val Ala
1               5                   10

<210> SEQ ID NO 15
<211> LENGTH: 7
<212> TYPE: PRT
<213> ORGANISM: Mus musculus

<400> SEQUENCE: 15

Tyr Ala Phe His Arg Phe Thr
```

-continued

```
<210> SEQ ID NO 16
<211> LENGTH: 9
<212> TYPE: PRT
<213> ORGANISM: Mus musculus

<400> SEQUENCE: 16

His Gln Ala Tyr Ser Ser Pro Tyr Thr
1               5

<210> SEQ ID NO 17
<211> LENGTH: 10
<212> TYPE: PRT
<213> ORGANISM: Mus musculus

<400> SEQUENCE: 17

Gly Tyr Thr Phe Thr Asn Tyr Gly Met Asn
1               5                   10

<210> SEQ ID NO 18
<211> LENGTH: 17
<212> TYPE: PRT
<213> ORGANISM: Mus musculus

<400> SEQUENCE: 18

Trp Ile Asn Asn Asn Asn Gly Glu Pro Thr Tyr Ala Glu Glu Phe Lys
1               5                   10                  15

Gly

<210> SEQ ID NO 19
<211> LENGTH: 7
<212> TYPE: PRT
<213> ORGANISM: Mus musculus

<400> SEQUENCE: 19

Ala Arg Asp Val Met Asp Tyr
1               5

<210> SEQ ID NO 20
<211> LENGTH: 15
<212> TYPE: PRT
<213> ORGANISM: Mus musculus

<400> SEQUENCE: 20

Arg Ala Ser Glu Ser Val Asp Asn Tyr Gly Tyr Ser Phe Met His
1               5                   10                  15

<210> SEQ ID NO 21
<211> LENGTH: 7
<212> TYPE: PRT
<213> ORGANISM: Mus musculus

<400> SEQUENCE: 21

Arg Ala Ser Asn Leu Glu Ser
1               5

<210> SEQ ID NO 22
<211> LENGTH: 8
<212> TYPE: PRT
<213> ORGANISM: Mus musculus

<400> SEQUENCE: 22

Gln Gln Ser Lys Glu Tyr Pro Thr
1               5
```

<210> SEQ ID NO 23
<211> LENGTH: 354
<212> TYPE: DNA
<213> ORGANISM: Artificial Sequence
<220> FEATURE:
<223> OTHER INFORMATION: 317-4B6 cDNA-Vh

<400> SEQUENCE: 23

```
caggtgcagc tgcaggagtc gggaccagga ctggtgaagc cttcggagac cctgtccctc      60
acctgcactg tctctggggt ttcattaacc agctatggtg tacactggat ccggcagccc     120
ccagggaagg gactggagtg gatcggggtc atatacgccg atggaagcac aaattataat     180
ccctccctca gagtcgagt gaccatatca aagacacct ccaagaacca ggtttccctg       240
aagctgagct ctgtgaccgc tgcggacacg gccgtgtatt actgtgcgag agcctatggt     300
aactactggt acatcgatgt ctggggccaa gggaccacgg tcaccgtctc ctca           354
```

<210> SEQ ID NO 24
<211> LENGTH: 118
<212> TYPE: PRT
<213> ORGANISM: Artificial Sequence
<220> FEATURE:
<223> OTHER INFORMATION: 317-4B6 pro-Vh

<400> SEQUENCE: 24

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Tyr Ala Asp Gly Ser Thr Asn Tyr Asn Pro Ser Leu Lys
    50                  55                  60

Ser Arg Val Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115
```

<210> SEQ ID NO 25
<211> LENGTH: 321
<212> TYPE: DNA
<213> ORGANISM: Artificial Sequence
<220> FEATURE:
<223> OTHER INFORMATION: 317-4B6 cDNA-Vk

<400> SEQUENCE: 25

```
gacatcgtga tgacccagtc tccagactcc ctggctgtgt ctctgggcga gagggccacc      60
atcaactgca gtccagcga gagtgtgagt aatgatgtag cttggtacca gcagaaacca     120
ggacagcctc ctaagctgct cattaactat gcatttcatc gcttcactgg ggtccctgac     180
cgattcagtg gcagcgggta tggacagat ttcactctca ccatcagcag cctgcaggct     240
gaagatgtgg cagtttatta ctgtcaccag gcttatagtt ctccgtacac gtttggccag    300
gggaccaagc tggagatcaa a                                              321
```

```
<210> SEQ ID NO 26
<211> LENGTH: 107
<212> TYPE: PRT
<213> ORGANISM: Artificial Sequence
<220> FEATURE:
<223> OTHER INFORMATION: 317-4B6 pro-Vk

<400> SEQUENCE: 26

Asp Ile Val Met Thr Gln Ser Pro Asp Ser Leu Ala Val Ser Leu Gly
1               5                   10                  15

Glu Arg Ala Thr Ile Asn Cys Lys Ser Ser Glu Ser Val Ser Asn Asp
            20                  25                  30

Val Ala Trp Tyr Gln Gln Lys Pro Gly Gln Pro Lys Leu Leu Ile
        35                  40                  45

Asn Tyr Ala Phe His Arg Phe Thr Gly Val Pro Asp Arg Phe Ser Gly
    50                  55                  60

Ser Gly Tyr Gly Thr Asp Phe Thr Leu Thr Ile Ser Ser Leu Gln Ala
65                  70                  75                  80

Glu Asp Val Ala Val Tyr Tyr Cys His Gln Ala Tyr Ser Ser Pro Tyr
                85                  90                  95

Thr Phe Gly Gln Gly Thr Lys Leu Glu Ile Lys
            100                 105

<210> SEQ ID NO 27
<211> LENGTH: 342
<212> TYPE: DNA
<213> ORGANISM: Artificial Sequence
<220> FEATURE:
<223> OTHER INFORMATION: 326-4A3 cDNA-Vh

<400> SEQUENCE: 27
caggtgcagc tggtgcagag cggcagcgag ctgaagaagc ccggcgccag cgtgaaggtg     60
agctgcaagg ccagcggcta caccttcacc aactacggca tgaactgggt gagacaggcc    120
cccggccagg gcctgaagtg gatgggctgg atcaacaaca acaacgccga gcccacctac    180
gcccaggact tcagaggcag attcgtgttc agcctggaca ccagcgccag caccgcctac    240
ctgcagatca gcagcctgaa gaccgaggac accgccgtgt actactgcgc cagagacgtg    300
atggactact ggggccaggg cacccctggtg accgtgagca gc                      342

<210> SEQ ID NO 28
<211> LENGTH: 114
<212> TYPE: PRT
<213> ORGANISM: Artificial Sequence
<220> FEATURE:
<223> OTHER INFORMATION: 326-4A3 pro-Vh

<400> SEQUENCE: 28

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Asn Asn Asn Ala Glu Pro Thr Tyr Ala Gln Asp Phe
    50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Tyr Cys
                85                  90                  95
```

```
Ala Arg Asp Val Met Asp Tyr Trp Gly Gln Gly Thr Leu Val Thr Val
            100                 105                 110

Ser Ser

<210> SEQ ID NO 29
<211> LENGTH: 330
<212> TYPE: DNA
<213> ORGANISM: Artificial Sequence
<220> FEATURE:
<223> OTHER INFORMATION: 326-4A3 cDNA-Vk

<400> SEQUENCE: 29
gacattgtgc tgacccagtc tccagcctcc ttggccgtgt ctccaggaca gagggccacc    60
atcacctgca gagccagtga aagtgttgat aattatggct atagttttat gcactggtat   120
cagcagaaac aggacaacc tcctaaactc ctgatttacc gtgcatccaa cctagaatct    180
ggggtcccag ccaggttcag cggcagtggg tctgggaccg atttcaccct cacaattaat   240
cctgtggaag ctgaggatac tgcaaattat tactgtcagc aaagtaaaga atatccgacg   300
ttcggcggag ggaccaaggt ggagatcaaa                                    330

<210> SEQ ID NO 30
<211> LENGTH: 110
<212> TYPE: PRT
<213> ORGANISM: Artificial Sequence
<220> FEATURE:
<223> OTHER INFORMATION: 326-4A3 pro-Vk

<400> SEQUENCE: 30

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
            20                  25                  30

Gly Tyr Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Glu Asp Thr Ala Asn Tyr Tyr Cys Gln Gln Ser Lys
                85                  90                  95

Glu Tyr Pro Thr Phe Gly Gly Gly Thr Lys Val Glu Ile Lys
            100                 105                 110

<210> SEQ ID NO 31
<211> LENGTH: 10
<212> TYPE: PRT
<213> ORGANISM: Mus musculus

<400> SEQUENCE: 31

Gly Phe Ser Leu Thr Ser Tyr Gly Val His
1               5                   10

<210> SEQ ID NO 32
<211> LENGTH: 16
<212> TYPE: PRT
<213> ORGANISM: Artificial Sequence
<220> FEATURE:
<223> OTHER INFORMATION: 317-4B6 H-CDR2 or CDR-H2

<400> SEQUENCE: 32

Val Ile Tyr Ala Asp Gly Ser Thr Asn Tyr Asn Pro Ser Leu Lys Ser
```

```
1               5                  10                 15
```

<210> SEQ ID NO 33
<211> LENGTH: 12
<212> TYPE: PRT
<213> ORGANISM: Mus musculus

<400> SEQUENCE: 33

Ala Arg Ala Tyr Gly Asn Tyr Trp Tyr Ile Asp Val
1               5                  10

<210> SEQ ID NO 34
<211> LENGTH: 11
<212> TYPE: PRT
<213> ORGANISM: Artificial Sequence
<220> FEATURE:
<223> OTHER INFORMATION: 317-4B6 L-CDR1 or CDR-L1

<400> SEQUENCE: 34

Lys Ser Ser Glu Ser Val Ser Asn Asp Val Ala
1               5                  10

<210> SEQ ID NO 35
<211> LENGTH: 7
<212> TYPE: PRT
<213> ORGANISM: Mus musculus

<400> SEQUENCE: 35

Tyr Ala Phe His Arg Phe Thr
1               5

<210> SEQ ID NO 36
<211> LENGTH: 9
<212> TYPE: PRT
<213> ORGANISM: Mus musculus

<400> SEQUENCE: 36

His Gln Ala Tyr Ser Ser Pro Tyr Thr
1               5

<210> SEQ ID NO 37
<211> LENGTH: 10
<212> TYPE: PRT
<213> ORGANISM: Mus musculus

<400> SEQUENCE: 37

Gly Tyr Thr Phe Thr Asn Tyr Gly Met Asn
1               5                  10

<210> SEQ ID NO 38
<211> LENGTH: 17
<212> TYPE: PRT
<213> ORGANISM: Artificial Sequence
<220> FEATURE:
<223> OTHER INFORMATION: 326-4A3 H-CDR2 or CDR-H2

<400> SEQUENCE: 38

Trp Ile Asn Asn Asn Asn Ala Glu Pro Thr Tyr Ala Gln Asp Phe Arg
1               5                  10                 15

Gly

<210> SEQ ID NO 39
<211> LENGTH: 7
<212> TYPE: PRT
<213> ORGANISM: Mus musculus

-continued

<400> SEQUENCE: 39

Ala Arg Asp Val Met Asp Tyr
1               5

<210> SEQ ID NO 40
<211> LENGTH: 15
<212> TYPE: PRT
<213> ORGANISM: Mus musculus

<400> SEQUENCE: 40

Arg Ala Ser Glu Ser Val Asp Asn Tyr Gly Tyr Ser Phe Met His
1               5                   10                  15

<210> SEQ ID NO 41
<211> LENGTH: 7
<212> TYPE: PRT
<213> ORGANISM: Mus musculus

<400> SEQUENCE: 41

Arg Ala Ser Asn Leu Glu Ser
1               5

<210> SEQ ID NO 42
<211> LENGTH: 8
<212> TYPE: PRT
<213> ORGANISM: Mus musculus

<400> SEQUENCE: 42

Gln Gln Ser Lys Glu Tyr Pro Thr
1               5

<210> SEQ ID NO 43
<211> LENGTH: 118
<212> TYPE: PRT
<213> ORGANISM: Artificial Sequence
<220> FEATURE:
<223> OTHER INFORMATION: 317-4B2 pro-Vh

<400> SEQUENCE: 43

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Tyr Ala Gly Gly Ser Thr Asn Tyr Asn Pro Ser Leu Lys
    50                  55                  60

Ser Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115

<210> SEQ ID NO 44
<211> LENGTH: 107
<212> TYPE: PRT
<213> ORGANISM: Artificial Sequence
<220> FEATURE:
<223> OTHER INFORMATION: 317-4B2 pro-Vk

```
<400> SEQUENCE: 44

Asp Ile Val Met Thr Gln Ser Pro Asp Ser Leu Ala Val Ser Leu Gly
1               5                   10                  15

Glu Arg Ala Thr Ile Asn Cys Lys Ser Ser Glu Ser Val Ser Asn Asp
            20                  25                  30

Val Ala Trp Tyr Gln Gln Lys Pro Gly Gln Pro Pro Lys Leu Leu Ile
        35                  40                  45

Asn Tyr Ala Phe His Arg Phe Thr Gly Val Pro Asp Arg Phe Ser Gly
    50                  55                  60

Ser Gly Tyr Gly Thr Asp Phe Thr Leu Thr Ile Ser Ser Leu Gln Ala
65                  70                  75                  80

Glu Asp Val Ala Val Tyr Tyr Cys His Gln Ala Tyr Ser Ser Pro Tyr
                85                  90                  95

Thr Phe Gly Gln Gly Thr Lys Leu Glu Ile Lys
            100                 105

<210> SEQ ID NO 45
<211> LENGTH: 118
<212> TYPE: PRT
<213> ORGANISM: Artificial Sequence
<220> FEATURE:
<223> OTHER INFORMATION: 317-4B5 pro-Vh

<400> SEQUENCE: 45

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Tyr Ala Gly Gly Ser Thr Asn Tyr Asn Pro Ser Leu Lys
    50                  55                  60

Ser Arg Val Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115

<210> SEQ ID NO 46
<211> LENGTH: 107
<212> TYPE: PRT
<213> ORGANISM: Artificial Sequence
<220> FEATURE:
<223> OTHER INFORMATION: 317-4B5 pro-Vk

<400> SEQUENCE: 46

Asp Ile Val Met Thr Gln Ser Pro Asp Ser Leu Ala Val Ser Leu Gly
1               5                   10                  15

Glu Arg Ala Thr Ile Asn Cys Lys Ser Ser Glu Ser Val Ser Asn Asp
            20                  25                  30

Val Ala Trp Tyr Gln Gln Lys Pro Gly Gln Pro Pro Lys Leu Leu Ile
        35                  40                  45

Asn Tyr Ala Phe His Arg Phe Thr Gly Val Pro Asp Arg Phe Ser Gly
    50                  55                  60

Ser Gly Tyr Gly Thr Asp Phe Thr Leu Thr Ile Ser Ser Leu Gln Ala
```

```
                65                  70                  75                  80
Glu Asp Val Ala Val Tyr Tyr Cys His Gln Ala Tyr Ser Ser Pro Tyr
                    85                  90                  95

Thr Phe Gly Gln Gly Thr Lys Leu Glu Ile Lys
                100                 105

<210> SEQ ID NO 47
<211> LENGTH: 354
<212> TYPE: DNA
<213> ORGANISM: Artificial Sequence
<220> FEATURE:
<223> OTHER INFORMATION: 317-1 cDNA-Vh

<400> SEQUENCE: 47
caggtgcagc tgcaggagtc gggaccagga ctggtgaagc cttcggagac cctgtccctc     60
acctgcactg tctctgggtt ttcattaacc agctatggtg tacactggat ccggcagccc    120
ccagggaagg gactggagtg gctgggggtc atatgggccg gtggaagcac aaattataat    180
ccctccctca agagtcgact gaccatatca aagacaactc caagagcca ggtttccctg     240 aagatgagct ctgtgaccgc tgcggacacg gccgtgtatt actgtgcgag agcctatggt    300
aactactggt acatcgatgt ctggggccaa gggaccacgg tcaccgtctc ctca          354

<210> SEQ ID NO 48
<211> LENGTH: 118
<212> TYPE: PRT
<213> ORGANISM: Artificial Sequence
<220> FEATURE:
<223> OTHER INFORMATION: 317-1 pro-Vh

<400> SEQUENCE: 48

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Leu
        35                  40                  45

Gly Val Ile Trp Ala Gly Gly Ser Thr Asn Tyr Asn Pro Ser Leu Lys
    50                  55                  60

Ser Arg Leu Thr Ile Ser Lys Asp Asn Ser Lys Ser Gln Val Ser Leu
65                  70                  75                  80

Lys Met Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
                100                 105                 110

Thr Val Thr Val Ser Ser
            115

<210> SEQ ID NO 49
<211> LENGTH: 321
<212> TYPE: DNA
<213> ORGANISM: Artificial Sequence
<220> FEATURE:
<223> OTHER INFORMATION: 317-1 cDNA-Vk

<400> SEQUENCE: 49
gacatcgtga tgacccagtc tccagactcc ctggctgtgt ctctgggcga gagggccacc     60
atcaactgca aggccagcca gagtgtgagt aatgatgtag cttggtacca gcagaaacca    120
ggacagcctc ctaagctgct cattaactat gcatttcatc gcttcactgg ggtccctgac    180
```

```
cgattcagtg gcagcgggta tgggacagat ttcactctca ccatcagcag cctgcaggct    240
gaagatgtgg cagtttatta ctgtcaccag gcttatagtt ctccgtacac gtttggcggg    300
gggaccaagc tggagatcaa a                                              321
```

```
<210> SEQ ID NO 50
<211> LENGTH: 107
<212> TYPE: PRT
<213> ORGANISM: Artificial Sequence
<220> FEATURE:
<223> OTHER INFORMATION: 317-1 pro-Vk

<400> SEQUENCE: 50

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Asn Asp
            20                  25                  30

Val Ala Trp Tyr Gln Gln Lys Pro Gly Gln Pro Pro Lys Leu Leu Ile
        35                  40                  45

Asn Tyr Ala Phe His Arg Phe Thr Gly Val Pro Asp Arg Phe Ser Gly
    50                  55                  60

Ser Gly Tyr Gly Thr Asp Phe Thr Leu Thr Ile Ser Ser Leu Gln Ala
65                  70                  75                  80

Glu Asp Val Ala Val Tyr Tyr Cys His Gln Ala Tyr Ser Ser Pro Tyr
                85                  90                  95

Thr Phe Gly Gly Gly Thr Lys Leu Glu Ile Lys
            100                 105

<210> SEQ ID NO 51
<211> LENGTH: 114
<212> TYPE: PRT
<213> ORGANISM: Artificial Sequence
<220> FEATURE:
<223> OTHER INFORMATION: 326-3B1 pro-Vh

<400> SEQUENCE: 51

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Asn Asn Gly Glu Pro Thr Tyr Ala Gln Asp Phe
    50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Tyr Cys
                85                  90                  95

Ala Arg Asp Val Met Asp Tyr Trp Gly Gln Gly Thr Leu Val Thr Val
            100                 105                 110

Ser Ser

<210> SEQ ID NO 52
<211> LENGTH: 110
<212> TYPE: PRT
<213> ORGANISM: Artificial Sequence
<220> FEATURE:
<223> OTHER INFORMATION: 326-3B1 pro-Vk

<400> SEQUENCE: 52
```

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
            20                  25                  30

Gly Tyr Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Ala
    50                  55                  60

Arg Phe Ser Gly Ser Gly Ser Arg Thr Asp Phe Thr Leu Thr Ile Asn
65                  70                  75                  80

Pro Val Glu Ala Asn Asp Thr Ala Asn Tyr Tyr Cys Gln Gln Ser Lys
                85                  90                  95

Glu Tyr Pro Thr Phe Gly Gly Gly Thr Lys Val Glu Ile Lys
            100                 105                 110

<210> SEQ ID NO 53
<211> LENGTH: 114
<212> TYPE: PRT
<213> ORGANISM: Artificial Sequence
<220> FEATURE:
<223> OTHER INFORMATION: 326-3G1 pro-Vh

<400> SEQUENCE: 53

Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Asn Asn Gly Glu Pro Thr Tyr Ala Gln Asp Phe
    50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Tyr Cys
                85                  90                  95

Ala Arg Asp Val Met Asp Tyr Trp Gly Gln Gly Thr Leu Val Thr Val
            100                 105                 110

Ser Ser

<210> SEQ ID NO 54
<211> LENGTH: 110
<212> TYPE: PRT
<213> ORGANISM: Artificial Sequence
<220> FEATURE:
<223> OTHER INFORMATION: 326-3G1 pro-Vk

<400> SEQUENCE: 54

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
            20                  25                  30

Gly Tyr Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Ala
    50                  55                  60

Arg Phe Ser Gly Ser Gly Ser Arg Thr Asp Phe Thr Leu Thr Ile Asn
65                  70                  75                  80

Pro Val Glu Ala Asn Asp Thr Ala Asn Tyr Tyr Cys Gln Gln Ser Lys

Glu Tyr Pro Thr Phe Gly Gly Gly Thr Lys Val Glu Ile Lys
                100                 105                 110

<210> SEQ ID NO 55
<211> LENGTH: 342
<212> TYPE: DNA
<213> ORGANISM: Artificial Sequence
<220> FEATURE:
<223> OTHER INFORMATION: 326-1 cDNA-Vh

<400> SEQUENCE: 55
caggtgcagc tggtgcagag cggcagcgag ctgaagaagc ccggcgccag cgtgaaggtg      60
agctgcaagg ccagcggcta caccttcacc aactacggca tgaactgggt gagacaggcc     120
cccggccagg gcctggagtg gatgggctgg atcaacaaca caacggcga gcccacctac     180 gcccagggct tcagaggcag attcgtgttc agcctggaca ccagcgccag caccgcctac     240
ctgcagatca gcagcctgaa gaccgaggac accgccgtgt acttctgcgc cagagacgtg     300
atggactact ggggccaggg caccaccgtg accgtgagca gc                        342

<210> SEQ ID NO 56
<211> LENGTH: 114
<212> TYPE: PRT
<213> ORGANISM: Artificial Sequence
<220> FEATURE:
<223> OTHER INFORMATION: 326-1 pro-Vh

<400> SEQUENCE: 56

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Asn Asn Asn Gly Glu Pro Thr Tyr Ala Gln Gly Phe
    50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Phe Cys
                85                  90                  95

Ala Arg Asp Val Met Asp Tyr Trp Gly Gln Gly Thr Thr Val Thr Val
            100                 105                 110

Ser Ser

<210> SEQ ID NO 57
<211> LENGTH: 330
<212> TYPE: DNA
<213> ORGANISM: Artificial Sequence
<220> FEATURE:
<223> OTHER INFORMATION: 326-1 cDNA-Vk

<400> SEQUENCE: 57
gacattgtgc tgacccagtc tccagcctcc ttggccgtgt ctccaggaca gagggccacc      60
atcacctgca gagccagtga aagtgttgat aattatggct atagttttat gcactggtat     120
cagcagaaac aggacaacc tcctaaactc ctgatttacc gtgcatccaa ctagaatct      180 ggggtcccag ccaggttcag cggcagtggg tctaggaccg atttcaccct cacaattaat     240
cctgtggaag ctaatgatac tgcaaattat tactgtcagc aaagtaaaga atatccgacg     300

```
ttcggcggag ggaccaaggt ggagatcaaa                                    330
```

<210> SEQ ID NO 58
<211> LENGTH: 110
<212> TYPE: PRT
<213> ORGANISM: Artificial Sequence
<220> FEATURE:
<223> OTHER INFORMATION: 326-1 pro-Vk

<400> SEQUENCE: 58

```
Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
            20                  25                  30

Gly Tyr Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Ala
    50                  55                  60

Arg Phe Ser Gly Ser Gly Ser Arg Thr Asp Phe Thr Leu Thr Ile Asn
65                  70                  75                  80

Pro Val Glu Ala Asn Asp Thr Ala Asn Tyr Tyr Cys Gln Gln Ser Lys
                85                  90                  95

Glu Tyr Pro Thr Phe Gly Gly Gly Thr Lys Val Glu Ile Lys
            100                 105                 110
```

<210> SEQ ID NO 59
<211> LENGTH: 16
<212> TYPE: PRT
<213> ORGANISM: Artificial Sequence
<220> FEATURE:
<223> OTHER INFORMATION: 317-1 H-CDR2 or CDR-H2

<400> SEQUENCE: 59

```
Val Ile Trp Ala Gly Gly Ser Thr Asn Tyr Asn Pro Ser Leu Lys Ser
1               5                   10                  15
```

<210> SEQ ID NO 60
<211> LENGTH: 16
<212> TYPE: PRT
<213> ORGANISM: Artificial Sequence
<220> FEATURE:
<223> OTHER INFORMATION: 317-4B2 H-CDR2 or CDR-H2

<400> SEQUENCE: 60

```
Val Ile Tyr Ala Gly Gly Ser Thr Asn Tyr Asn Pro Ser Leu Lys Ser
1               5                   10                  15
```

<210> SEQ ID NO 61
<211> LENGTH: 11
<212> TYPE: PRT
<213> ORGANISM: Artificial Sequence
<220> FEATURE:
<223> OTHER INFORMATION: 317-4B2 L-CDR1 or CDR-L1

<400> SEQUENCE: 61

```
Lys Ser Ser Glu Ser Val Ser Asn Asp Val Ala
1               5                   10
```

<210> SEQ ID NO 62
<211> LENGTH: 17
<212> TYPE: PRT
<213> ORGANISM: Artificial Sequence
<220> FEATURE:
<223> OTHER INFORMATION: 326-1 H-CDR2 or CDR-H2

<400> SEQUENCE: 62

Trp Ile Asn Asn Asn Gly Glu Pro Thr Tyr Ala Gln Gly Phe Arg
1               5                   10                  15

Gly

<210> SEQ ID NO 63
<211> LENGTH: 17
<212> TYPE: PRT
<213> ORGANISM: Artificial Sequence
<220> FEATURE:
<223> OTHER INFORMATION: 326-3G1 H-CDR2 or CDR-H2

<400> SEQUENCE: 63

Trp Ile Asn Asn Asn Gly Glu Pro Thr Tyr Ala Gln Asp Phe Arg
1               5                   10                  15

Gly

<210> SEQ ID NO 64
<211> LENGTH: 118
<212> TYPE: PRT
<213> ORGANISM: Artificial Sequence
<220> FEATURE:
<223> OTHER INFORMATION: 317-3A1 pro-Vh

<400> SEQUENCE: 64

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Trp Ala Gly Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115

<210> SEQ ID NO 65
<211> LENGTH: 118
<212> TYPE: PRT
<213> ORGANISM: Artificial Sequence
<220> FEATURE:
<223> OTHER INFORMATION: 317-3C1 pro-Vh

<400> SEQUENCE: 65

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Leu
        35                  40                  45

Gly Val Ile Trp Ala Gly Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

```
Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115

<210> SEQ ID NO 66
<211> LENGTH: 118
<212> TYPE: PRT
<213> ORGANISM: Artificial Sequence
<220> FEATURE:
<223> OTHER INFORMATION: 317-3E1 pro-Vh

<400> SEQUENCE: 66

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Trp Ala Gly Gly Ser Thr Asn Tyr Asn Pro Ser Leu Lys
    50                  55                  60

Ser Arg Val Thr Ile Ser Val Asp Thr Ser Lys Ser Gln Phe Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115

<210> SEQ ID NO 67
<211> LENGTH: 118
<212> TYPE: PRT
<213> ORGANISM: Artificial Sequence
<220> FEATURE:
<223> OTHER INFORMATION: 317-3F1 pro-Vh

<400> SEQUENCE: 67

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Trp Ala Gly Gly Ser Thr Asn Tyr Asn Pro Ser Leu Lys
    50                  55                  60

Ser Arg Val Thr Ile Ser Val Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115

<210> SEQ ID NO 68
```

```
<211> LENGTH: 118
<212> TYPE: PRT
<213> ORGANISM: Artificial Sequence
<220> FEATURE:
<223> OTHER INFORMATION: 317-3G1 pro-Vh

<400> SEQUENCE: 68

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Trp Ala Gly Gly Ser Thr Asn Tyr Asn Pro Ser Leu Lys
    50                  55                  60

Ser Arg Val Thr Ile Ser Val Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115

<210> SEQ ID NO 69
<211> LENGTH: 118
<212> TYPE: PRT
<213> ORGANISM: Artificial Sequence
<220> FEATURE:
<223> OTHER INFORMATION: 317-3H1 pro-Vh

<400> SEQUENCE: 69

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Trp Ala Gly Gly Ser Thr Asn Tyr Asn Pro Ser Leu Lys
    50                  55                  60

Ser Arg Val Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115

<210> SEQ ID NO 70
<211> LENGTH: 118
<212> TYPE: PRT
<213> ORGANISM: Artificial Sequence
<220> FEATURE:
<223> OTHER INFORMATION: 317-3I1 pro-Vh

<400> SEQUENCE: 70

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
```

```
                    20                  25                  30
Gly Val His Trp Ile Arg Gln Pro Gly Lys Gly Leu Glu Trp Ile
            35                  40                  45
Gly Val Ile Trp Ala Gly Gly Ser Thr Asn Tyr Asn Pro Ser Leu Lys
        50                  55                  60
Ser Arg Val Thr Ile Ser Lys Asp Thr Ser Lys Asn Gln Val Ser Leu
65                  70                  75                  80
Lys Leu Ser Ser Val Thr Ala Ala Asp Thr Ala Val Tyr Tyr Cys Ala
                85                  90                  95
Arg Ala Tyr Gly Asn Tyr Trp Tyr Ile Asp Val Trp Gly Gln Gly Thr
                100                 105                 110
Thr Val Thr Val Ser Ser
            115

<210> SEQ ID NO 71
<211> LENGTH: 118
<212> TYPE: PRT
<213> ORGANISM: Artificial Sequence
<220> FEATURE:
<223> OTHER INFORMATION: 317-4B1 pro-Vh

<400> SEQUENCE: 71

Gln Val Gln Leu Gln Glu Ser Gly Pro Gly Leu Val Lys Pro Ser Glu
1               5                   10                  15
Thr Leu Ser Leu Thr Cys Thr Val Ser Gly Phe Ser Leu Thr Ser Tyr
            20                  25                  30
Gly Val His Trp Ile Arg Gln Pro Gly Lys Gly Leu Glu Trp Ile
            35                  40                  45
Gly Val Ile Trp Ala Gly Gly Ser Thr Asn Tyr Asn Pro Ser Leu Lys
        50                  55                  60
Ser Arg Val Thr Ile Ser Lys Asp Thr Ser Lys Asn Gln Phe Ser Leu
65                  70                  75                  80
Lys Leu Ser Ser Val Thr Ala Ala Asp Thr Ala Val Tyr Tyr Cys Ala
                85                  90                  95
Arg Ala Tyr Gly Asn Tyr Trp Tyr Ile Asp Val Trp Gly Gln Gly Thr
                100                 105                 110
Thr Val Thr Val Ser Ser
            115

<210> SEQ ID NO 72
<211> LENGTH: 118
<212> TYPE: PRT
<213> ORGANISM: Artificial Sequence
<220> FEATURE:
<223> OTHER INFORMATION: 317-4B3 pro-Vh

<400> SEQUENCE: 72

Gln Val Gln Leu Gln Glu Ser Gly Pro Gly Leu Val Lys Pro Ser Glu
1               5                   10                  15
Thr Leu Ser Leu Thr Cys Thr Val Ser Gly Phe Ser Leu Thr Ser Tyr
            20                  25                  30
Gly Val His Trp Ile Arg Gln Pro Gly Lys Gly Leu Glu Trp Ile
            35                  40                  45
Gly Val Ile Asn Ala Gly Gly Ser Thr Asn Tyr Asn Pro Ser Leu Lys
        50                  55                  60
Ser Arg Val Thr Ile Ser Lys Asp Thr Ser Lys Asn Gln Phe Ser Leu
65                  70                  75                  80
Lys Leu Ser Ser Val Thr Ala Ala Asp Thr Ala Val Tyr Tyr Cys Ala
```

```
                    85                  90                  95
Arg Ala Tyr Gly Asn Tyr Trp Tyr Ile Asp Val Trp Gly Gln Gly Thr
                100                 105                 110

Thr Val Thr Val Ser Ser
        115

<210> SEQ ID NO 73
<211> LENGTH: 118
<212> TYPE: PRT
<213> ORGANISM: Artificial Sequence
<220> FEATURE:
<223> OTHER INFORMATION: 317-4B4 pro-Vh

<400> SEQUENCE: 73

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
                20                  25                  30

Gly Val His Trp Ile Arg Gln Pro Pro Gly Lys Gly Leu Glu Trp Ile
                35                  40                  45

Gly Val Ile Trp Ala Gly Gly Ser Thr Asn Tyr Asn Pro Ser Leu Lys
            50                  55                  60

Ser Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Pro Tyr Ile Asp Val Trp Gly Gln Gly Thr
                100                 105                 110

Thr Val Thr Val Ser Ser
        115

<210> SEQ ID NO 74
<211> LENGTH: 107
<212> TYPE: PRT
<213> ORGANISM: Artificial Sequence
<220> FEATURE:
<223> OTHER INFORMATION: 317-4A2 pro-Vk

<400> SEQUENCE: 74

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Ser Asn Asp
                20                  25                  30

Val Ala Trp Tyr Gln Gln Lys Pro Gly Gln Pro Pro Lys Leu Leu Ile
                35                  40                  45

Asn Tyr Ala Phe His Arg Phe Thr Gly Val Pro Asp Arg Phe Ser Gly
            50                  55                  60

Ser Gly Tyr Gly Thr Asp Phe Thr Leu Thr Ile Ser Ser Leu Gln Ala
65                  70                  75                  80

Glu Asp Val Ala Val Tyr Tyr Cys His Gln Ala Tyr Ser Ser Pro Tyr
                85                  90                  95

Thr Phe Gly Gln Gly Thr Lys Leu Glu Ile Lys
                100                 105

<210> SEQ ID NO 75
<211> LENGTH: 114
<212> TYPE: PRT
<213> ORGANISM: Artificial Sequence
<220> FEATURE:
<223> OTHER INFORMATION: 326-3A1 pro-Vh
```

-continued

```
<400> SEQUENCE: 75

Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Asn Asn Asn Gly Glu Pro Thr Tyr Ala Gln Gly Phe
    50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Tyr Cys
                85                  90                  95

Ala Arg Asp Val Met Asp Tyr Trp Gly Gln Gly Thr Leu Val Thr Val
            100                 105                 110

Ser Ser

<210> SEQ ID NO 76
<211> LENGTH: 114
<212> TYPE: PRT
<213> ORGANISM: Artificial Sequence
<220> FEATURE:
<223> OTHER INFORMATION: 326-3C1 pro-Vh

<400> SEQUENCE: 76

Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Asn Asn Asn Gly Glu Pro Thr Tyr Ala Gln Asp Phe
    50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Tyr Cys
                85                  90                  95

Ala Arg Asp Val Met Asp Tyr Trp Gly Gln Gly Thr Val Thr Val
            100                 105                 110

Ser Ser

<210> SEQ ID NO 77
<211> LENGTH: 114
<212> TYPE: PRT
<213> ORGANISM: Artificial Sequence
<220> FEATURE:
<223> OTHER INFORMATION: 326-3D1 pro-Vh

<400> SEQUENCE: 77

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Asn Asn Asn Gly Glu Pro Thr Tyr Ala Gln Gly Phe
    50                  55                  60
```

-continued

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Tyr Cys
                85                  90                  95

Ala Arg Asp Val Met Asp Tyr Trp Gly Gln Gly Thr Leu Val Thr Val
            100                 105                 110

Ser Ser

<210> SEQ ID NO 78
<211> LENGTH: 114
<212> TYPE: PRT
<213> ORGANISM: Artificial Sequence
<220> FEATURE:
<223> OTHER INFORMATION: 326-3E1 pro-Vh

<400> SEQUENCE: 78

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Lys Trp Met
            35                  40                  45

Gly Trp Ile Asn Asn Asn Asn Gly Glu Pro Thr Tyr Ala Gln Asp Phe
    50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Tyr Cys
                85                  90                  95

Ala Arg Asp Val Met Asp Tyr Trp Gly Gln Gly Thr Leu Val Thr Val
            100                 105                 110

Ser Ser

<210> SEQ ID NO 79
<211> LENGTH: 114
<212> TYPE: PRT
<213> ORGANISM: Artificial Sequence
<220> FEATURE:
<223> OTHER INFORMATION: 326-3F1 pro-Vh

<400> SEQUENCE: 79

Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Glu Trp Met
            35                  40                  45

Gly Trp Ile Asn Asn Asn Asn Gly Glu Pro Thr Tyr Ala Gln Gly Phe
    50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Tyr Cys
                85                  90                  95

Ala Arg Asp Val Met Asp Tyr Trp Gly Gln Gly Thr Leu Val Thr Val
            100                 105                 110

Ser Ser

<210> SEQ ID NO 80

```
<211> LENGTH: 114
<212> TYPE: PRT
<213> ORGANISM: Artificial Sequence
<220> FEATURE:
<223> OTHER INFORMATION: 326-3B N55D pro-Vh

<400> SEQUENCE: 80

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Lys Trp Met
            35                  40                  45

Gly Trp Ile Asn Asn Asn Asp Gly Glu Pro Thr Tyr Ala Gln Asp Phe
        50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Tyr Cys
                85                  90                  95

Ala Arg Asp Val Met Asp Tyr Trp Gly Gln Gly Thr Leu Val Thr Val
            100                 105                 110

Ser Ser

<210> SEQ ID NO 81
<211> LENGTH: 110
<212> TYPE: PRT
<213> ORGANISM: Artificial Sequence
<220> FEATURE:
<223> OTHER INFORMATION: 326-4A1 pro-Vk

<400> SEQUENCE: 81

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
                20                  25                  30

Gly Tyr Ser Phe Met His Trp Tyr Gln Gln Lys Pro Gly Gln Pro Pro
            35                  40                  45

Lys Leu Leu Ile Tyr Arg Ala Ser Asn Leu Glu Ser Gly Val Pro Ala
        50                  55                  60

Arg Phe Ser Gly Ser Gly Ser Arg Thr Asp Phe Thr Leu Thr Ile Asn
65                  70                  75                  80

Pro Val Glu Ala Glu Asp Thr Ala Asn Tyr Tyr Cys Gln Gln Ser Lys
                85                  90                  95

Glu Tyr Pro Thr Phe Gly Gly Gly Thr Lys Val Glu Ile Lys
            100                 105                 110

<210> SEQ ID NO 82
<211> LENGTH: 110
<212> TYPE: PRT
<213> ORGANISM: Artificial Sequence
<220> FEATURE:
<223> OTHER INFORMATION: 326-4A2 pro-Vk

<400> SEQUENCE: 82

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
                20                  25                  30

Gly Tyr Ser Phe Met His Trp Tyr Gln Gln Lys Pro Gly Gln Pro Pro
            35                  40                  45
```

```
Lys Leu Leu Ile Tyr Arg Ala Ser Asn Leu Glu Ser Gly Val Pro Ala
 50                  55                  60

Arg Phe Ser Gly Ser Gly Ser Gly Thr Asp Phe Thr Leu Thr Ile Asn
 65                  70                  75                  80

Pro Val Glu Ala Asn Asp Thr Ala Asn Tyr Tyr Cys Gln Gln Ser Lys
                 85                  90                  95

Glu Tyr Pro Thr Phe Gly Gly Gly Thr Lys Val Glu Ile Lys
            100                 105                 110

<210> SEQ ID NO 83
<211> LENGTH: 327
<212> TYPE: PRT
<213> ORGANISM: Artificial Sequence
<220> FEATURE:
<223> OTHER INFORMATION: huIgG4mt1 pro

<400> SEQUENCE: 83

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300
```

```
Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 84
<211> LENGTH: 327
<212> TYPE: PRT
<213> ORGANISM: Artificial Sequence
<220> FEATURE:
<223> OTHER INFORMATION: huIgG4mt2 pro

<400> SEQUENCE: 84

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Pro Val Ala Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

-continued

```
<210> SEQ ID NO 85
<211> LENGTH: 327
<212> TYPE: PRT
<213> ORGANISM: Artificial Sequence
<220> FEATURE:
<223> OTHER INFORMATION: huIgG4mt6 pro

<400> SEQUENCE: 85

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Val Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Ala Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 86
<211> LENGTH: 327
<212> TYPE: PRT
<213> ORGANISM: Artificial Sequence
<220> FEATURE:
<223> OTHER INFORMATION: huIgG4mt8 pro
```

<400> SEQUENCE: 86

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Pro Val Ala Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Thr Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 87
<211> LENGTH: 327
<212> TYPE: PRT
<213> ORGANISM: Artificial Sequence
<220> FEATURE:
<223> OTHER INFORMATION: huIgG4mt9 pro

<400> SEQUENCE: 87

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                      55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Pro Val Ala Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Ala Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Lys Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 88
<211> LENGTH: 327
<212> TYPE: PRT
<213> ORGANISM: Artificial Sequence
<220> FEATURE:
<223> OTHER INFORMATION: huIgG4mt10 pro

<400> SEQUENCE: 88

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                      55                  60
```

```
Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Pro Val Ala Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Ala Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Val His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Lys Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 89
<211> LENGTH: 367
<212> TYPE: PRT
<213> ORGANISM: Artificial Sequence
<220> FEATURE:
<223> OTHER INFORMATION: OS8 pro

<400> SEQUENCE: 89

Met Glu Arg His Trp Ile Phe Leu Leu Leu Ser Val Thr Ala Gly
  1               5                  10                  15

Val His Ser Gln Val Gln Leu Gln Gln Ser Gly Ala Glu Leu Ala Arg
                 20                  25                  30

Pro Gly Ala Ser Val Lys Met Ser Cys Lys Ala Ser Gly Tyr Thr Phe
             35                  40                  45

Thr Arg Tyr Thr Met His Trp Val Lys Gln Arg Pro Gly Gln Gly Leu
         50                  55                  60

Glu Trp Ile Gly Tyr Ile Asn Pro Ser Arg Gly Tyr Thr Asn Tyr Asn
 65                  70                  75                  80

Gln Lys Phe Lys Asp Lys Ala Thr Leu Thr Thr Asp Lys Ser Ser Ser
                 85                  90                  95
```

```
Thr Ala Tyr Met Gln Leu Ser Ser Leu Thr Ser Glu Asp Ser Ala Val
            100                 105                 110

Tyr Tyr Cys Ala Arg Tyr Tyr Asp Asp His Tyr Cys Leu Asp Tyr Trp
        115                 120                 125

Gly Gln Gly Thr Thr Leu Thr Val Ser Ser Gly Gly Gly Gly Ser Gly
    130                 135                 140

Gly Gly Gly Ser Gly Gly Gly Ser Gln Ile Val Leu Thr Gln Ser
145                 150                 155                 160

Pro Ala Ile Met Ser Ala Ser Pro Gly Glu Lys Val Thr Met Thr Cys
                165                 170                 175

Ser Ala Ser Ser Ser Val Ser Tyr Met Asn Trp Tyr Gln Gln Lys Ser
            180                 185                 190

Gly Thr Ser Pro Lys Arg Trp Ile Tyr Asp Thr Ser Lys Leu Ala Ser
        195                 200                 205

Gly Val Pro Ala His Phe Arg Gly Ser Gly Ser Gly Thr Ser Tyr Ser
    210                 215                 220

Leu Thr Ile Ser Gly Met Glu Ala Glu Asp Ala Ala Thr Tyr Tyr Cys
225                 230                 235                 240

Gln Gln Trp Ser Ser Asn Pro Phe Thr Phe Gly Ser Gly Thr Lys Leu
                245                 250                 255

Glu Ile Asn Ser Ser Val Val Pro Val Leu Gln Lys Val Asn Ser Thr
            260                 265                 270

Thr Thr Lys Pro Val Leu Arg Thr Pro Ser Pro Val His Pro Thr Gly
        275                 280                 285

Thr Ser Gln Pro Gln Arg Pro Glu Asp Cys Arg Pro Arg Gly Ser Val
    290                 295                 300

Lys Gly Thr Gly Leu Asp Phe Ala Cys Asp Ile Tyr Ile Trp Ala Pro
305                 310                 315                 320

Leu Ala Gly Ile Cys Val Ala Leu Leu Leu Ser Leu Ile Ile Thr Leu
                325                 330                 335

Ile Cys Tyr His Arg Ser Arg Lys Arg Val Cys Lys Cys Pro Arg Pro
        340                 345                 350

Leu Val Arg Gln Glu Gly Lys Pro Arg Pro Ser Glu Lys Ile Val
    355                 360                 365

<210> SEQ ID NO 90
<211> LENGTH: 304
<212> TYPE: PRT
<213> ORGANISM: Artificial Sequence
<220> FEATURE:
<223> OTHER INFORMATION: P3Z pro

<400> SEQUENCE: 90

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95
```

-continued

```
Val Thr Gln Leu Pro Asn Gly Arg Asp Phe His Met Ser Val Val Arg
            100                 105                 110
Ala Arg Arg Asn Asp Ser Gly Thr Tyr Leu Cys Gly Ala Ile Ser Leu
            115                 120                 125
Ala Pro Lys Ala Gln Ile Lys Glu Ser Leu Arg Ala Glu Leu Arg Val
            130                 135                 140
Thr Glu Arg Arg Ala Glu Val Pro Thr Ala His Pro Ser Pro Ser Pro
145                 150                 155                 160
Arg Pro Ala Gly Gln Phe Gln Thr Leu Val Val Gly Val Val Gly Gly
                    165                 170                 175
Leu Leu Gly Ser Leu Val Leu Leu Val Trp Val Leu Ala Val Ile Arg
                180                 185                 190
Val Lys Phe Ser Arg Ser Ala Asp Ala Pro Ala Tyr Gln Gln Gly Gln
            195                 200                 205
Asn Gln Leu Tyr Asn Glu Leu Asn Leu Gly Arg Arg Glu Glu Tyr Asp
            210                 215                 220
Val Leu Asp Lys Arg Arg Gly Arg Asp Pro Glu Met Gly Gly Lys Pro
225                 230                 235                 240
Gln Arg Arg Lys Asn Pro Gln Glu Gly Leu Tyr Asn Glu Leu Gln Lys
                    245                 250                 255
Asp Lys Met Ala Glu Ala Tyr Ser Glu Ile Gly Met Lys Gly Glu Arg
            260                 265                 270
Arg Arg Gly Lys Gly His Asp Gly Leu Tyr Gln Gly Leu Ser Thr Ala
            275                 280                 285
Thr Lys Asp Thr Tyr Asp Ala Leu His Met Gln Ala Leu Pro Pro Arg
            290                 295                 300
```

ANTI-PD1 ANTIBODIES AND THEIR USE AS THERAPEUTICS AND DIAGNOSTICS

INTRODUCTION

Programmed Death-1 (PD-1, also termed as CD279) is a 55 KD receptor protein related to CD28/CTLA4 co-stimulatory/inhibitory receptor family (Blank et al., 2005 Cancer Immunol Immunother 54:307-314). The genes and cDNAs coding for PD-1 were cloned and characterized in mouse and human (Ishida et al., 1992 EMBO J. 11:3887-3395; Shinohara et al., 1994 Genomics 23:704-706). The full length PD-1 contains 288 amino acid residues (NCBI accession number: NP_005009). Its extracellular domain consists of amino acid residues 1-167, and the cytoplasmic C-terminal tail comprises residues 191-288, which has two hypothetical immune-regulatory motifs, an immunoreceptor tyrosine-based inhibitory motif (ITIM; Vivier et al., 1997 Immunol Today 18:286-291) and an immunoreceptor tyrosine switch motif (ITSM; Chemnitz et al., 2004 J Immunol 173:945-954).

To date, two sequence-related ligands, PD-L1 (B7-H1) and PD-L2 (B7-DC), have been identified to specifically interact with PD-1, inducing intracellular signal transduction that inhibits CD3 and CD28 mediated T-cell activation (Riley, 2009 Immunol Rev 229:114-125), which, in turn, attenuates T-cell activities, for example, reduction of cell proliferation, IL-2 and IFN-γ secretion, as well as other growth factor and cytokine secretion.

Expression of PD-1 was frequently found in immune cells such as T-cells, B-cells, monocytes and natural killer (NK) cells. It was rarely expressed in other human tissues, such as muscle, epithelium, neuronal tissues, etc. Furthermore, high level of PD-1 expression is often associated with activation of immune cells. For example, when human T-cell line, Jurkat, was activated by phytohaemagglutinin (PHA) or phorbol ester (12-O-tetradecanoylphorbol-13-acetate, or TPA), the expression of PD-1 was up-regulated visible in Western Blot (Vibharka et al., 1997 Exp Cell Res 232:25-28). The same phenomenon was observed in stimulated murine T- and B-lymphocytes and in primary human CD4$^+$ T-cells upon stimulation by anti-CD3 antibody (Agata et al., 1996 Int Immunol 8:765-772; Bennett et al., 2003 J Immunol 170:711-118). The increase of PD-1 expression following stimulation of T effector cells redirects the activated T-effector cells towards exhaustion and reduced immune activities. Therefore, PD-1 mediated inhibitory signal plays an important role in immune tolerance (Bour-Jordan et al., 2011 Immunol Rev 241:180-205).

Increase of PD-1 expression in tumor-infiltrating lymphocytes (TILs) and PD-1 ligand expression in tumor cells were reported in varieties of cancers involved in different types of tissues and organs such as lung (Konishi et al., 2004 Clin Cancer Res 10:5094-5100), liver (Shi et al., 2008 Int J Cancer 128:887-896; Gao et al., 2009 Clin Cancer Res 15:971-979), stomach (Wu et al., 2006 Acta Histochem 108:19-24), kidney (Thompson et al., 2004 Proc Natl Acad Sci 101:17174-17179; Thompson et al., 2007 Clin Cancer Res 13:1757-1761), breast (Ghebeh et al., 2006 Neoplasia 8:190-198), ovary (Hamanishi et al. 2007 Proc Natl Acad Sci 104:3360-3365), pancreas (Nomi et al., 2007 Clin Cancer Res 13:2151-2157), melanocytes (Hino et al., 2010 Cancer 116:1757-1766) and esophagus (Ohigashi et al., 2005 Clin Cancer Res 11:2947-2953). More frequently, the increased expression of PD-1 and PD-L1 in those cancers is associated with poor prognosis of patient survival outcome. Transgenic mice with PD-1 gene knockout inhibiting xenograft cancer cell growth further elucidated the significance of PD-1 signaling in the modulation of immune system for cancer eradication or tolerance (Zhang et al., 2009 Blood 114:1545-1552).

Not only does up-regulation of PD-1 signaling leads to immune tolerance to cancerous growth, but also to viral infection and expansion in human. The prevalent liver infection viruses, HBV and HCV, induce overexpression of PD-1 ligands in hepatocytes and activate PD-1 signaling in T-effector cells, resulting in T-cell exhaustion and tolerance to the viral infection (Boni et al., 2007 J Virol 81:4215-4225; Golden-Mason et al., 2008 J Immunol 180:3637-3641). Likewise, HIV infection frequently evades human immune system by similar mechanisms. Therapeutic modulation of PD-1 signaling by antagonist molecules may revert immune cells from tolerance, and reactivated to eradicate cancer and chronic viral infection (Blank et al., 2005 Cancer Immunol Immunother 54:307-314; Okazaki et al., 2007 Int Immunol 19:813-824).

SUMMARY OF THE INVENTION

The invention provides methods and compositions for immune-inhibition of PD-1. In one aspect, the invention provides an antibody antigen binding domain which specifically binds human PD-1, and comprises a complementarity determining region (CDR) having a sequence selected from SEQ ID NOS 11-22, 31-42 and 59-63.

The CDRs are amenable to recombination into heavy chain variable region (Vh) and light chain variable regions (Vk) which comprise (CDR-H1, CDR-H2 and CDR-H3) and (CDR-L1, CDR-L2 and CDR-L3) sequences, respectively and retain PD-1-specific binding and/or functionality.

In particular embodiments, the domain comprises a heavy chain variable region (Vh) or a light chain variable region (Vk) comprising:

| | | |
|---|---|---|
| a) | CDR-H1 | (SEQ ID NO: 11, 17, 31, or 37), |
| b) | CDR-H2 | (SEQ ID NO: 12, 18, 32, or 38), |
| c) | CDR-H3 | (SEQ ID NO: 13, 18, 33, or 39); |
| d) | CDR-L1 | (SEQ ID NO: 14, 20, 34, or 40), |
| e) | CDR-L2 | (SEQ ID NO: 15, 21, 35, or 41), or |
| f) | CDR-L3 | (SEQ ID NO: 16, 22, 36, or 42). |

In particular embodiments, the domain comprises a heavy chain variable region (Vh) and/or a light chain variable region (Vk) comprising:

| | | | |
|---|---|---|---|
| a) | mu317 | CDR-H1, CDR-H2 and CDR-H3 | (SEQ ID NOS: 11-13); |
| | | CDR-L1, CDR-L2 and CDR-L3 | (SEQ ID NOS: 14-16); |
| b) | mu326 | CDR-H1, CDR-H2 and CDR-H3 | (SEQ ID NOS: 17-19); |
| | | CDR-L1, CDR-L2 and CDR-L3 | (SEQ ID NOS: 20-22); |

-continued

| | | | |
|---|---|---|---|
| c) | 317-4B6 | CDR-H1, CDR-H2 and CDR-H3 | (SEQ ID NOS: 31-33); |
| | | CDR-L1, CDR-L2 and CDR-L3 | (SEQ ID NOS: 34-36); |
| d) | 326-4A3 | CDR-H1, CDR-H2 and CDR-H3 | (SEQ ID NOS: 37-39); |
| | | CDR-L1, CDR-L2 and CDR-L3 | (SEQ ID NOS: 40-42); |
| e) | 317-1 | CDR-H1, CDR-H2 and CDR-H3 | (SEQ ID NOS: 11, 59, 13); |
| | | CDR-L1, CDR-L2 and CDR-L3 | (SEQ ID NOS: 14-16); |
| f) | 317-4B2 | CDR-H1, CDR-H2 and CDR-H3 | (SEQ ID NOS: 11, 60, 13); |
| | | CDR-L1, CDR-L2 and CDR-L3 | (SEQ ID NOS: 61, 15, 16); |
| g) | 317-4B5 | CDR-H1, CDR-H2 and CDR-H3 | (SEQ ID NOS: 11, 60, 13); |
| | | CDR-L1, CDR-L2 and CDR-L3 | (SEQ ID NOS: 61, 15, 16); |
| h) | 317-4B6 | CDR-H1, CDR-H2 and CDR-H3 | (SEQ ID NOS: 11, 32, 13); |
| | | CDR-L1, CDR-L2 and CDR-L3 | (SEQ ID NOS: 61, 15, 16); |
| i) | 326-1 | CDR-H1, CDR-H2 and CDR-H3 | (SEQ ID NOS: 17, 62, 19); |
| | | CDR-L1, CDR-L2 and CDR-L3 | (SEQ ID NOS: 20-22); |
| j) | 326-3B1 | CDR-H1, CDR-H2 and CDR-H3 | (SEQ ID NOS: 17, 62, 19); |
| | | CDR-L1, CDR-L2 and CDR-L3 | (SEQ ID NOS: 20-22); |
| k) | 326-3G1 | CDR-H1, CDR-H2 and CDR-H3 or | (SEQ ID NOS: 17, 62, 19); |
| | | CDR-L1, CDR-L2 and CDR-L3 | (SEQ ID NOS: 20-22). |

In particular embodiments, the domain comprises a heavy chain variable region (Vh) and a light chain variable region (Vk) comprising:

(a) CDR-H1 (SEQ ID NO 31), CDR-H2 (SEQ ID NO 12, 32, 59 or 60) and CDR-H3 (SEQ ID NO 33),
CDR-L1 (SEQ ID NO 14, 34 or 61), CDR-L2 (SEQ ID NO 35) and CDR-L3 (SEQ ID NO 36); or (b) CDR-H1 (SEQ ID NO 37), CDR-H2 (SEQ ID NO 18, 38 or 62) and CDR-H3 (SEQ ID NO 39),
CDR-L1 (SEQ ID NO 40), CDR-L2 (SEQ ID NO 41) and CDR-L3 (SEQ ID NO 42).

In particular embodiments, the domain comprises a heavy chain variable region (Vh) or a light chain variable region (Vk) comprising:

| | | |
|---|---|---|
| a) | mu317 | (SEQ ID NOS: 4 or 6); |
| b) | mu326 | (SEQ ID NOS: 8 or 10); |
| c) | 317-4B6 | (SEQ ID NOS: 24 or 26); |
| d) | 326-4A3 | (SEQ ID NOS: 28 or 30); |
| e) | 317-4B2 | (SEQ ID NOS: 43 or 44); |
| f) | 317-4B5 | (SEQ ID NOS: 45 or 46); |
| g) | 317-1 | (SEQ ID NOS: 48 or 50); |
| h) | 326-3B1 | (SEQ ID NOS: 51 or 52); |
| i) | 326-3G1 | (SEQ ID NOS: 53 or 54); |
| j) | 326-1 | (SEQ ID NOS: 56 or 58); |

-continued

| | | |
|---|---|---|
| k) | 317-3A1 | (SEQ ID NOS: 64); |
| l) | 317-3C1 | (SEQ ID NOS: 65); |
| m) | 317-3E1 | (SEQ ID NOS: 66); |
| n) | 317-3F1 | (SEQ ID NOS: 67); |
| o) | 317-3G1 | (SEQ ID NOS: 68); |
| p) | 317-3H1 | (SEQ ID NOS: 69); |
| q) | 317-3I1 | (SEQ ID NOS: 70); |
| r) | 317-4B1 | (SEQ ID NOS: 71); |
| s) | 317-4B3 | (SEQ ID NOS: 72); |
| t) | 317-4B4 | (SEQ ID NOS: 73); |
| u) | 317-4A2 | (SEQ ID NOS: 74); |
| v) | 326-3A1 | (SEQ ID NOS: 75); |
| w) | 326-3C1 | (SEQ ID NOS: 76); |
| x) | 326-3D1 | (SEQ ID NOS: 77); |
| y) | 326-3E1 | (SEQ ID NOS: 78); |
| z) | 326-3F1 | (SEQ ID NOS: 79); |
| aa) | 326-3B N55D | (SEQ ID NOS: 80); |
| ab) | 326-4A1 or | (SEQ ID NOS: 81); |
| ac) | 326-4A2 | (SEQ ID NOS: 82). |

In particular embodiments, the domain comprises a heavy chain variable region (Vh) and a light chain variable region (Vk) comprising:

| | | |
|---|---|---|
| a) | mu317 | (SEQ ID NOS: 4 and 6); |
| b) | mu326 | (SEQ ID NOS: 8 and 10); |
| c) | 317-4B6 | (SEQ ID NOS: 24 and 26); |
| d) | 326-4A3 | (SEQ ID NOS: 28 and 30); |
| e) | 317-4B2 | (SEQ ID NOS: 43 and 44); |
| f) | 317-4B5 | (SEQ ID NOS: 45 and 46); |
| g) | 317-1 | (SEQ ID NOS: 48 and 50); |
| h) | 326-3B1 | (SEQ ID NOS: 51 and 52); |
| i) | 326-3G1 | (SEQ ID NOS: 53 and 54); |
| j) | 326-1 | (SEQ ID NOS: 56 and 58); |
| k) | 317-3A1 | (SEQ ID NOS: 64 and 26); |
| l) | 317-3C1 | (SEQ ID NOS: 65 and 26); |
| m) | 317-3E1 | (SEQ ID NOS: 66 and 26); |
| n) | 317-3F1 | (SEQ ID NOS: 67 and 26); |
| o) | 317-3G1 | (SEQ ID NOS: 68 and 26); |
| p) | 317-3H1 | (SEQ ID NOS: 69 and 26); |
| q) | 317-3I1 | (SEQ ID NOS: 70 and 26); |
| r) | 317-4B1 | (SEQ ID NOS: 71 and 26); |
| s) | 317-4B3 | (SEQ ID NOS: 72 and 26); |
| t) | 317-4B4 | (SEQ ID NOS: 73 and 26); |
| u) | 317-4A2 | (SEQ ID NOS: 74 and 26); |
| v) | 326-3A1 | (SEQ ID NOS: 75 and 30); |
| w) | 326-3C1 | (SEQ ID NOS: 76 and 30); |
| x) | 326-3D1 | (SEQ ID NOS: 77 and 30); |
| y) | 326-3E1 | (SEQ ID NOS: 78 and 30); |
| z) | 326-3F1 | (SEQ ID NOS: 79 and 30); |
| aa) | 326-3B N55D | (SEQ ID NOS: 80 and 30); |
| ab) | 326-4A1 or | (SEQ ID NOS: 28 and 81); |
| ac) | 326-4A2 | (SEQ ID NOS: 28 and 82). |

In particular embodiments, the domain specifically binds PD1 residues: (a) K45 and I93 (AA numbering based on 2008 PNAS, 105:10483; equivalent to K58 and I106 in SEQ ID NO 2); or (b) I93, L95 and P97 (AA numbering based on 2008 PNAS, 105:10483; equivalent to I106, L108 and P110 in SEQ ID NO 2).

In particular embodiments, the domain induces IL-2 release in HuT78/PD-1 cells co-cultured with HEK293/OS8/PD-L1 cells or with EK293/OS8/PD-L2 cells, and/or inhibits IL-2 secretion in HuT78/P3Z cells co-cultured with HEK293/PD-L1 cells or with HEK293/OS8/PD-L2 cells.

The invention also provides an antibody IgG4 heavy chain effector or constant domain comprising any of SEQ ID NO:83-88, particularly SEQ ID NO 87 or 88.

The invention also provides antibodies, F(ab) or F(ab)$_2$ comprising a subject PD-1 binding domain.

The invention also provides antibodies comprising a subject PD-1 binding domain and a IgG4 heavy chain effector or constant domain comprising any of SEQ ID NO:83-88, particularly SEQ ID NO 87 or 88.

The invention also provides a polynucleotide encoding a subject PD-1 binding domain, particularly cDNA sequences.

The invention provides methods of using the subject domains by administering the domain to a person determined to have cancer or a viral infection or to otherwise be in need of PD-1 antagonism.

The invention also provides fusion proteins comprising: (a) a single chain variable fragment (scFv) of an anti-human CD3 mAb OKT3 fused to the C-terminal domain (113-220) of mouse CD8α (SEQ ID NO:89); or (b) the extracellular and transmembrane domains of human PD-1 fused to the cytoplasmic domain of human CD3ζ chain (SEQ ID NO: 90).

The invention also provides methods of using the subject fusion proteins, comprising assaying, screening or selecting anti-PD-1 antibodies with a cell line expressing the fusion protein.

DESCRIPTION OF PARTICULAR EMBODIMENTS OF THE INVENTION

Figure 1:
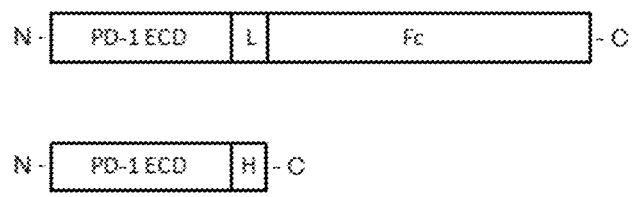
FIG. 1. Schematic presentation of PD-1/Fc (top) and PD-1/His (bottom). ECD: extracellular domain. L: linker. H: His tag. Fc: γ4Fc fragment from human IgG4. N: N-terminus C: C-terminus FIG. 2. Dose-dependent reaction curves of murine mAbs binding to human PD-1 in ELISA. The murine mAbs were indicated at top-left corner of each figure. MAb 317 and 517 share high degree of homology the variable region of heavy and light chains. The binding signal strength was indicated by direct $OD_{450}$ readings. The antigen, PD-1/His, was coated at increasing concentrations up to 70 nanograms per well in a volume of 50 microliters. The method was described in Example 1.

PD-1 initiates inhibitory signaling in immune cells when engaged by its ligands, PD-L1 or PD-L2. In the cases of cancer outgrowth and viral infection, the activation of PD-1 signaling promotes immune tolerance, leading to the cancers or virus-infected cells escaping from immune surveillance and cancer metastasis or viral load increase Inhibition of PD-1 mediated cellular signaling by therapeutic agents can activate immune cells including T-cells, B-cells and NK cells, and therefore enhance immune cell functions inhibiting cancer cell growth or viral infection, and restore immune surveillance and immune memory function to treat such human diseases.

The invention provides antibodies whose functions are antagonistic to the ligand-induced and PD-1-mediated cellular signaling in immune cells. Murine anti-PD-1 antibodies were humanized to a high degree of similarity to human antibodies in the framework regions. The full antibodies made in the modified human IgG4 variant format have a unique set of features in the aspects of effector functions and physicochemical properties. The disclosed anti-PD-1 antibodies are suitable for therapeutic uses in cancer treatment, controlling viral infections and other human diseases that are mechanistically involved in exacerbated immune tolerance.

DEFINITIONS

Unless the context indicates otherwise, the term "antibody" is used in the broadest sense and specifically covers antibodies (including full length monoclonal antibodies) and antibody fragments so long as they recognize PD-1. An antibody molecule is usually monospecific, but may also be described as idiospecific, heterospecific, or polyspecific. Antibody molecules bind by means of specific binding sites to specific antigenic determinants or epitopes on antigens.

"Antibody fragments" comprise a portion of a full length antibody, generally the antigen binding or variable region thereof. Examples of antibody fragments include Fab, Fab', F(ab').sub.2, and Fv fragments; diabodies; linear antibodies; single-chain antibody molecules; and multispecific antibodies formed from antibody fragments.

Natural and engineered antibody structures are well known in the art, e.g. Strohl et al., *Therapeutic antibody engineering: Current and future advances driving the strongest growth area in the pharmaceutical industry*, Woodhead Publishing Series in Biomedicine No. 11, October 2012; Holliger et al. Nature Biotechnol 23, 1126-1136 (2005); Chames et al. Br J Pharmacol. 2009 May; 157(2): 220-233.

Monoclonal antibodies (MAbs) may be obtained by methods known to those skilled in the art. See, for example Kohler et al (1975); U.S. Pat. No. 4,376,110; Ausubel et al (1987-1999); Harlow et al (1988); and Colligan et al (1993). The mAbs of the invention may be of any immunoglobulin class including IgG, IgM, IgE, IgA, and any subclass thereof. A hybridoma producing a mAb may be cultivated in vitro or in vivo. High titers of mAbs can be obtained in in vivo production where cells from the individual hybridomas are injected intraperitoneally into mice, such as pristine-primed Balb/c mice to produce ascites fluid containing high concentrations of the desired mAbs. MAbs of isotype IgM or IgG may be purified from such ascites fluids, or from culture supernatants, using column chromatography methods well known to those of skill in the art.

An "isolated polynucleotide" refers to a polynucleotide segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, which is part of a hybrid gene encoding additional polypeptide sequence.

A "construct" means any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e. operably linked. A recombinant construct will typically comprise the polynucleotides of the invention operably linked to transcriptional initiation regulatory sequences that will direct the transcription of the polynucleotide in the intended host cell. Both heterologous and non-heterologous (i.e., endogenous) promoters can be employed to direct expression of the nucleic acids of the invention.

A "vector" refers any recombinant polynucleotide construct that may be used for the purpose of transformation, i.e. the introduction of heterologous DNA into a host cell. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors".

An "expression vector" as used herein refers to a nucleic acid molecule capable of replication and expressing a gene of interest when transformed, transfected or transduced into a host cell. The expression vectors comprise one or more phenotypic selectable markers and an origin of replication to ensure maintenance of the vector and to, if desired, provide amplification within the host. The expression vector further comprises a promoter to drive the expression of the polypeptide within the cells. Suitable expression vectors may be plasmids derived, for example, from pBR322 or various pUC plasmids, which are commercially available. Other expression vectors may be derived from bacteriophage, phagemid, or cosmid expression vectors.

ADDITIONAL EMBODIMENTS OF THE INVENTION

In specific embodiments the invention provides mouse monoclonal antibodies identified from screening murine hybridoma clones as disclosed herein.

In other embodiments the invention provides compositions of the following polynucleotide and protein sequences:
 a) The cDNA sequence, SEQ ID NO 3, encoding the heavy chain variable region of murine mAb 317;
 b) The protein sequence of the heavy chain variable region of murine mAb 317 or mu317_Vh (SEQ ID NO 4);
 c) The cDNA sequence, SEQ ID NO 5, encoding the light chain variable region of murine mAb 317;
 d) The protein sequence of the light chain variable region of murine mAb 317 or mu317_Vk (SEQ ID NO 6);
 e) The cDNA sequence, SEQ ID NO 7, encoding the heavy chain variable region of murine mAb 326;
 f) The protein sequence of the heavy chain variable region of murine mAb 326 or mu326_Vh (SEQ ID NO 8);
 g) The cDNA sequence, SEQ ID NO 9, encoding the light chain variable region of murine mAb 326;
 h) The protein sequence of the light chain variable region of murine mAb 326 or mu326_Vk (SEQ ID NO 10).

In one aspect, the invention provides compositions comprising complement determinant region (CDR) sequences, which mediate binding to the target antigens, PD-1, including the CDR sequences of mu317 and m326:
 a) The CDR1 of mu317 heavy chain (mu317 H-CDR1) contains amino acid sequence of GFSLTSYGVH (SEQ ID NO 11);
 b) The mu317 H-CDR2 contains amino acid sequence of VIWAGGSTNYNSALMS (SEQ ID NO 12);
 c) The mu317 H-CDR3 contains amino acid sequence of ARAYGNYWYIDV (SEQ ID NO 13);
 d) The CDR1 of mu317 light chain (mu317 L-CDR1) contains amino acid sequence of KASQSVSNDVA (SEQ ID NO 14);
 e) The mu317 L-CDR2 contains amino acid sequence of YAFHRFT (SEQ ID NO 15);
 f) The mu317 L-CDR3 contains amino acid sequence of HQAYSSPYT (SEQ NO 16);
 g) The mu326 H-CDR1 contains amino acid sequence of GYTFTNYGMN (SEQ ID NO 17);
 h) The mu326 H-CDR2 contains amino acid sequence of WINNNNGEPTYAEEFKG (SEQ ID NO 18);
 i) The mu326 H-CDR3 contains amino acid sequence of ARDVMDY (SEQ ID NO 19);
 j) The mu326 L-CDR1 contains amino acid sequence of RASESVDNYGYSFMH (SEQ ID NO 20);
 k) The mu326 L-CDR2 contains amino acid sequence of RASNLES (SEQ ID NO 21);
 l) The mu326 L-CDR3 contains amino acid sequence of QQSKEYPT (SEQ ID NO 22).

In another embodiment, the invention provides compositions comprising the sequences of the humanization monoclonal antibodies emanated from murine mAbs mu317 and mu326, including:
 a) The humanization mAb hu317-4B6 comprises protein sequence of heavy chain variable region (Vh) as SEQ ID NO 24, which is encoded by
 b) the cDNA of hu317-4B6_Vh (SEQ ID NO 23);
 c) The humanization mAb hu317-4B6 also comprises protein sequence of light chain variable region (Vk) as SEQ ID NO 26, which is encoded by
 d) the cDNA of hu317-4B6 (SEQ ID NO 25);
 e) the humanization mAb hu326-4A3 comprises protein sequence of Vh as SEQ ID NO 28, which is encoded by
 f) the cDNA of hu326-4A3-Vh (SEQ ID NO 27);
 g) The humanization mAb hu326-4A3 also comprises protein sequence of Vk as SEQ ID NO 30, which is encoded by
 h) the cDNA of hu326-4A3_Vk (SEQ ID NO 29);
 i) The protein sequences of hu317-4B2_Vh (SEQ ID NO 43) and hu317-4B2_Vk (SEQ ID NO 44);
 j) The protein sequences of hu317-4B5_Vh (SEQ ID NO 45) and hu317-4B5_Vk (SEQ ID NO 46);
 k) The protein sequence of hu317-1_Vh (SEQ ID NO 48) and the cDNA encoding for hu317-1_Vh (SEQ ID NO 47);
 l) The protein sequence of hu317-1_Vk (SEQ ID NO 50) and the cDNA encoding for hu317-1_Vk (SEQ ID NO 49);
 m) The protein sequences of hu326-3B1_Vh (SEQ ID NO 51) and hu326-3B1_Vk (SEQ ID NO 52);
 n) The protein sequences of hu326-3G1_Vh (SEQ ID NO 53) and hu326-3G1_Vk (SEQ ID NO 54);
 o) The protein sequence of hu326-1_Vh (SEQ ID NO 56) and the cDNA encoding for hu326-1_Vh (SEQ ID NO 55);
 p) The protein sequence of hu326-1_Vk (SEQ ID NO 58) and the cDNA encoding for hu326-1_Vk (SEQ ID NO 57);
 q) The protein sequences of other humanization mAbs emanated from mu317 (SEQ ID NO 63-74);
 r) The protein sequences of other humanization mAbs emanated from mu326 (SEQ ID NO 75-82);

In one aspect, the invention provides compositions comprising the CDR sequences of the humanization monoclonal antibodies. The CDRs may be shared among the same series of humanization mAbs, such as hu317 or hu326 (see Table 15-16). Non-redundant CDRs are listed below:
 a) H-CDR1 sequence of GFSLTSYGVH (SEQ ID NO 31), shared throughout humanization mAbs hu317 and mu317 in the heavy chains;
 b) H-CDR3 sequence of ARAYGNYWYIDV (SEQ ID NO 33), shared throughout humanization mAbs hu317 and mu317 in the heavy chains;
 c) L-CDR1 sequence of KSSESVSNDVA (SEQ ID NO 34), shared throughout humanization mAbs hu317-4B2, hu317-4B5 and hu317-4B6 in the light chains;
 d) L-CDR2 sequence of YAFHRFT (SEQ ID NO 35), shared throughout humanization mAbs hu317 and mu317 in the light chains;

e) L-CDR3 sequence of HQAYSSPYT (SEQ ID NO 36), shared throughout humanization mAbs hu317 and mu317 in the light chains;

f) H-CDR2 sequence of VIYADGSTNYNPSLKS (SEQ ID NO 32) in hu317-4B6_Vh;

g) H-CDR2 sequence of VIYAGGSTNYNPSLKS (SEQ ID NO 60) in hu317-4B2_Vh and hu317-4B5_Vh;

h) H-CDR2 sequence of VIWAGGSTNYNPSLKS (SEQ ID NO 59) in hu317-1_Vh;

i) L-CDR1 sequence of KASQSVSNDVA (SEQ ID NO 11) in hu317-1_Vk;

j) H-CDR1 sequence of GYTFTNYGMN (SEQ ID NO 37), shared throughout humanization mAbs hu326 and mu326 in the heavy chains;

k) H-CDR3 sequence of ARDVMDY (SEQ ID NO 39), shared throughout humanization mAbs hu326 and mu326 in the heavy chains;

l) L-CDR1 sequence of RASESVDNYGYSFMH (SEQ ID NO 40), shared throughout humanization mAbs hu326 and mu326 in the light chains;

m) L-CDR2 sequence of RASNLES (SEQ ID NO 41), shared throughout humanization mAbs hu326 and mu326 in the light chains;

n) L-CDR3 sequence of QQSKEYPT (SEQ ID NO 42), shared throughout humanization mAbs hu326 and mu326 in the light chains;

o) H-CDR2 sequence of WINNNNAEPTYAQDFRG (SEQ ID NO 38) in hu326_4A3_Vh;

p) H-CDR2 sequence of WINNNNGEPTYAQGFRG (SEQ ID NO 62) in the Vh of hu326_1 and other hu317 mAbs.

In another aspect, the invention provides particular binding epitopes of the humanized anti-PD-1 mAbs on the antigen, and functional use thereof. Six critical amino acid (AA) residues in PD-1 required for the ligand binding were mutated individually, and mutant and wild-type PD-1 proteins were used to assess the binding epitopes. The residue whose mutation significantly impaired the antibody binding is recognized as a key or significant binding epitope. Significant binding epitopes of mAbs hu317-4B5 and hu317-4B6 are K45 and I93 (AA numbering based on 2008 PNAS, 105:10483; equivalent to K58 and I106 in SEQ ID NO 2); and significant binding epitopes of mAbs hu326-3B1 and hu317-4A3 are I93, L95 and P97 (AA numbering based on 2008 PNAS, 105:10483; equivalent to I106, L108 and P110 in SEQ ID NO 2).

In a further aspect, the invention provides compositions comprising the constant region sequences of recombinant human IgG4 variants, which may be linked to the variable regions of the subject antibodies, including the humanized anti-PD-1 mAbs, which showed preferred effector functions and physicochemical properties. The sequences are as follows:

The constant region sequence of IgG4mt10 (SEQ ID NO 88);

a) A reference sequence of IgG4mt1 (SEQ ID NO 83);
b) A reference sequence of IgG4mt2 (SEQ ID NO 84);
c) A reference sequence of IgG4mt6 (SEQ ID NO 85);
d) A reference sequence of IgG4mt8 (SEQ ID NO 86);
e) A reference sequence of IgG4mt9 (SEQ ID NO 87).

In another embodiment, the invention provides methods for assaying anti-PD-1 antibody functions, using a plasmid expressing the recombinant fusion protein, OS8, to generate stable cell lines, HEK293/OS8/PD-L1 or HEK293/OS8/PD-L2, which co-expresses OS8 (a T cell-activating molecule) and a PD-1 ligand. The cell lines were used to engage T-cells and PBMCs by co-culture to assess the functionality of anti-PD-1 mAbs (see Example 3 and Example 4). Alternatively, another plasmid expressing the recombinant fusion protein, P3Z, was used to generate stable cell line, HuT78/P3Z, in which P3Z functions as molecular sensor and signal transduction mediator. When P3Z is engaged by PD-1 ligand, it will transmit intracellular signal to activate IL-2 release in the HuT78 cells. The systems may be used to assess inhibitory effect of anti-PD-1 mAbs (see Example 3).

In one aspect, the invention provides compositions comprising the amino acid sequences of the recombinant fusion proteins as follows:

a) Protein sequence of OS8 (SEQ ID NO 89);
b) Protein sequence of P3Z (SEQ ID NO 90).

In another aspect, the invention provides methods of generating the stable cell lines that express the recombinant fusion proteins described herein, and methods of using the system to quantitatively assay the functional activities of anti-PD-1 mAbs.

In another embodiment the invention provides polynucleotides encoding the subject proteins. The polynucleotides may be operably linked to a heterologous transcription regulating sequence for expression, and may be incorporated into vectors, cells, etc.

In another embodiment, the invention provides the murine anti-PD-1 antibodies and humanized version anti-PD-1 antibodies, including hu317-4B6, hu317-4B5, hu317-4B2, etc., and hu326-4A3, hu326-3B1, hu326-3G1, etc., having functions to suppress PD-1 mediated signal transduction, and to activate immune cells, which trigger a cascade of immune responses including cytokine secretion and cytotoxicity towards target cells such as cancer cells, and such functional use of the antibodies.

In one aspect, the invention provides humanized anti-PD-1 antibodies that activate several types of immune cells that express PD-1, including human T-cells, NK-cells and PBMCs, whose functions are to amplify the immune response signals, to mobilize immune system and to act as immune effector cells for clearance of cancer cells and viral infections, and such functional use of the antibodies.

In another aspect, the humanized anti-PD-1 mAbs are used as therapeutic agents to treat human diseases that are involved in suppression of immune cells by PD-1 mediated intracellular signaling, leading to disease progression, particularly cancers and viral infections.

The compositions of the invention are useful for the treatment of cancer, neurodegenerative and infectious, particularly viral, diseases and other conditions in which inappropriate or detrimental expression of the human PD-1 and/or is a component of the etiology or pathology of the condition. Hence, the invention provides methods for treating cancer or inhibiting tumor progression in a subject in need thereof with a subject anti-PD-1 protein. The invention further provides the use of subject polynucleotides for the manufacture of a medicament for treating cancer or inhibiting tumor progression in a subject.

The invention includes all combinations of the recited particular embodiments. Further embodiments and the full scope of applicability of the invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. All publications, patents, and patent applications cited herein, including citations therein, are hereby incorporated by reference in their entirety for all purposes.

EXAMPLES

Example 1

Generation of Anti-PD-1 Monoclonal Antibody

Anti-PD-1 monoclonal antibodies (mAbs) were generated based on conventional hybridoma fusion technology (Kohler and Milstein 1976 Eur J Immunol 6:511-519; de St Groth and Sheidegger 1980, J Immunol Methods 35:1-21; Mechetner 2007 Methods Mol Biol 378:1-13) with minor modifications. MAbs with high binding activities in enzyme-linked immunosorbent assay (ELISA) and fluorescence-activated cell sorting (FACS) assay were selected for further characterization PD-1 Recombinant Protein for Immunization and Binding Assays Expression plasmid containing full-length human PD-1 cDNA was obtained from Origene (Cat. No. SC117011, NCBI Accession No: NM_005018.1, Beijing, China). The extracellular domain consisting of amino acid (AA) 1-168 of PD-1 (SEQ N0.1, SEQ N0.2) was PCR-amplified, and subcloned in pcDNA3.1-based expression vector (Invitrogen, Carlsbad, Calif., USA) with C-terminus fused either to a $His_6$ tag or to the γFc domain of human IgG4 heavy chain, which resulted in two recombinant fusion protein expression plasmids, PD-1-EC/His and PD-1-EC/Fc (abbreviated as PD-1/His and PD-1/Fc). The schematic presentation of immunogen/antigen proteins were shown in FIG. 1. For the recombinant fusion protein production, PD-1/His and PD-1/Fc plasmids were transiently transfected into 293-F cells in 1-3 liters of medium (Invitrogen), and cultured for 5-7 days in a $CO_2$ incubator equipped with rotating shaker. The supernatant containing the recombinant protein was collected and cleared by centrifugation at 15000 g for 30 minutes. PD-1/His was purified through immobilized metal affinity chromatography using Ni-Sepharose Fast Flow (Cat. No. 17531801, GE Lifesciences, Shanghai, China), followed by size exclusion chromatography using a HiLoad 16/60 Superdex 200 column (Cat. No. 17106901, GE Lifesciences, Shanghai, China). PD-1/Fc was purified using a Protein G Sepharose Fast Flow column (Cat. No. 17061805, GE Lifesciences). Both PD-1/His and PD-1/Fc proteins were dialyzed against phosphate buffered saline (PBS) and stored in −80° C. freezer in small aliquots.

The cDNA coding for human PD-L1 was chemically synthesized by Genescript (Nanjing, China) based on the published sequence (NCBI Accession No. NM_014143). The PD-L2 expression plasmid was purchased from Origene (Cat. No. SC108873, NCBI Accession No. NM_025239.2, Beijing, China). Both cDNAs were cloned in pcDNA3.1/Hygromycin (Cat. No. V870-20, Invitrogen), and pcDNA3.1/V5-His (Cat. No. V810-20, Invitrogen), respectively.

Stable Expression Cell Line

Stable cell lines expressing human PD-1, PD-L1 or PD-L2 were established by transfection of pcDNA3.1 plasmids containing PD-1, PD-L1 and PD-L2 to HUT78 (ATCC, Manassas, Va., USA) and HEK293 (ATCC), respectively, and followed by selection with medium containing 200 micrograms of hygromycin (Cat. No. 10687-010, Invitrogen) or 1 mg of G418 (Sigma) per milliliter. Single clones were isolated by conventional method, either limited dilution or picking up single colonies from culture-well surface. All clones were screened by Western blot and FACS analysis using anti-PD-1, PD-L1 and PD-L2 antibodies (Cat. No. 12-9969, 17-5983, 12-5888, eBioscience, San Diego, USA), respectively, and the top expression clones were selected for FACS binding assay to screen hybridoma monoclonal antibodies, or used in functional assays.

Immunization, Hybridoma Fusion and Cloning

Eight to twelve week-old Balb/c mice (from BEIJING HFK BIOCSIENCE CO., LTD, Beijing, China) were immunized subcutaneously with 100 ul of adjuvant (Cat. No. KX0210041, KangBiQuan, Beijing, China) containing 5 micrograms of PD-1/Fc. The immunization was conducted by two injections of the above immunogen with three weeks apart. Two weeks after the 2nd immunization, the mice sera were evaluated for PD-1 binding by FACS (following sections). The mice with high anti-PD-1 antibody titers in sera were selected and boosted intraperitoneally with 50 micrograms of PD-1/Fc in the absence of any adjuvant. Three days after boosting, the splenocytes were isolated and fused with the murine myeloma cell line, SP2/0 cells (ATCC), using standard techniques (Gefter, M. L. et al., 1977 Somat Cell Genet, 3:231-236).

Assess PD-1 Binding Activity of Antibodies by ELISA and FACS

The supernatants of hybridoma clones were initially screened by Enzyme-Linked Immuno-Sorbent Assay (ELISA) as described in "Flanagan, M. L. et al. 2007 Methods in Molecular Biology 378:33-52" with some modifications. Briefly, 50-200 nanograms of PD-1/His or PD-1/Fc protein in 50 microliters of phosphate buffered saline (PBS) were coated in 96-well plate (Shenzhen JinCanHua Industry Co., Ltd, Shenzhen, China) on per well base. The HRP-linked anti-mouse IgG antibody (Cat. No. 7076S, Cell Signaling Technology, USA and Shanghai, China) and chemiluminescent reagent (Cat. No. PA107-01, TIANGEN, China) were used to detect and develop the ELISA signal, which were read out by a plate reader (PHREAstar FS, BMG LABTECH, Germany) at wavelength of 450 nm The ELISA-positive antibody producer clones were further verified by fluorescence-activated cell sorting (FACS) using a conventional method. PD-1 stable expression cell lines, HuT78/PD-1 ($10^5$ cells/well), described above, was stained with supernatants from anti-PD-1 hybridomas in V-bottom 96-well plates (Cat. No. 3897, Corning, USA and Shanghai, China). To block human Fc receptors, cells were pre-incubated with human IgG (20 μg/ml) (Cat. No. H11296, LifeHolder, USA and Shanghai, China). PD-1 antibodies were detected with Dylight™ 649-labelled goat anti-mouse IgG antibody (Cat. No. 405312, Biolegend, San Diego, USA) and cell fluorescence was monitored using a flow cytometer (Guava easyCyte 8HT, Merck-Millipore, USA and Shanghai, China).

The conditioned media of hybridoma cells that showed positive signal in both ELISA and FACS assay were subjected to functional assays to identify antibodies with good functional activity in human immune cell-based assays (herein). The antibodies with positive functional activity were further subcloned and characterized.

Subcloning and Adaptation to Serum Free or Low Serum Medium

The positive hybridoma clones from primary screening through ELISA, FACS and functional assays were subcloned by the conventional method of limited dilution. Each of the positive clones was plated out in a 96-well plate, cultured in RPMI1640 medium (Cat. No. SH30809.01B, Hyclone, Shanghai, China) with 10% fetal bovine serum (FBS, Cat. No. SH30084.03, Hyclone, Beijing, China) in $CO_2$ incubator. Three subclones from each limited dilution plate were selected and characterized by FACS and functional assays. The subclones selected through functional assays were defined as monoclonal antibody. The top subclones were adapted for growth in the CDM4MAb medium (Cat. No. SH30801.02, Hyclone) with 1-3% FBS.

Expression and Purification of Monoclonal Antibodies

Either murine monoclonal antibody-producing hybridoma cells or recombinant antibody plasmids-transfected 293-F cells (Cat. No. R79007, Invitrogen) were cultured in CDM4MAb medium (Cat. No. SH30801.02, Hyclone) or Freestyle293 Expression medium (Cat. No. 12338018, Invitrogen), respectively, in a $CO_2$ incubator at 37° C. for 5 to 7 days. The conditioned medium was collected through centrifugation at 10,000 g for 30 minutes to remove all cells and cell debris, and filtrated through a 0.22 μm membrane before purification. Murine or recombinant antibodies were applied and bound to a Protein A column (Cat. No. 17127901, GE Life Sciences) following the manufacturer's guidance, washed with PBS, eluted in the buffer containing 20 mM citrate, 150 mM NaCl, pH3.5. The eluted materials were neutralized with 1M Tris pH8.0, and usually contained antibodies of above 90% purity. The Protein A-affinity purified antibodies were either dialyzed against PBS or further purified using a HiLoad 16/60 Superdex200 column (Cat. No. 17531801, GE Life Sciences) to remove aggregates. Protein concentrations were determined by measuring absorbance at 280 nm or by Bradford assay (Cat. No. 1856210, Thermo Scientific, Rockford, Ill., USA) using bovine IgG of defined concentration (Cat. No. 23212, Thermo Scientific) as the standards. The purified antibodies were stored in aliquots in −80° C. freezer.

Example 2

Comparison of Binding Activities Among Anti-PD-1 Antibodies

Figure 2:
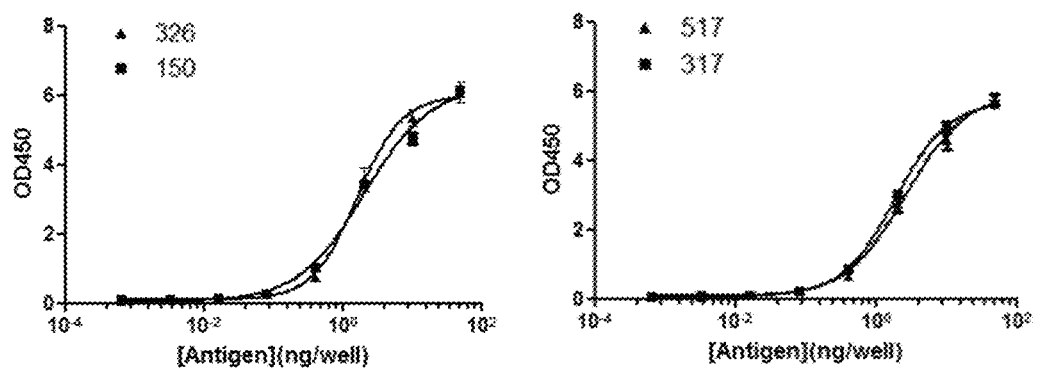
Figure 3:
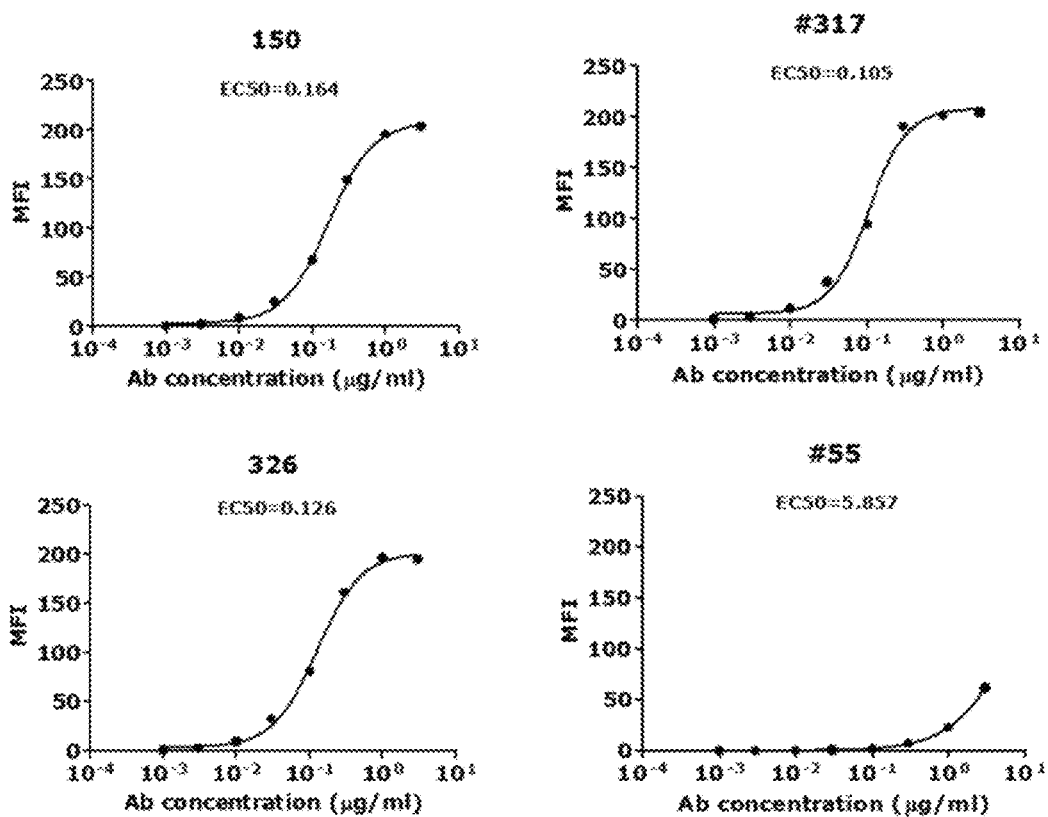
FIG. 3. Dose-dependent reaction curve of murine mAbs binding to human PD-1 expressed on live cells by FACS analyses. Murine antibody codes and $EC_{50}$ were indicated on each panel. MFI stands for mean fluorescence intensity. HuT78/PD-1 cells were suspended in 96-well plate at $5 \times 10^4$ cells per well for FACS. PD-1 mAbs binding to the cell surface target and FACS detection were performed as described in Example 1.

Through screening thousands of hybridomal clones we identified some top monoclonal antibodies (mAb), which bind to human PD-1 with high specificity and strength. As shown in ELISA assay (FIG. 2), three of the top antibodies elicited such binding strength and specificity. FACS analysis results demonstrated the selected monoclonal antibodies bind to the native PD-1 proteins expressed on cell surface. Murine mAb317 (mu317), mu326 and mu150 showed concentration-dependent binding activity, and their binding $EC_{50}$ (Effective concentration at 50% activity) was significantly lower than that of the control mu55 (FIG. 3).

Assess mAb Binding Affinity by Surface Plasmon Resonance (SPR)

The mAbs with high binding activities in ELISA and FACS, as well as with potent functional activities in the cell-based assays (herein) were examined for their binding kinetic constant in real time binding reactions. Murine anti-PD-1 mAbs were purified from hybridoma supernatants using protein A Flow column (Cat. No. 17531801, GE Life Sciences) followed by exclusion chromatography using a HiLoad 16/60 Superdex200 column (Cat. No. 17106901, GE Life Sciences). The purified anti-PD-1 antibodies were concentrated to 0.5-1 mg/mL in PBS and stored in aliquots in −80° C. freezer.

For determining binding affinities of PD-1 mAbs, SPR measurements were performed in HBS-N buffer (10 mM HEPES pH 7.4, 0.15 M NaCl, 3 mM EDTA, 0.005% v/v surfactant P20, GE Healthcare) using the BIAcore™ T-200 instrument (GE Life Sciences). Anti-mouse Fc CM5 biosensor chip (GE Healthcare) was generated using a standard primary amine coupling protocol. PD-1 mAbs at 0.3 μg/ml were captured on anti-mouse Fc surface for 1 min at 10 μl/min PD-1/Fc in a serial dilutions from 3.3 nM to 120 nM was injected over antibody-bound surface for 3 min at 30 μl/min followed by a 10 mM dissociation phase. Association rates ($K_a$ or $k_{on}$) and dissociation rates ($K_d$ or $k_{off}$) were calculated using the one-to-one Langmuir binding model (BIA Evaluation Software, GE Life Sciences). The equilibrium dissociation constant ($K_D$) was calculated as the ratio $k_{off}/k_{on}$.

As shown in Table 1, both mu326 and mu517, a cognate sequence family member related to mu317, have a sub-nanomolar $K_D$ equaling to 0.324 nM and 0.289 nM, respectively, which is significantly better than that of mu134. The $K_{on}$ rate was similar among the three mAbs listed in Table 1, yet the $K_{off}$ rate was significantly different, much faster dissociation rate was observed in mu134.

TABLE 1

Binding constant of certain top antibodies

| mAbs | $K_{on}$ (M$^{-1}$, s$^{-1}$) | $K_{off}$ (s) | $K_D$ (M) |
|---|---|---|---|
| mu326 | $2.4 \times 10^5$ | $7.79 \times 10^{-5}$ | $3.24 \times 10^{-10}$ |
| mu517 | $1.96 \times 10^5$ | $5.66 \times 10^{-5}$ | $2.89 \times 10^{-10}$ |
| mu134 | $1.1 \times 10^5$ | $3.69 \times 10^{-4}$ | $3.35 \times 10^{-9}$ |

Affinity Determination of Anti-PD-1 Fabs by SPR

Anti-PD-1 mAbs were converted into Fab version by PCR to fuse the variable regions of heavy and light chains to the N-terminus of human IgG2-CH1 and constant region of kappa chain, respectively, and subcloned in pcDNA3.1 vector (Invitrogen). Both expression vectors were co-expressed in 293-F cells using a transient transfection protocol similar to the transient expression of whole antibodies. Briefly, the Fab kappa chain was PCR amplified and subcloned in pcDNA3.1-based expression vector (Invitrogen, Carlsbad, Calif., USA). In a separate plasmid, the heavy chain variable region (VH) together with the CH1 coding sequence from human IgG2 was fused with a C-terminal c-Myc-His8 tag by overlapping PCR, and then subcloned in the expression vector. The C232S and C233S (Kabat residue numbering, Kabat et al. Sequence of proteins of immunologic interest, 5$^{th}$ ed Bethesda, Md., NIH 1991) mutations were introduced in the IgG2 heavy chain to prevent disulfide bond exchange and stabilize human IgG2 in the IgG2-A conformation (Lightle et al. 2010 Protein Sci 19(4): 753-762). Both constructs contained a signal peptide upstream of the Fab mature sequences. Secreted expression of Fab was achieved by co-transfection of above 2 plasmids into 293-F cells and cell culture supernatants were harvested 6-7 days post transfection. His8-tagged Fabs were purified from cell culture supernatants using a Ni-sepharose Fast Flow column (Cat. No. 17531801, GE Life Sciences) followed by size exclusion chromatography using a HiLoad 16/60 Superdex200 column (Cat. No. 17106901, GE Life Sciences). The purified Fabs were concentrated to 0.5-5 mg/mL in PBS and stored in aliquots in −80° C. freezer.

For affinity determinations of anti-PD-1 Fabs, SPR assays were used with the BIAcore™ T-200 instrument (GE Life Sciences). Briefly, human PD-1/His or cynomolgus monkey PD-1/His was coupled to activated CM5 biosensor chips (Cat. No. BR100530, GE Life Sciences) to achieve approximately 100-200 response units (RU), followed by blocking un-reacted groups with 1M ethanolamine Fab samples of increasing concentration from 0.12 nM to 90 nM were injected in the SPR running buffer (10 mM HEPES, 150 mM NaCl, 0.05% Tween20, pH7.4) at 30 μL/minute, and binding responses on human PD-1/His or monkey PD-1/His were calculated by substracting of RU from a blank flow-cell. Association rates ($k_{on}$) and dissociation rates ($k_{off}$) were calculated using the one-to-one Langmuir binding model (BIA Evaluation Software, GE Life Sciences). The equilibrium dissociation constant ($K_d$) was calculated as the ratio $k_{off}/k_{on}$.

The SPR-determined binding affinities of anti-PD-1 Fabs were listed in Table 18. Each anti-PD-1 Fab bound with high affinity ($K_d$=0.15-1 nM) to human PD-1. All Fabs, except 326-3G1, bound with slightly lower but comparable (within 5 fold in $K_d$) affinities to cynomolgus monkey PD-1.

Example 3

Functional Activity of Anti-PD-1 Antibodies in Human T Cells

Generation of Stable Cell Lines

Retroviral packaging cell line PT67, human T cell lines HuT78 and HEK293 were obtained from the American Type Culture Collection (ATCC, Rockville, Md.). A HuT78 subline HuT78/PD-1 that expresses PD-1 was generated by retroviral transduction using pFB-neo vector (Strategene/Agilent Tech, Santa Clara, Calif.) containing the PD-1 gene, according to the protocol described previously (Zhang et al. 2005 Blood 106: 1544-1551). The T cell engager, a membrane-anchored chimeric Ab (OS8), was constructed by fusing the single chain variable fragment (scFv) of an anti-human CD3 mAb OKT3 (Kipriyanov et al. 1997, PEDS 10:445-453) to the C-terminal domain (113-220) of mouse CD8α (NCBI Accession No: NP_001074579.1) which includes hinge, transmembrane and cytoplasmic domains. By doing so, anti-CD3 scFv is anchored to cell surface as a T cell activator. Human PD-L1, PD-L2 and OS8 cDNAs were subcloned into pcDNA3.1 vector. Stable cell lines HEK293/OS8/PD-L1, Hep3B/OS8/PD-L1 and HEK293/OS8/PD-L2 that co-express both OS8 and PD-L1 or PD-L2 cDNAs were generated by co-transfection of HEK293 and Hep3B cells (ATCC) with the paired plasmids, followed by hygromycin or G418 selection for 10-14 days. Cell lines were then cloned by limiting dilution as described previously (Fuller S A, et al. Curr Protoc Mol Biol. Chapter 11:Unit 11.8., 2001) Chimeric PD-1 receptor, named P3Z, was constructed by fusing the extracellular and transmembrane domains) of human PD-1 to the cytoplasmic domain of human CD3ζ chain (NCBI Accession No. NP_932170.1). P3Z-coding cDNA sequence was cloned into pFB-neo and delivered into HuT78 cells via retroviral transduction to generate HuT78/P3Z cells.

Determination of PD-1 Antibody Functions by IL-2 Release in HuT78/PD-1 Cells

Figure 4:
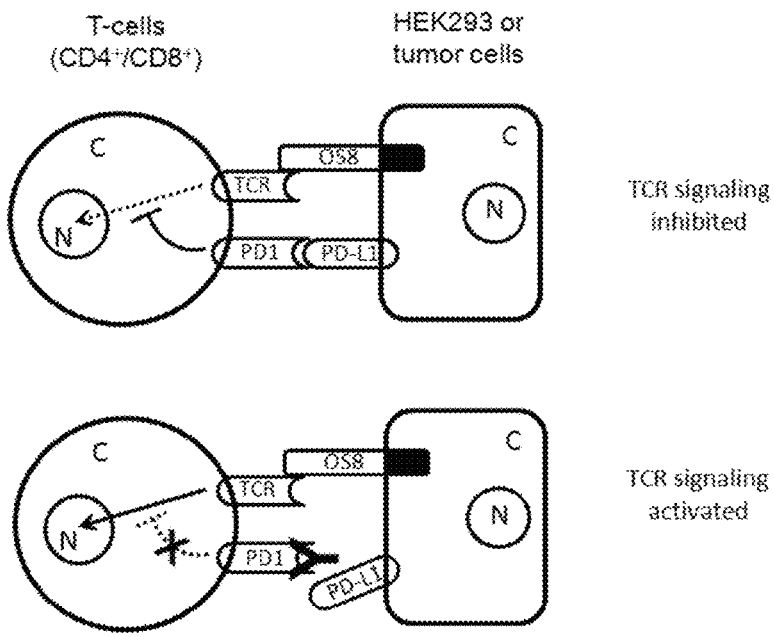
FIG. 4. Schematic presentation of the cell co-culture systems used for assaying functional activities of anti-PD-1 mAbs. T-cells (either CD4$^+$ or CD8$^+$) represent HuT78/PD-1 or primary T-cells in PBMCs. TCR: T-cell receptor. N: nucleus. C: cytoplasm FIG. 5. Dose-dependent reaction curve of murine mAb-induced IL-2 secretion in HuT78/PD-1 cells co-cultured with HEK293/OS8/PD-L1 cells. Baseline: Average IL-2 release induced by mIgGs at all tested concentrations. Top line: Highest IL-2 release based on regression calculation by Prizm Software.

To determine whether anti-PD-1 antibodies can block the interaction of PD-L1-induced PD-1 signaling, HuT78/PD-1 cells ($1.5 \times 10^4$ cells per well in 96-well plate) were pre-incubated with hybridoma supernatants or PD-1 antibodies for 15 minutes prior to co-culture with HEK293/OS8/PD-L1 or HEK293/OS8/PD-L2 cells ($4 \times 10^4$ per well) in a flat bottom plate fed with 200 nl of RPMI1640 growth medium per well at 37° C. After 16-18 hours, supernatants of the co-culture were collected. IL-2 was assayed by ELISA using human IL-2 Ready-Set-Go! ELISA kits (Cat. No. 88-7025, eBiosciences, San Diego, Calif.). In this assay, blockade of PD-1 signaling with anti-PD-1 antibodies resulted in enhanced TCR signaling and IL-2 production (FIG. 4).

Figure 5:
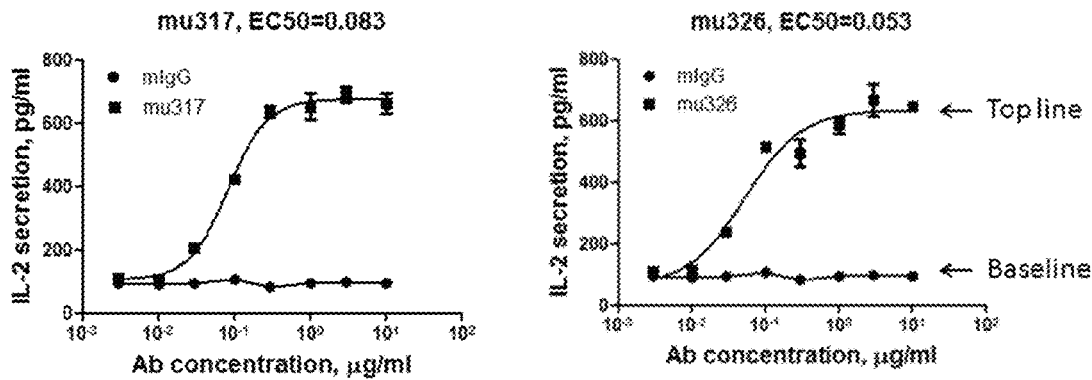

As shown in FIG. 5 and Table 2, murine anti-PD-1 mAb, mu317 and mu326, elicited significantly higher functional activity than mu30, inhibiting PD-L1-induced PD-1 signaling which leads to increased IL-2 secretion. Both had higher IL-2 secretion (top line, Table 2), 675 and 634 pg/ml, respectively, and both had lower $EC_{50}$ (Effective concentration of mAb at 50% level of IL-2 secretion induction) than mu30 antibody.

TABLE 2

IL-2 release induced by anti-PD-1 mAbs in HuT78/PD-1 cells co-cultured with HEK293/OS8/PD-L1 cells

| Antibody | Baseline (pg/ml) | Top line (pg/ml) | $EC_{50}$ (μg/ml) |
| --- | --- | --- | --- |
| mu30 | 95 | 527 | 0.229 |
| mu317 | 95 | 675 | 0.083 |
| mu326 | 95 | 634 | 0.053 |
| mIgGs | 95 | N/A | N/A |

Baseline Average IL-2 release induced by mIgGs at all tested concentrations, see Fig. 4.
Top line Highest IL-2 release based on regression calculation by Prizm Software, Fig. 4.
N/A Not applicable Not only did the engagement of HuT78/PD-1 cells by anti-PD-1 mAbs block PD-L1 induced T-cell activation, but also blocked PD-L2 induced IL-2 release. Table 3 presented the data showing mu317 and mu326 had much higher potency in activating the T-cells as indicated by the parameters ($EC_{50}$) of IL-2 secretion than those of mu476.

TABLE 3

IL-2 release induced by anti-PD-1 mAbs in HuT78/PD-1 cells co-cultured with HEK293/OS8/PD-L2 cells

| Antibody | Baseline (pg/ml) | Top line (pg/ml) | $EC_{50}$ (μg/ml) |
| --- | --- | --- | --- |
| 476 | 180 | 599 | 0.183 |
| 317 | 192 | 563 | 0.032 |
| 326 | 218 | 635 | 0.038 |

Baseline Average IL-2 release induced in the lower tail part of the sigmoid reaction curve.
Top line Average IL-2 release induced at the plateau part of the sigmoid reaction curve Determination of PD-1 Antibody Functions by Reverse Signaling of IL-2 Release in HuT78/P3Z Cells In chimeric receptor P3Z, PD-1 signaling domain was replaced with the cytoplasmic domain of CD3ζ. Therefore, P3Z mediates activation upon engagement with PD-L1, rather than inhibition as original PD-1 receptor. In this assay, HuT78/P3Z cells ($3 \times 10^4$/well) were pre-incubated with hybridoma supernatants or PD-1 antibodies for 15 minutes prior to co-culture with HEK293/PD-L1 or HEK293/PD-L2 cells ($5 \times 10^4$/well) in 96-well flat bottom plates (a total volume of 200 μl/well) at 37° C. After 16-18 hours, supernatants were collected and IL-2 production was assayed by ELISA as described above.

The functional activity of murine anti-PD-1 mAbs was further confirmed by direct read-out of T-cell activation in reverse signaling assay described above. Consistent to the result described above, mu317 and mu326 had best functional activity among the mAbs we screened. As shown in Table 4 and Table 5, mu317 and mu326 were much more potent than one of the low activity mAbs, mu37, both in terms of $IC_{50}$ and maximum inhibition.

TABLE 4

Inhibition of IL-2 secretion by anti-PD-1 mAbs in HuT78/P3Z cells co-cultured with HEK293/PD-L1 cells

| Antibody | $IC_{50}$ (μ/ml) | Max inhibition, % |
| --- | --- | --- |
| 37 | 0.287 | 86.9 |
| 317 | 0.083 | 99.3 |
| 326 | 0.039 | 97.6 |

Maximum inhibition was calculated as percentage (%) of inhibition with anti-PD-1 mAbs added to the highest level of 10 μg/ml in culture.

TABLE 5

Inhibition of IL-2 secretion by anti-PD-1 mAbs in
HuT78/P3Z cells co-culturedwith HEK293/PD-L2 cells

| Antibody | $IC_{50}$ (µg/ml) | Max inhibition, % |
|---|---|---|
| 37 | 0.127 | 43.3 |
| 317 | 0.020 | 94.3 |
| 326 | 0.018 | 93.4 |

Maximum inhibition was calculated as percentage (%) of inhibition with anti-PD-1 mAbs added to the highest level of 10µg/ml in culture.

Example 4

Activation of IFN-γ Secretion by Anti-PD-1 mAb in Primary Human PBMCs Co-Cultured with HEK293/OS8/PD-L1 Cells To verify if the selected top mAbs against PD-1 also exert functional effect on primary human immune cells, we assayed the antibody function by using freshly isolated peripheral blood mononuclear cells (PBMCs), which are mainly consisted of T-cells (50-70%), B-cells and NK cells (15-30%), and monocytes (2-10%). Human PBMCs were isolated from healthy donors by density gradient centrifugation using ficoll lymphocyte separation medium (Histopaque-1077; Sigma-Aldrich, MO) according to the manufacturer's instructions. All the human blood collection followed the Internal Procedure of Beigene. PBMCs were then stimulated with anti-CD3 mAb (40 ng/mL) OKT3 (Cat. No. 16-0037, eBioscience, CA) for 3 days prior to assay. FACS analysis (Example 1) showed that PD-1 expression on the activated PBMCs (primarily T cells) was increased to variable degree dependent on individual donors (Table 6). To determine the response of pre-activated T cells to PD-1 ligand-positive tumor cells upon engagement TCR/CD3 complex, PBMCs ($1\times10^4$) were co-cultured with either HEK293/OS8/PD-L1 or HEK293/OS8/PD-L2 cells ($3\times10^4$) in 96-well flat-bottom plates for 15-18 hours. Cell-free supernatants were assayed for IFN-γ level by ELISA using Ready-Set-Go! ELISA kits (Cat. No. 88-7316, eBiosciences), which is the most prominent indicator of T-cell activation, as well as of other immune cell activation (Thakur A. et al. 2012 Vaccine, 30:4907-4920).

| PBMCs and treatment | Percent gated PD-1 staining positive cells versus total PMBCs stained | |
|---|---|---|
| | Donor-3 | Donor-4 |
| PBMCs, not stimulated/ stained by PD-1 Ab | 12.0% | 3.2% |
| PBMCs, stimulated/ stained by PD-1 Ab | 40.0% | 38.1% |
| PBMCs, not stimulated/ stained by control Ab | ≤0.5% | ≤0.5% |
| PBMCs, stimulated/ stained by control Ab | ≤0.5% | ≤0.5% |

Stimulation freshly isolated PBMCs were cultured for 3 days in presence of anti-CD3 antibody, OKT3, and IL-2.
Without stimulation fresh PBMCs subjected to antibody staining and FACS analysis.

Figure 6:
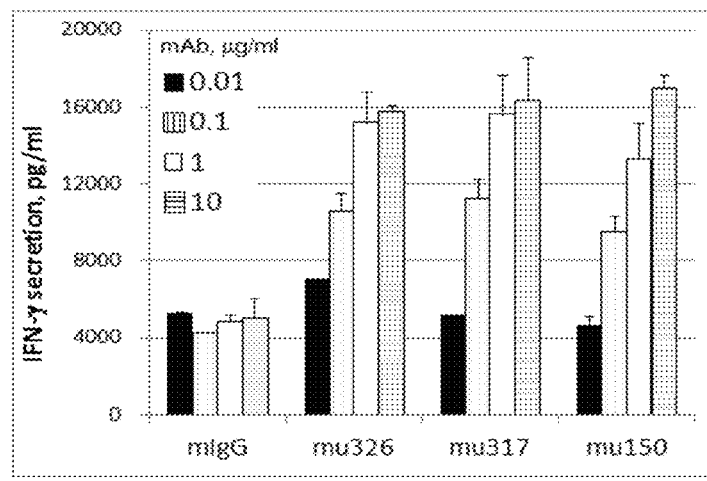
FIG. 6. (A) Histograms showing IFN-γ secretion induced by anti-PD-1 mAbs in PBMCs (Donor-19) co-cultured with cell line HEK293/OS8/PD-L1. (B) Histograms showing IFN-γ secretion induced by anti-PD-1 mAbs in PBMCs (Donor-20) co-cultured with cell line HEK293/OS8/PD-L1.
Figure 6:
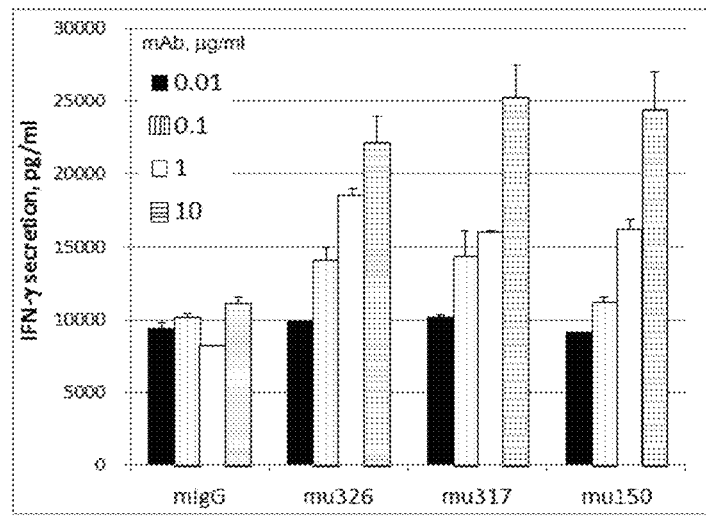

FIG. 6 demonstrated that presence of mAbs mu317 and mu326 in the co-culture of pre-activated PBMCs and HEK293/OS8/PD-L1 cells resulted in increasing IFN-γ accumulation in a dose-dependent manner. Although the base level of IFN-γ with control murine IgG treatment varies among different donors, the increase of IFN-γ secretion in PBMCs treated by mu317 or mu326 is statistically significant in the range of 0.1 to 10 µg/ml of antibody treatment. Comparing to the corresponding level of mIgG-treated PBMCs, IFN-γ secretion induced by mu317 and mu326 between the 0.1 to 10 µg/ml concentration levels increased 2.5 to 3.2 fold in PBMCs from Donor-19, and increased 1.4 to 2.3 fold in PBMCs of Donor-20, respectively.

Example 5

Activation of Human NK Cells by Anti-PD1 mAbs

Stable Cell Lines for Functional Assay in NK Cells

Primary human NK cells were reported previously to express PD-1 protein in response to IL-2 treatment and inhibiting PD-1-mediated signaling enhanced cytotoxicity of NK cells (2010 Blood, 116: 2286). For quantitative assay of functional effect excited by anti-PD-1 mAbs in NK cells, human NK cell line NK92MI (ATCC) and lung cancer cell line SK-Mes-1 (ATCC) were engineered to stably express human PD-1 and PD-L1, respectively, by retroviral transduction according to the protocols described previously (Zhang et al. 2005, Blood 106: 1544-1551, Zhang et al. 2006, Cancer Res, 66: 5927). The two stable cell lines were named as NK92MI/PD-1 and SK-Mes-1/PD-L1

Anti-PD-1 Abs Promote IFN-γ Production and Secretion in NK92MI/PD-1 Cells

Functional activity of the anti-PD-1 mAbs on NK cells was assayed by quantitative measurement of IFN-γ production and secretion in NK92MI/PD-1 cells which were co-cultured with lung cancer cell line SK-MES-1/PD-L1 at ratio of 1 to 2 in 96-well flat-bottom plate with total of $6\times10^4$ cells per well. The anti-PD-1 mAbs were added to NK92MI/PD-1 cells 15 minutes before the co-culture started, then the cells were co-cultured for overnight in $CO_2$ incubator. Cell-free supernatants were assayed for IFN-γ level h ELISA as described in Example 4.

All anti-PD-1 mAbs trigged significant increase of IFN-γ production from the baseline with low concentration of antibody treatment to top line with high concentration of antibody treatment. The two top antibodies, mu317 and mu326, had lower $EC_{50}$, than the comparison antibody SC, indicating they have more potent activating effect to the NK cells (Table 7).

TABLE 7

IFN-γ secreted in medium (pg/ml) by NK92MI/PD-1 cells in
presence of anti-PD-1 mAb and SK-MES-1/PD-L1 cells

| Antibody | Baseline (pg/ml) | Top line (pg/ml) | $EC_{50}$ (µg/ml) |
|---|---|---|---|
| 317 | 28 | 532 | 0.40 |
| 326 | 15 | 509 | 0.20 |
| 5C | 20 | 535 | 1.17 |

Baseline Average IFN-γ release induced in the lower tail part of the sigmoid reaction curve.
Top line Average IFN-γ release induced at the plateau part of the sigmoid reaction curve Anti-PD-1 Antibody Enhances Cancer Cell Killing Mediated by NK92MI/PD-1 Cells Cytotoxicity of NK92MI/PD-1 cells against SK-MES-1/PD-L1 cells was determined by lactate dehydrogenase (LDH) release assay using the CytoTox 96 Non-Radioactive Cytotoxicity Assay kit (Promega, Madison, Wis.). In brief, NK92MI/PD-1 cells ($10^5$) were pre-incubated with anti-PD-1 mAbs at final concentrations within the range of 0.004-10 µg/ml for 15 minutes, and SK-MES-1/PD-L1 cells ($2\times10^4$) were added to the immune cell culture in a 96-well V-bottom plate at an effector to tumor cell (E:T) ratio of 5:1, then co-cultured for 5 hours. The complete tumor cell lysis was set as maximum cell killing, the LDH-release, assay readout of each sample was calculated as percentage of maximum cell killing. The cell killings (%) of all samples were normalized cross the plates using 10% of baseline as the common standard.

In the specific cytotoxicity assay set as above, the selected anti-PD-1 mAbs caused a net tumor cell killing (=top line−baseline) ranging from 19% to 20.2% at high concentration of mAb input. Mu317 and mu326 had lower EC50 than mu336, indicating better potency to trigger NK92MI/PD-1 cell-mediated tumor cell killing (Table 8).

ample 13). Complement determinant regions (CDRs) were identified based on Kabat (Wu, T. T. and Kabat, E. A., 1970 J. Exp. Med. 132: 211-250) and IMGT system (Lefranc M. P. et al., 1999 Nucleic Acids Research, 27, 209-212) by sequence annotation and by internet-based sequence analysis (http://www.imgt.org/IMGT_vquest/share/textes/index.html and http://www.ncbi.nlm.nih.gov/igblast/). As shown in Table 9, the CDRs of mu317 and mu326 are very different in sequence length and identity.

TABLE 9

CDRs of mu317 and mu326

| MAbs | CDR1 | SEQ ID NO | CDR2 | SEQ ID NO | CDR3 | SEQ ID NO |
|---|---|---|---|---|---|---|
| mu317, HC | GFSLT*SYGVH* | 11 | VIWAGGSTNYNSALMS | 12 | ARAYGNYWYIDV | 13 |
| mu317, LC | KASQSVSNDVA | | 14 YAFHRFT | | 15 HQAYSSPYT | 16 |
| mu326, HC | GYTFTNYGMN | | 17 W INNNNGEPTYAEEFKG | | 18 ARDVMDY | 19 |
| mu326, LC | RAS*ESVDNYGYSFMH* | 20 | RASNLES | | 21 QQSKEYPT | 22 |

Note: CDRs in bold face are based on Kabat system; CDRs underlined are based IMGT system.

TABLE 8

Cytotoxicity of NK92MI/PD-1 cells induced by anti-PD-1mAb

| Antibody | Baseline (%) | Top line (%) | EC$_{50}$ (μg/ml) |
|---|---|---|---|
| 317 | 10 | 29.06 | 0.50 |
| 326 | 10 | 30.19 | 0.37 |
| 336 | 10 | 29.72 | 1.52 |

Baseline Percent of tumor cells killed not due to the effect of anti-PD-1 mAbs, normalized to 10% cross plates.
Top line Average percent of tumor killed in presence of highest concentrations of mAbs, i.e. 3 μg/ml and 10 μg/ml Example 6

Cloning and Sequence Analyses of PD-1 mAbs

The murine hybridoma clones secreting a specific mAb were cultured to a density of 3 to 10×10$^6$ cells in a 100 mm-tissue culture dish, and the cells were harvested through centrifugation at 1500 rpm in a swing bucket rotor. Total cellular RNA was isolated using Ultrapure RNA kit (Cat. No. CW0581, CWBIOTECH, Beijing, China) following the manufacturer's protocol. The RNA was resuspended in double-deionized water, concentration measured by Nano-Drop (ThermoFisher, Shanghai, China).

PCR primers used for mAb cDNA cloning were synthesized by Invitrogen (Beijing, China) based on the sequences reported previously (Brocks et al. 2001 Mol Med 7:461-469). The 1$^{st}$ strand cDNA was synthesized using reverse transcriptase (Cat. No. AH301-02, Transgen Biotech, Beijing, China). PCR amplification of specific mAb cDNA was performed using PCR reagent kit (Cat. No. Ap221-12, TransGen Biotech, Beijing, China) and following manufacturer's protocol. The PCR product was either directly sequenced by service provider (GeneWiz, Beijing, China) or subcloned into a pCR vector (Invitrogen), subsequently sequenced (GeneWiz).

The protein sequences of murine mAbs were analyzed by sequence homology alignment. MAbs were grouped based on sequence homology and epitope-mapping results (Ex- Example 7

Humanization of the Murine mAbs

Simulation of Antibody 3D Structure

The three dimensional structures were simulated for variable domains of mu317 and mu326 in order to identify framework residues that might be important for supporting CDR loop structures. Potentially important framework residues were kept as the original murine residues in the first round antibody humanization. The previously established structural modeling method for antibodies (Morea et al. Methods 2000 20:267-279) was adopted to simulate 3D structure of anti-PD-1 mAbs based on the known canonical structures of antibodies (Al-Lazikani et al. 1997 Journal of Molecular Biology 273:927-948). Briefly, the sequence of each variable domain (Vk and Vh) of murine antibody was blasted in the PDB database (Protein Data Bank, http://blast.ncbi.nlm.nih.gov/) to identify the most homologous antibody sequence with known high resolution structure (resolution less than 2.5 angstrom). Selected structure templates for modeling mu317 and mu326 (listed in Table 10) had the same classes of canonical loop structures in L-CDR1, L-CDR2, L-CDR3, H-CDR1, and H-CDR2 to the target antibodies to be modeled. If the templates for the Vk and the Vh came from different immunoglobulins, they were packed together by a least-squares fit of the main chain atoms to form a hybrid structure of Vk-Vh interface residues, which was used as the templates for structural homology modeling by Swiss-model program (Kiefer et al. 2009 Nucleic Acids Research 37, D387-D392). Certain side chain conformation was adjusted while the main chain conformations were retained. At the sites where the parent structure and the modeled structure had the same residue, the side chain conformation was retained. At sites where the residues were different, side chain conformations were modeled on the basis of template structure, rotamer libraries and packing considerations. After homology modeling, PLOP program (Jacobson et al. 2002 Journal of Physical Chemistry 106:11673-11680) was used to refine the homology models to minimize all-atom energy and optimize Vk and Vh interface. This step was performed to improve the stereochemistry, especially in those regions where segments of structures coming from different antibodies had been joined together.

TABLE 10

Structure templates used in antibody structure simulations

| Antibody chain | PDB code of template structure (PDB template for H-CDR3) | Sequence identity | Sequence similarity |
|---|---|---|---|
| mu317 Vk | 3MXV | 87% | 92% |
| mu317 Vh | 3VFG | 83% | 91% |
| mu326 Vk | 1EJO | 92% | 94% |
| mu326 Vh | 1NCA | 88% | 90% |
| 317-1 Vk | 4HJJ | 90% | 95% |
| 317-1 Vh | 3VFG (1AY1) | 75% | 87% |
| 326-1 Vk | 1EJO | 87% | 92% |
| 326-1 Vh | 3T2N (3CXD) | 84% | 86% |

The structures were also simulated for CDR-grafted 317-1 and 326-1 in order to guide further rounds of antibody engineering to enhance the extents of humanization and/or enhance antibody stabilities. The selected structure templates are also listed in Table 10. The structure simulations were done in a similar way to above procedure, except that the possible conformations of H-CDR3 were taken from PDB templates 1AY1 for 317-1 and 3CXD for 326-1, respectively, which contained H-CDR3s of similar size and torso region. Energy minimization for grafted H-CDR3 residues was done using PLOP.

Humanization

For humanization of the anti-PD-1 mAbs, we searched human germline IgG genes homologous to the cDNA sequences of mu317 and mu326 variable regions by blasting the human immunoglobulin gene database in IMGT (http://www.imgt.org/IMGT_vquest/share/textes/index.html) and NCBI (http://www.ncbi.nlm.nih.gov/igblast/) websites. The human IGVH and IGVκ with high homology to the PD-1 mAbs were selected as the template for humanization.

Humanization was carried out in principle by CDR-grafting. In the 1$^{st}$ round of humanization, mutations from murine to human amino acid residues in framework sequences of variable regions was guided by the simulated 3D structures, and only the murine amino acid residues whose changes retain the overall antibody and CDR loop structure were mutated to human sequence as described above. The initial versions of humanized mAbs were hu317-1 (SEQ NO 47-50) and hu326-1 (SEQ NO 55-58), which comprise a heavy chain with humanized variable heavy chain (Vh) fused to human IgG2 constant region (NCBI accession No. P01859) and a light chain with humanized variable light chain kappa (Vκ) fused to human Ig kappa C-region (NCBI Accession No. P01834). Likewise, we generated chimeric antibodies from mu317 and mu326, which are consisted of a murine VH fused to human IgG2 constant region and a murine Vκ fused to human Ig kappa C-region. The full chimeric antibodies were named as ch317 and ch326, respectively. All recombinant mAbs were expressed and purified as described in Example 1.

FACS and functional assays demonstrated that mAb hu317-1 almost retained the same binding and functional activity as the mu317 and ch317. The $EC_{50}$ difference in FACS analysis between mu317 versus ch317 and hu317-1 may be interpreted by the fact that two different detection antibodies, a goat anti-mouse IgG and a goat anti-human IgG, were used in FACS. In the two functional assays, all three versions of 317 were treated more equal, and the results also close to each other (Table 11).

As result of the initial round of humanization for mu326, mAb hu326-1 retained similar functional feature to the parental ch326 and mu326 although functional activity in FACS binding assay and in HuT78/PD-1 cell-based IL-2 release assay may be slightly weaker than ch326 (Table 12).

TABLE 11

Comparison of mu317, ch317 and hu317-1 by FACS and functional assays

| Assay/Parameter | mu317 | ch317 | hu317-1 |
|---|---|---|---|
| FACS | | | |
| $EC_{50}$ (µg/ml) | 0.11 | 0.36 | 0.46 |
| Top MFI* | 205 | 217 | 203 |
| Assay-1 | | | |
| $EC_{50}$ (µg/ml) | 0.11 | 0.08 | 0.09 |
| Top line (pg/ml) | 346 | 294 | 386 |
| Baseline (pg/ml) | 98 | 82 | 91 |
| Assay-2 | | | |
| $IC_{50}$ (µg/ml) | 0.11 | 0.10 | 0.11 |
| Max inhibition | 99.5% | 99.0% | 99.8% |

*MFI mean fluorescence intensity from FACS analysis
Assay-1 IL-2 release induced by the mAbs in HuT78/PD-1 cells co-cultured with HEK293/OS8/PD-L1 cells
Assay-2 IL-2 release induced by the mAbs in HuT78/P3Z cells co-cultured with HEK293/PD-L1 cells

TABLE 12

Comparison of mu317, ch317 and hu317-1 by FACS and functional assays

| Assay/Parameter | mu326 | ch326 | hu326-1 |
|---|---|---|---|
| FACS | | | |
| $EC_{50}$ (µg/ml) | 0.126 | 0.072 | 0.117 |
| Top MFI | 195 | 163 | 129 |
| Assay-1 | | | |
| $EC_{50}$ (µg/ml) | 0.038 | 0.074 | 0.112 |
| Top line (pg/ml) | 1149 | 1057 | 1143 |
| Baseline (pg/ml) | 242 | 250 | 283 |
| Assay-2 | | | |
| $IC_{50}$ (µg/ml) | 0.14 | 0.12 | 0.10 |
| Max inhibition | 96.9% | 81.0% | 84.4% |

Assay-1 IL-2 release induced by the mAbs in HuT78/PD-1 cells co-cultured with HEK293/OS8/PD-L1 cells
Assay-2 IL-2 release induced by the mAbs in HuT78/P3Z cells co-cultured with HEK293/PD-L1 cells Based on the 1$^{st}$ round of humanization, we further mutated the other murine amino acid (AA) residues in the framework (FR) of hu317-1_Vh and _Vκ individually to assess the impact on the antibody function. As shown in Table 13, the seven individual mutations in Vh and one mutation in Vκ of hu317-1 all have similar functional activities. Only minor changes were observed in some Vh mutation, such as hu317-2_K71V with slightly weaker inhibitory function among the mutations. However, when all the murine amino acid residues mutated together to human (hu317-3A), the function is clearly weaker than the rest mutations in FACS and IL-2 release assays.

In the initial trial described above, hu326-1 reached significant humanization level in the FR except for a few of murine AA residues left. Yet, it has weaker function than the mu326. Therefore, we made more individual mutations either back to murine residues or forward to human residues to explore the contribution of each individual AA to mAb326 function. Table 14 presented all single AA mutations made based on hu326-1_Vh template (SEQ NO 56, SEQ NO 57) and their functional assay results. Majority of the mutations showed better functional activity than those of hu326-1, matching the original mu326 mAb. A couple of mutations (E46K and F95Y) showed slightly less potency in the $EC_{50}$ or $IC_{50}$, indicating the role of those residues in the antibody structure and function.

TABLE 13

Comparison of functional activity of Fabs with humanization mutations in hu317-1 framework

| Fab and composition | | FACS, | IL-2 release in HuT78/P3Z | |
|---|---|---|---|---|
| Vh | Vκ | $EC_{50}$ | Max inhibition, % | $EC_{50}$ |
| hu317-1_Vh | hu317-1_Vκ | 0.19 | 98.78 | 0.30 |
| hu317-2_L48I | hu317-1_Vκ | 0.14 | 98.51 | 0.37 |
| hu317-2_L67V | hu317-1_Vκ | 0.15 | 98.57 | 0.30 |
| hu317-2_K71V | hu317-1_Vκ | 0.18 | 96.55 | 0.48 |
| hu317-2_N73T | hu317-1_Vκ | 0.15 | 98.29 | 0.31 |
| hu317-2_S76N | hu317-1_Vκ | 0.13 | 98.56 | 0.28 |
| hu317-2_V78F | hu317-1_Vκ | 0.18 | 98.03 | 0.38 |
| hu317-2_M82L | hu317-1_Vκ | 0.13 | 98.47 | 0.27 |
| hu317-1_Vh | HU317-2_G100Q | 0.21 | 98.86 | 0.27 |
| hu317-3A | hu317-1_Vκ | 0.32 | 79.66 | 0.35 |

Note:
Unit for $EC_{50}$ is µg/ml; mutated amino acid residue numbering is same as in the listed sequences for hu317-1; hu317-3A has all the framework sequence mutated to human.

TABLE 14

Comparison of functional activity of mAbs with mutations in hu326-1 framework

| | | IL-2 release in HuT78/P3Z | | IL-2 release in HuT78/PD-1 | |
|---|---|---|---|---|---|
| Antibody | FACS, $EC_{50}$ µg/ml | Max inhibition, % | $IC_{50}$, µg/ml | Top line, pg/ml | $EC_{50}$, µg/ml |
| ch326 | 0.118 | 93.05 | 0.074 | 993 | 0.135 |
| hu326-1 | 0.317 | 92.38 | 0.087 | 987 | 0.213 |
| hu326-2 S9P[B] | 0.145 | 96.04 | 0.075 | 1022 | 0.136 |
| hu326-2 A16E[B] | 0.155 | 96.33 | 0.078 | 1048 | 0.126 |
| hu326-2 E46K[B] | 0.132 | 95.25 | 0.079 | 1244 | 0.259 |
| hu326-2 G63D[B] | 0.139 | 96.44 | 0.064 | 1069 | 0.120 |
| hu326-2 A76V[F] | 0.102 | 96.65 | 0.071 | 1002 | 0.112 |
| hu326-2 S84N[B] | 0.131 | 96.52 | 0.060 | 1015 | 0.126 |
| hu326-2 S85N[B] | 0.110 | 95.62 | 0.093 | 932 | 0.104 |
| hu326-2 T88N[B] | 0.098 | 95.85 | 0.102 | | |
| hu326-2 F95Y[F] | 0.097 | 95.62 | 0.166 | 1028 | 0.135 |

[B]Back mutation to murine amino acid;
[F]Forward mutation to human amino acid.
All of the mutations were made in hu326-1_Vh (SEQ NO 56), which were paired with hu326-1_Vk (SEQ NO 58).

To explore the best possible Vh and Vκ sequence composition for mAbs 317 and 326 that could be used as therapeutics in human, we made a variety of combination mutations (including some mutations in the CDR sequences) in considerations of the antibody features, such as humanization level in FR, functional activities, physicochemical properties, antibody-dependent cell-mediated cytotoxicy (ADCC) and complement-dependent cytotoxicity (CDC). Most of the mutations were deemed not passing the qualification standards. Through the engineering process, six of the humanized, recombinant mAbs were selected for their potential therapeutic utility: hu317-4B2 (SEQ ID NO 43-44), hu317-4B5 (SEQ ID NO 45-46), hu317-4B6 (SEQ ID NO 23-26), hu326-3B1 (SEQ ID NO 51-52), hu326-3G1 (SEQ ID NO 53-54) and hu326-4A3 (SEQ ID NO 27-30). The CDRs of the mAb were compared to those of original murine antibodies, shown in Table 15 and Table 16.

Among the six mAbs, hu317-4B2, hu317-4B5 and hu317-4B6 are closely related to each other in sequences and very similar in their functional activities and strength. On the other hand, hu326-3B1, hu326-3G1 and hu326-4A3 are quite close to each other in sequences and functionalities (Table 17-18). Within each of the two groups of mAbs, they also shared many other features in addition to sequences and function, such as physicochemical properties and binding epitopes (described in Examples 10 and 11) though some minor differences do exist.

TABLE 15

Comparison of CDRs among different versions of mAbs 317

| mAbs | CDR1 | SEQ ID NO | CDR2 | SEQ ID NO | CDR3 | SEQ ID NO |
|---|---|---|---|---|---|---|
| mu317, HC | GFSLTSYGVH | 11 | VIWAGGSTNYNSALMS | 12 | ARAYGNYWYIDV | 13 |
| hu317-1, HC | GFSLTSYGVH | 11 | VIWAGGSTNYN<u>PS</u>L<u>K</u>S | 59 | ARAYGNYWYIDV | 13 |
| hu317-4B2, HC | GFSLTSYGVH | 11 | VI<u>Y</u>AGGSTNYN<u>PS</u>L<u>K</u>S | 60 | ARAYGNYWYIDV | 13 |
| hu317-4B5, HC | GFSLTSYGVH | 11 | VI<u>Y</u>AGGSTNYN<u>PS</u>L<u>K</u>S | 60 | ARAYGNYWYIDV | 13 |

TABLE 15-continued

Comparison of CDRs among different versions of mAbs 317

| mAbs | CDR1 | SEQ ID NO | CDR2 | SEQ ID NO | CDR3 | SEQ ID NO |
|---|---|---|---|---|---|---|
| hu317-4B6, HC | GFSLTSYGVH | 11 | VIYADGSTNYNPSLKS | 32 | ARAYGNYWYIDV | 13 |
| mu317, LC | KASQSVSNDVA | 14 | YAFHRFT | 15 | HQAYSSPYT | 16 |
| hu317-1, LC | KASQSVSNDVA | 14 | YAFHRFT | 15 | HQAYSSPYT | 16 |
| hu317-4B2, LC | KSSESVSNDVA | 61 | YAFHRFT | 15 | HQAYSSPYT | 16 |
| hu317-4B5, LC | KSSESVSNDVA | 61 | YAFHRFT | 15 | HQAYSSPYT | 16 |
| hu317-4B6, LC | KSSESVSNDVA | 61 | YAFHRFT | 15 | HQAYSSPYT | 16 |

Note: AA residues underlined are changed from murine sequence to human antibody sequences or for improvement of physicochemical properties.

TABLE 16

Comparison of CDRs among different versions of mAbs 326

| mAbs | CDR1 | SEQ ID NO | CDR2 | SEQ ID NO | CDR3 | SEQ ID NO |
|---|---|---|---|---|---|---|
| mu326, HC | GYIFINYGMN | 17 | WINNNNGEPIYAEEFKG | 18 | ARDVMDY | 19 |
| hu326-1, HC | GYIFINYGMN | 17 | WINNNNGEPIYAQGFRG | 62 | ARDVMDY | 19 |
| hu326-3B1, HC | GYIFINYGMN | 17 | WINNNNGEPIYAQDFRG | 62 | ARDVMDY | 19 |
| hu326-3G1, HC | GYIFINYGMN | 17 | WINNNNGEPIYAQDFRG | 62 | ARDVMDY | 19 |
| hu326-4A3, HC | GYIFINYGMN | 17 | WINNNNAEPIYAQDFRG | 38 | ARDVMDY | 19 |
| mu326, LC | RASESVDNYGYSFMH | 20 | RASNLES | 21 | QQSKEYPI | 22 |
| hu326-1, LC | RASESVDNYGYSFMH | 20 | RASNLES | 21 | QQSKEYPI | 22 |
| hu326-3B1, LC | RASESVDNYGYSFMH | 20 | RASNLES | 21 | QQSKEYPI | 22 |
| hu326-3G1, LC | RASESVDNYGYSFMH | 20 | RASNLES | 21 | QQSKEYPI | 22 |
| hu326-4A3, LC | RASESVDNYGYSFMH | 20 | RASNLES | 21 | QQSKEYPI | 22 |

Note: AA residues underlined are changed from murine sequence to human antibody sequences or for improvement of physicochemical properties.

TABLE 17

Binding activities of humanized mAbs assayed by ELISA and FACS

| mAbs | ELISA, $EC_{50}$ μg/ml | FACS, $EC_{50}$ μg/ml |
|---|---|---|
| hu317-4B2 | 0.066 | 0.129* |
| hu317-4B5 | 0.057 | 0.115* |
| hu317-4B6 | 0.061 | 0.092* |
| hu326-3B1 | 0.092 | 0.165 |
| hu326-3G1 | 0.088 | 0.190 |
| hu326-4A3 | 0.091* | 0.142* |

*FACS data by using Fab version of antibodies without normalization.
**Data from bridging study and normalized.

TABLE 18

Binding affinity of Fabs assayed by SPR

| Fab | $K_{on}$ ($M^{-1}, s^{-1}$) | $K_{off}$ (s) | $K_D$ (M) |
|---|---|---|---|
| hu317-4B5 | $3.89 \times 10^5$ | $9.07 \times 10^{-5}$ | $2.33 \times 10^{-10}$ |
| hu317-4B6 | $5.71 \times 10^5$ | $8.37 \times 10^{-5}$ | $1.47 \times 10^{-10}$ |
| hu326-3B1 | $2.18 \times 10^5$ | $1.90 \times 10^{-4}$ | $8.70 \times 10^{-10}$ |
| hu326-3G1 | $2.00 \times 10^5$ | $2.01 \times 10^{-4}$ | $1.00 \times 10^{-9}$ |

Affinity Determination of Humanized Anti-PD-1 Fabs by SPR

Anti-PD-1 mAbs were converted into Fab version by PCR to fuse the variable regions of heavy and light chains to the N-terminus of human IgG2-CH1 and constant region of kappa chain, respectively, and subcloned in pcDNA3.1 vector (Invitrogen). Both expression vectors were co-expressed in 293-F cells using a transient transfection protocol similar to the transient expression of whole antibodies. Briefly, the Fab kappa chain was PCR amplified and subcloned in pcDNA3.1-based expression vector (Invitrogen, Carlsbad, Calif., USA). In a separate plasmid, the heavy chain variable region (VH) together with the CH1 coding sequence from human IgG2 was fused with a C-terminal c-Myc-His8 tag by overlapping PCR, and then subcloned in the expression vector. The C232S and C233S (Kabat residue numbering, Kabat et al. Sequence of proteins of immunologic interest, 5th ed Bethesda, Md., NIH 1991) mutations were introduced in the IgG2 heavy chain to prevent disulfide bond exchange and stabilize human IgG2 in the IgG2-A conformation (Lightle et al. 2010 Protein Sci 19(4): 753-762). Both constructs contained a signal peptide upstream of the Fab mature sequences. Secreted expression of Fab was achieved by co-transfection of above 2 plasmids into 293-F cells and cell culture supernatants were harvested 6-7 days post transfection. His8-tagged Fabs were purified from cell culture supernatants using a Ni-sepharose Fast Flow column (Cat. No. 17531801, GE Life Sciences) followed by size exclusion chromatography using a HiLoad 16/60 Superdex200 column (Cat. No. 17106901, GE Life Sciences). The purified Fabs were concentrated to 0.5-5 mg/mL in PBS and stored in aliquots in −80° C. freezer.

For affinity determinations of anti-PD-1 Fabs, SPR assays were used with the BIAcore™ T-200 instrument (GE Life Sciences). Briefly, human PD-1/His or cynomolgus monkey PD-1/His was coupled to activated CM5 biosensor chips (Cat. No. BR100530, GE Life Sciences) to achieve approximately 100-200 response units (RU), followed by blocking un-reacted groups with 1M ethanolamine Fab samples of increasing concentration from 0.12 nM to 90 nM were injected in the SPR running buffer (10 mM HEPES, 150 mM NaCl, 0.05% Tween20, pH7.4) at 30 μL/minute, and binding responses on human PD-1/His or monkey PD-1/His were calculated by substracting of RU from a blank flow-cell. Association rates ($k_{on}$) and dissociation rates ($k_{off}$) were calculated using the one-to-one Langmuir binding model (BIA Evaluation Software, GE Life Sciences). The equilibrium dissociation constant ($K_d$) was calculated as the ratio $k_{off}/k_{on}$.

The SPR-determined binding affinities of anti-PD-1 Fabs were listed in Table 18. Each anti-PD-1 Fab bound with high affinity ($K_d$=0.15-1 nM) to human PD-1. All Fabs, except 326-3G1, bound with slightly lower but comparable (within 5 fold in Kd) affinities to cynomolgus monkey PD-1.

Example 8

Generation and Expression of Recombinant Anti-PD-1 mAbs with Modified Human IgG4 Constant Region Since PD-1 is primarily expressed in activated T cells, PD-1 blocking antibodies linked to naturally occurring type of IgG-Fe moieties are expected to induce Fc-mediated effector functions, such as ADCC and CDC, to a variable degree depending on the IgG subclasses, which results in elimination of activated T cells (Natsume A et al, 2009 Drug Des Devel Ther. 3: 7-16). Human antibody subclass IgG4 was shown in many previous reports that it has modest ADCC and almost no CDC effector function (Moore G L, et al. 2010 MAbs, 2:181-189). On the other hand, natural IgG4 was found less stable in stress conditions such as in acidic buffer or under increasing temperature (Angal, S. 1993 Mol Immunol, 30:105-108; Dall'Acqua, W. et al, 1998 Biochemistry, 37:9266-9273; Aalberse et al. 2002 Immunol, 105:9-19). In order to spare PD-1 T cells from being killed and to improve physicochemical properties of the anti-PD-1 antibodies, the humanized mAbs were linked to IgG4 engineered by combinations of mutations to have reduced or null FcγR binding or C1q binding activities, therefore, attenuating or eliminating ADCC and CDC effector functions. Considering physicochemical properties of antibody as a biological drug, one of the less desirable, intrinsic properties of IgG4 is dynamic separation of its two heavy chains in solution to form half antibody, which lead to bi-specific antibodies generated in vivo via a process called "Fab arm exchange" (Van der Neut Kolfschoten M, et al. 2007 Science, 317:1554-157). The mutation of serine to proline at position 228 (EU numbering system) appeared inhibitory to the IgG4 heavy chain separation (Angal, S. 1993 Mol Immunol, 30:105-108; Aalberse et al. 2002 Immunol, 105:9-19). Some of the amino acid residues in the hinge and γFc region were reported to have impact on antibody interaction with Fcγ receptors (Chappel S M, et al. 1991 Proc. Natl. Acad. Sci. USA, 88:9036-9040; Mukherjee, J. et al., 1995 FASEB J, 9:115-119; Armour, K. L. et al. 1999 Eur J Immunol, 29:2613-2624; Clynes, R. A. et al, 2000 Nature Medicine, 6:443-446; Arnold J. N., 2007 Annu Rev immunol, 25:21-50). Furthermore, some rarely occurring IgG4 isoforms in human population may also elicit different physicochemical properties (Brusco, A. et al. 1998 Eur J Immunogenet, 25:349-55; Aalberse et al. 2002 Immunol, 105:9-19). However, lumping all the mutations and isoforms previously discovered into a specific antibody does not warrant for an ideal antibody molecule to share all the features for therapeutics such as described above, which may be resulted from contradictory effect of the combined mutations and from impact of variable region to the effector function and physicochemical properties of an antibody Ogawa T. et al., 2010 Prot Eng Design Select, 23:385-392; Perchiacca J. M. and Tessier P. M., 2012 Ann Rev Biomol Eng 3:263-286).

To generate anti-PD-1 mAbs with least ADCC, CDC and instability, we modified the hinge and γFc region of human IgG4 by introduce a number of combinations of mutations, which created IgG4mt1 to IgG4mt12. Some of the modified IgG4 variants were clearly less desirable as indicated by our assay results, several relevant IgG4 variants and modified sequences were listed in Table 19. The assessment of these antibodies is described herein.

TABLE 19

Sequence modifications of IgG4 variants

| IgG4 and variants | Amino acid residues* | | | | | | | | | | | |
|---|---|---|---|---|---|---|---|---|---|---|---|---|
| | ... 228 | 229 | 230 | 231 | 232 | 233 | 234 | 235 | 236 ... | 265 ... | 309 ... | 409 ... |
| IgG4 | ... S | C | P | A | P | E | F | L | G ... | D ... | L ... | R ... |
| IgG4mt1 | ... P | C | P | A | P | E | F | L | G ... | D ... | L ... | R ... |
| IgG4mt2 | ... P | C | P | A | P | P | V | A | G ... | D ... | L ... | R ... |
| IgG4mt6 | ... P | C | P | A | P | P | V | A | G ... | A ... | L ... | R ... |
| IgG4mt8 | ... P | C | P | A | P | P | V | A | G ... | T ... | L ... | R ... |
| IgG4mt9 | ... P | C | P | A | P | P | V | A | G ... | A ... | L ... | K ... |
| IgG4mt10 | ... P | C | P | A | P | P | V | A | G ... | A ... | V ... | K ... |

*Amino acid numbering is based on EU system. Changes are highlighted by underline.

Example 9

IgG4Mt10 has No FcγR Binding, Lowest ADCC and CDC Effector Function

ADCC is initiated when an antibody binds to cell surface target protein followed by ligation to Fcy receptors (FcγRs) expressed on effector cells. It was well documented that human IgG1 has significantly higher binding affinity to FcγRs than IgG2 and IgG4, specially, binding to FcγR-I and FcγR-IIIA, which correlated to the strength of IgG1 to activate ADCC. Reminiscent of ADCC, CDC is activated when an antibody cross-links a cell surface target and C1q protein, which followed by a cascade reaction of complement complex formation and target cell lysis. As proxy of ADCC and CDC, assays for antibody binding to FcγRs and C1q may serve as the fundamental indicator of ADCC and CDC. We therefore systematically assessed the mAbs binding to all the major FcγRs.

FcγR Binding

Binding of various IgG4 mutants to FcγRs was determined by flow cytometry. In brief, a series of HEK293 transfectants expressing human FcγRs were established. These transfectants expressed FcγRI, FcγRIIA, FcγRIIB or FcγRIIIA Multi-subunit FcγRs (i.e., FcγR1 and FcγRIIIA) were co-expressed with FcRγ. Polymorphic variants (i.e., FcγRIIA H131 and R131, FcγRIIIA F158 and V158) were also included. A secondary antibody (goat anti-human IgG F(ab)'2-Alexa Fluor 488, Jackson ImmunoResearch, West Grove, Pa., USA) was used to detect the binding of anti-PD-1 mAbs with modified IgG4 variants (Table 19) to FcγR$^+$ HEK293 cells. As expected, anti-PD-1 mAbs in IgG1 format (hu317-1/IgG1 and hu317-4B6/IgG1) bind strongly to all FcγR$^5$ including FcγR$^1$, FcγRIIA (H131 and 8131 alleles), FcγRIIB, and FcγRIIIA (V 158 and F158 alleles) (Table 20). Interestingly, when the two different version of humanization mAbs, hu317-1 and hu317-4B6 (with differences in both Vh and Vκ), were generated in the same IgG4 variant format, such as either in IgG4mt1 or in IgG4mt6 format, their binding strength (MFI) vary by an range from a couple fold to close to 100 fold (e.g. 455.2/115.7=3.9 fold; 13.6/1.0=13.6 fold; 434.6/4.9=88.7 fold; and etc see Table 20). It is consistent to the previous findings by other that the variable regions of antibodies do have significant impact on the binding to FcRs, therefore, exerting the impact on effector function such as ADCC (Igawa T. et al., 2010 Prot Eng Design Select, 23:385-392; Perchiacca J. M. and Tessier P. M., 2012 Ann Rev Bimol Eng 3:263-286).

As demonstrated in Table 20, when hu317-4B6 and hu326-4A3 were made in IgG4mt10 format, they have the lowest binding activity to FcγRs among the PD-1 mAbs and IgG variant formats listed in the table, as well as many other humanization mAbs and IgG formats we have tested in the study. The uniqueness of hu317-4B6 and hu326-4A3 in IgG4mt10 format in this regard may not be extended to the same family of humanization mAbs with somewhat distant sequence homology, such as hu317-1, as described above.

TABLE 20

Binding strength (MFI*) of anti-PD-1 mAbs to Fc × Rs determined by FACS

| mAbs | FcγRI | FcγRIIA (H131) | FcγRIIA (R131) | FcγRIIB | FcγRIIIA (F158) | FcγRIIIA (V158) |
|---|---|---|---|---|---|---|
| hu317-1/ IgG1 | 2152.9 | 168.7 | 139.6 | 442.4 | 99.7 | 277.2 |
| hu317-4B6/ IgG1 | 2771.7 | 1.7 | 0.6 | 1.9 | 28.0 | 293.7 |
| hu317-I/ gG4mt1 | 455.2 | 21.3 | 21.9 | 434.6 | 0.6 | 20.7 |
| hu317-4B6/ IgG4mt1 | 115.7 | 0.2 | 0.0 | 4.9 | 0 | 6.1 |
| hu317-1/ IgG4mt6 | 13.6 | 1.0 | 0.8 | 1.8 | 0.9 | 1.1 |
| hu317-4B6/ IgG4mt6 | 1.0 | 0 | 0 | 0 | 0 | 0 |
| hu317-4B6/ IgG4mt10 | 0.4 | 0 | 0 | 0 | 0 | 0 |
| hu326-4A3/ IgG4mt10 | 0.5 | 0 | 0 | 0 | 0 | 0 |

*MFI: mean fluorescence intensity from FACS analysis

ADCC

Figure 7:
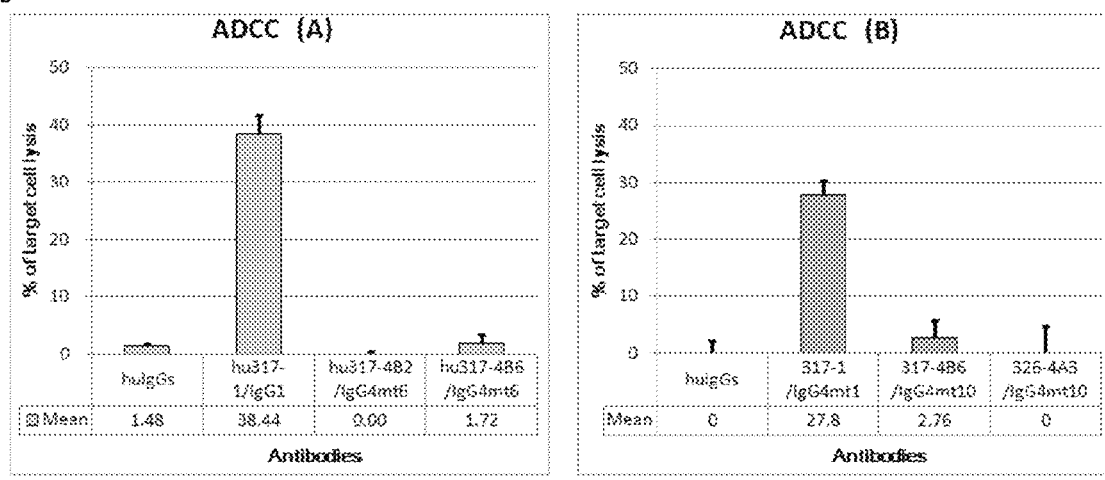
FIG. 7. (A) and (B) ADCC activities of anti-PD-1 mAbs by co-culture of effector cells (NK92MI/PD-1) and target cells (HuT78/PD-1). Means were calculated from two data points of the representative experiments. The mAbs were added to concentration of 10 m/ml. Experiment performed as described in Example 9.

Classical ADCC involves activation of NK cells by antibodies engaging to FcγRIIIA or CD16. To verify whether humanized anti-PD-1 mAbs induce ADCC, NK92MI/CD16V cells, which were generated from NK92MI cells (ATCC) by co-transducing expression plasmids containing CD16 (V158 allele) and FcRγ genes, were used as effector cells, and PD-1-expressing T cell line, HuT78/PD-1, was used as target cells. NK92MI/CD16V cells ($4 \times 10^4$) were co-cultured with equal number of HuT78/PD-1 cells in 96-well V-bottom plates for 5 h. Cytotoxicity was determined by LDH release assay described in previous section. The results confirmed that hu317-4B2/IgG4mt6, hu317-4B6/IgG4mt6, hu317-4B6/IgG4mt10 and hu326-4A3/IgG4mt10 all have base level of ADCC comparing to the positive controls (FIG. 7). The minor difference in ADCC between those 4 mAbs may be attributable to experimental error (see error bars in FIG. 7).

CDC

Human IgG4 antibodies, in general, do not induce any CDC via classical pathway. Whether anti-PD-1 mAbs in IgG4mt10 format will trigger CDC was evaluated using a PD-1-expressing T cell line, Hut78/PD-1, and fresh human serum from healthy donors. Cell lysis by CDC was determined by Celltiter glo assay kits (Promega, Beijing, China). In brief, HuT78/PD-1 cells ($2 \times 10^4$) were incubated in serum-free RPMI1640 (Invitrogen) with anti-PD-1 Abs (10 μg/ml) at 37° C. for 15 minutes before adding normal human serum (NHS) to the final concentration of 15% or 50% in 96-well flat-bottom plates in a total volume of 120n1. After overnight incubation at 37° C., cells were lysed and assayed for ATP concentration. To test whether humanized anti-PD-1 mAbs in IgG4mt10 can kill PD-1$^+$ primary T cells via CDC, PBMCs isolated from healthy donors were pre-activated with anti-CD3 Ab OKT3 (40 ng/ml) for 3 days before co-culture with anti-PD-1 Abs plus NHS. The amount of ATP is directly proportional to the number of cells present in culture. Fluorescence was read using a 96-well fluorometer (PHERA Star FS, BMG LABTECH). The results are expressed in relative fluorescence units (RFU) that are proportional to the number of viable cells. The percent CDC activity was calculated as follows: % CDC activity=[(RFU test−RFU background)/(RFU at total cell lysis−RFU background)]×100. In general, we were not able to detect any ADCC mediated by anti-PD-1 mAbs in IgG4mt10 format that bind to activated PBMCs. In hypersensitive experimental conditions, such as using PD-1 highly-expressing cell line, high serum and antibody concentration, we detected very low level of CDC in some occasions, and there is not much differences between different versions and anti-PD-1 mAbs, indicating the anti-PD-1 mAbs in IgG4 variant formats retained the feature of low or no CDC activity as the common form of IgG4.

Example 10

Humanized Anti-PD-1 mAbs in IgG4Mt10 Format have Enhanced Stability Under Stress Conditions Stability of Anti-PD-1 Antibodies in High Temperature and Acidic Conditions Anti-PD-1 antibodies used in stability studies were all purified from protein A column followed by size exclusion chromatography (SEC) as described in previous sections. Following purification, the aggregate contents of purified antibody samples were monitored in analytical size exclusion chromatography-high performance liquid chromatography (SEC-HPLC), which fell within the range of 0%-0.5%.

For SEC-HPLC analysis, the antibody samples were analyzed using a TSKgel G3000 SWXL column (7.8×300 mm, Cat. No. 08541, Tosoh Bioscience, Shanghai, China) under isocratic elution condition (elution buffer 0.2 M sodium phosphate, pH7.2), and subsequent detection at UV-215 nm. In each run, 10 microliters of antibody sample was loaded onto the column and eluted at a flow rate of 1 mL/minute. The dimer or larger aggregate species of antibody were separated from monomeric species and the percentages of dimers and aggregates were determined based on the integrated peak areas from UV traces.

For speed-enhanced shelf stability study, anti-PD-1 antibodies (10-40 mg/mL in PBS) were kept in incubators at 40-50° C. for 4-7 days in order to test the stability of antibodies in high temperature condition. The antibody samples were then analyzed for heat-induced formation of dimer and aggregates in SEC-HPLC. For each of the anti-PD-1 antibodies analyzed, less than 2% became higher molecular weight species (dimers and aggregates), indicating the anti-PD-1 antibodies had good stability in high temperature conditions.

Antibody's stability in acidic condition has been a key challenge in the downstream manufacturing process (Liu et al. 2010 mAbs 2:480-499). Antibody elution from protein A and inactivation of virus usually require incubation of antibody in low pH (2.5-4) conditions. However, such acidic conditions could potentially cause antibody denaturation and aggregation. Human IgG4 has been known to be less stable than IgG1 and IgG2 (2002 Immunology 105:9). Therefore, we assayed the humanized mAbs made with various IgG4 mutant forms. Briefly, Antibody stabilities in low pH conditions were studied by 1:1 volume of each antibody sample (10 mg/mL in PBS) mixed with low pH buffers containing 50 mM sodium citrate, 100 mM NaCl at pH3.6, 3.3, 3.0 or 2.7, respectively. After 1 hour incubation at room temperature, the antibody samples in low pH conditions were neutralized by 1:5 dilution into SEC-HPLC elution buffer containing 0.2M sodium phosphate, pH7.2. SEC-HPLC analyses were done as described above and percentages of dimers and aggregates induced by low pH conditions were quantified. The anti-PD-1 mAb 317-4B6 in IgG1 format was most stable in bioprocessing-relevant acidic conditions even when pH value get as low as 2.7. Among the anti-PD-1 mAbs made in several IgG4 variants, hu317-4B6/IgG4mt10 and hu326-4A3/IgG4mt10 were the most stable under the acidic buffer condition (Table 21) as the acid-induced aggregates were significantly reduced to a level that was comparable to that of the IgG1 format of anti-PD-1 mAbs, 317-4B6 and 326-4A3, i.e. the soluble aggregate is less than 2% (Table 21).

TABLE 21

Dimer and soluble aggregates formed in acidic buffers and assayed by SEC-HPLC

| anti-PD-1 mAbs | % of dimer and aggregates | | | | |
|---|---|---|---|---|---|
| | pH 7.2 | pH 3.6 | pH 3.3 | pH 3.0 | pH 2.7 |
| 317-4B6/IgG1 | 0.0% | 0.0% | 0.2% | 0.1% | 0.2% |
| 317-4B6/IgG4mt1 | 0.0% | 1.0% | 11.0% | 49.0% | 48.0% |
| 317-4B6/IgG4mt3 | 0.0% | 13.0% | 31.0% | >50% | >50% |
| 317-4B6/IgG4mt6 | 0.0% | 4.0% | 41.0% | >50% | >50% |
| 317-4B6/IgG4mt9 | 0.0% | 0.5% | 2.1% | 3.3% | 2.0% |
| 317-4B6/IgG4mt10 | 0.0% | 0.2% | 0.6% | 0.6% | 1.4% |
| 326-4A3/IgG4mt10 | 0.0% | 0.0% | 0.4% | 0.5% | 1.2% |

Example 11

Mapping the Binding Epitopes of Anti-PD-1 mAbs

Previous reports about the crystal structures of PD-1/PD-L1 and PD-1/PD-L2 complexes had shed light to understanding critical amino acid (AA) residues on PD-1 which are required for the ligand-binding (Zhang et al. 2004 Immunity, 20:337-347; Lin D. Y. et al. 2008 PNAS 105:3011-3016; Lazar-Molnar E. et al. 2008 PNAS, 105:10483-10488). In fact, six of such AA residues were identified on the receptor through point mutation analysis required for PD-L1 binding. Five of the six AA residues were also required for PD-L2 binding (Lin D. Y. et al. 2008 PNAS 105:3011-3016). Based on the information from the structure-guided mutation analysis we hypothesized that most effective way for functional mAbs to block PD-1 mediated signaling is to compete with PD-1 ligands by binding to the six critical AA residues, therefore, occupying the binding epitopes required for the ligand binding. To explore the hypothesis and to understand the mechanism of action by functional PD-1 antibodies, we have made six mutants of PD-1 by replacing each of the six critical AAs to Ala, individually, i.e. K45A, I93A, L95A, P97A, I101A and E103A (AA residue numbering based on Lin D.Y. et al. 2008 PNAS 105:3011-3016). The mutant PD-1/Fc and PD-1/His (FIG. 1) were used as templates for PCR-guided mutagenesis or rolling-circle mutagenesis using Fast Mutagenesis System (Cat. No. FM111, Transgen Biotech, Beijing, China). All mutants were sub-cloned in our pcDNA-based expression vectors, and verified by sequencing. The mutated and wild-type PD-1 proteins were expressed by transient transfection (described in Example 1), and prepared after 4 to 6 days of culture. The conditioned media (CM) were analyzed by Western blot to verify the PD-1 protein expression in terms of quality and quantity. The supernatants (CM), after clearing cell debris, were directly used in ELISA analysis or Western blot for epitope-mapping.

Figure 8:
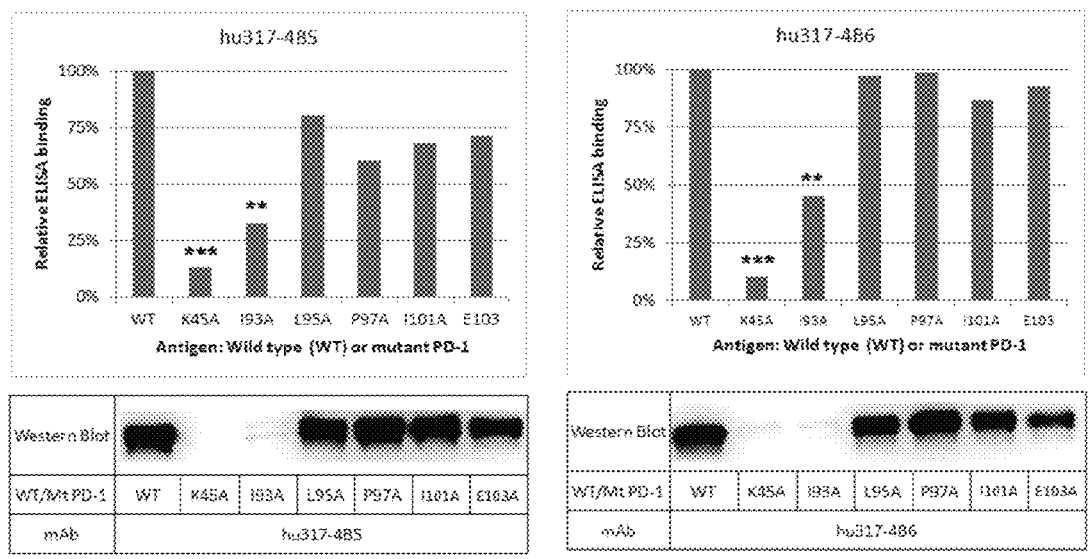
FIG. 8. Mapping the binding epitopes of anti-PD-1 mAbs by ELISA (up-panel) and Western Blot (lower panel). Conditioned media containing WT or Mt PD-1 were used to assess binding activity by ELISA and Western Blot.  indicates the AA residues to which the mAb binding activity reduced to 25-50% of WT PD-1. * indicates the AA residues to which the mAb binding activity reduced below 25% of WT PD-1.
Figure 8:
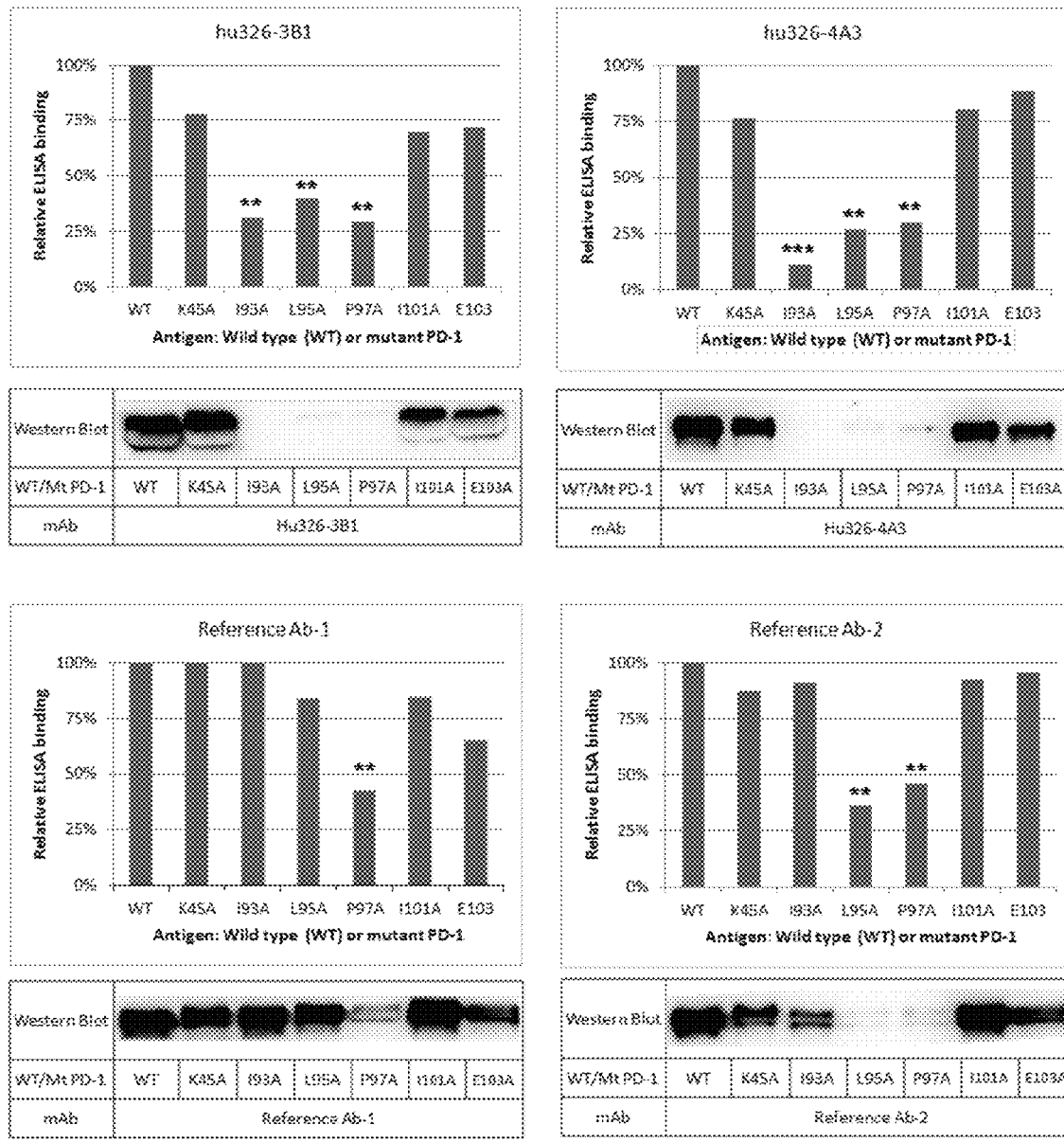

To study the binding epitopes of humanized anti-PD-1 mAbs, ELISA assays using the wild-type (WT) and mutant (Mt) PD-1 were performed to assess the binding activities of hu317-4B5, hu317-4B6, hu326-3B1 and hu326-4A3. For comparison to check the uniqueness of the antibody binding signature, two reference antibody (Reference Ab-1 and Reference Ab-2 from U.S. Pat. No. 8,008,449B2 and U.S. Pat. No. 8,168,757B2, respectively) were included in the study. Equal volume of CM containing WT or Mt PD-1 was coated in 96-well plate for all mAbs in the same ELISA assay. All ELISA results were normalized using the mean ELISA readings of WT PD-1 binding signals as the standard. ELISA binding signals to a specific Mt PD-1 were further normalized against the highest antibody binding read-out (set as 100%) to the specific Mt PD-1. For convenience of data analysis, When a mAb's ELISA binding signal for a specific mutant dropped below 50% relative to WT PD-1, it is defined that the amino acid residue is a significant binding epitope because whose mutation significantly abrogated the antibody binding. Likewise, if a mAb's ELISA binding signal for a specific mutant dropped below 25%, it is defined as very significant. As shown in FIG. 8, two of the critical AA residues in PD-1, K45 and I93, are significant or very significant epitopes for mAbs hu317-4B5 and hu317-4B6 binding, and three AA residues, I93, L95 and P97, are either significant or very significant epitopes for hu326-3B1 and hu326-4A3. On the other hand, the two reference antibodies have distinctive binding epitopes, P97 is significant for Reference Ab-1, while L95 and P97 are significant for Reference Ab-2.

Interestingly, when the PD-1 protein is denatured in Western Blot, mAb hu317-4B5 and -4B6 were still capable of binding to WT PD-1 though the critical binding epitopes (K45 and I93) are not close to each other (non-linear). It indicated that the PD-1 protein became renatured to some degree after denaturation in SDS-PAGE of Western Blot process, which allows the anti-PD-1 mAbs to recognize and bind to it. Taking the advantage of this observation, we performed Western Blot analysis for all six antibodies used in above ELISA study. The overall results from Western Blot corroborated very well to the ELISA results, i.e. the significant or very significant epitopes, whose mutations resulted in low binding signals in ELISA, also gave weakest Western Blot band comparing to the binding to other mutant PD-1 (FIG. 8). Some minor differences between ELISA and Western Blot were also observed, e.g., the ELISA binding signals on I93A and E103A by reference Ab-2 were relatively stronger than those in Western Blot. It may be indicative of that those AA residues may also contribute to the binding because whose mutations impacted the binding though only under stress condition (i.e. denaturation or losing native conformation). As summarized in Table 22, the anti-PD-1 mAbs in this invention have identifiable binding epitopes differing from other anti-PD-1 antibody.

TABLE 22

Summary* of key epitopes by anti-PD-1 mAbs

|            | K45A | I93A | L95A | P97A | I101A | E103A |
|------------|------|------|------|------|-------|-------|
| hu317-4B5  | ***  | **   |      |      |       |       |
| hu317-4B6  | ***  | **   |      |      |       |       |
| hu326-3B1  |      |      | **   | **   | **    |       |
| hu326-4A3  |      | ***  | **   | **   |       |       |
| Ref. Ab-1  |      |      |      | **   |       |       |
| Ref. Ab-2  |      |      | **   | **   |       |       |

* based on Fig.8

Example 12

Figure 9:
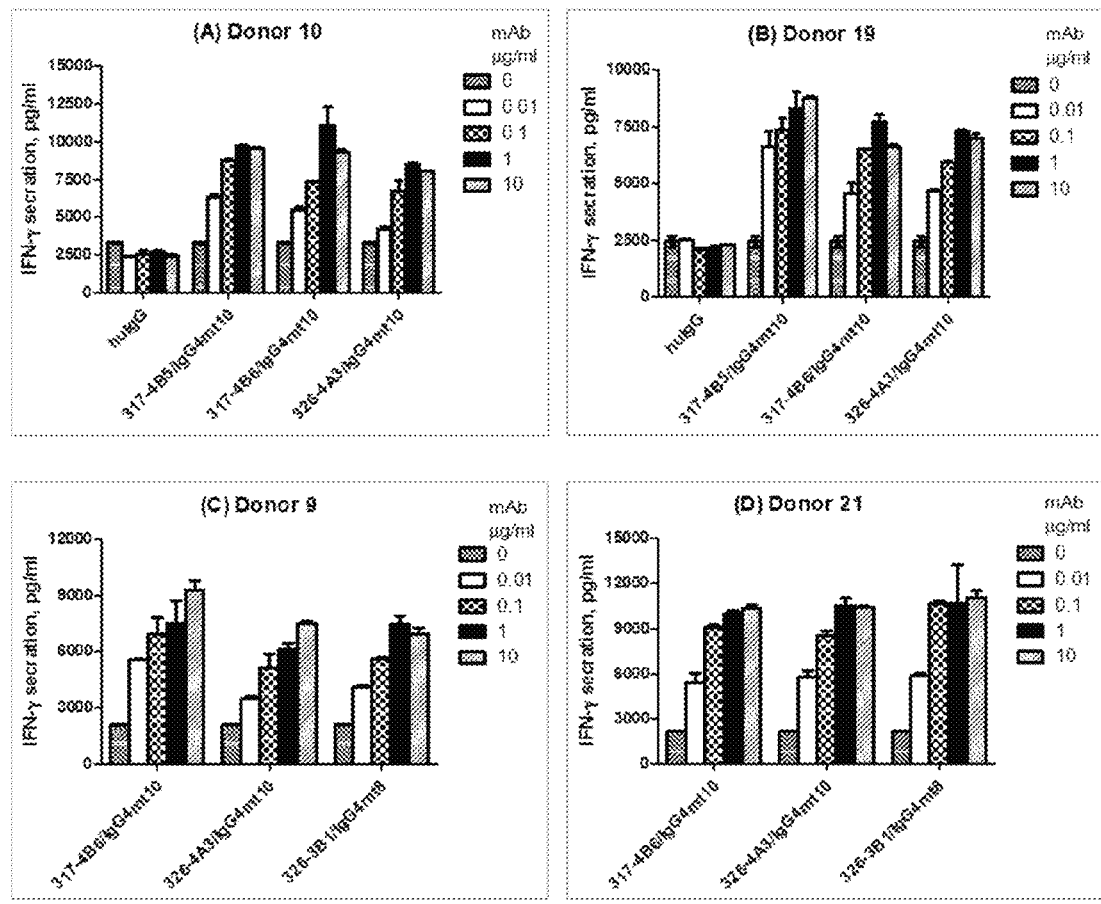
FIG. 9. IFN-γ release induced by humanized anti-PD-1 mAbs in primary human PBMCs from different healthy donors, which were co-cultured with HEK293/OS8/PD-L1 cells.

Anti-PD-1 mAbs Activate Primary Human PBMCs and Inhibit Tumor Growth in Xenograft Mouse Models Humanized Anti-PD-1 mAbs Activate Human PBMCs Throughout the humanization processes, the humanized anti-PD-1 mAbs at various stages retained similar functional activities as assessed by ELISA, FACS and immune cell-based cytokine release assays. To confirm the function of final versions of humanized mAbs, we assayed the activating functions of hu317-4B5, hu317-4B6, hu326-3B1 and hu326-4A3 using primary human PBMCs. The results demonstrated that those mAbs throughout the humanization maintained the original murine mAb functions to activate primary PBMCs although the degree of activation differs among the four donors due to the variance of individual's genetic background (FIG. 9).

Figure 10:
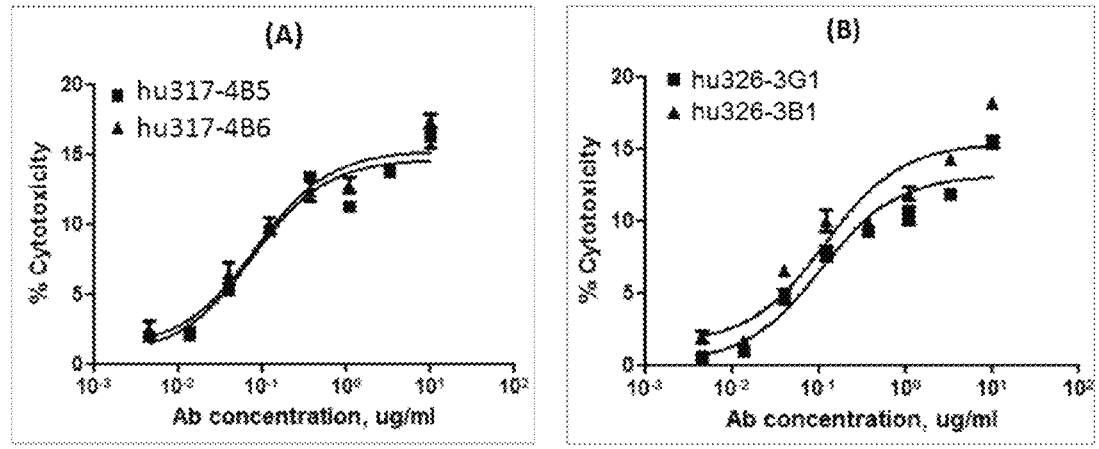
FIG. 10. Cytotoxicity of NK92MI/PD-1 cells enhanced by humanized anti-PD-1 mAbs, hu317 (A) and hu326 (B). The target lung cancer cells, SK-MES-1/PD-L1, were co-cultured with the effector cells at the (T to E) ratio of 1 to 2, and assayed as described in Example 12.

Humanized Anti-PD-1 mAbs Enhance NK Cell-Based Cytotoxicity Against Cancer Cells Reminiscent of the original murine mAbs, the humanized anti-PD-1 mAbs, hu317-4B5, hu317-4B6, hu326-3B1 and hu326-3G1, enhance NK92MI/PD-1 cell-mediated cytotoxicity against the target lung cancer cells, SK-MES-1/PD-L1, in a dose-dependent manner (FIG. 10, Table 23). It appeared evident that in principle the humanized anti-PD-1 mAbs might function to break immune cell tolerance mediated by PD-1 signaling, enhancing the cancer killing activity by immune cells, e.g. NK cells and cytotoxic T-Lymphocytes.

Humanized Anti-PD-1 mAb Activates Human PBMCs and Inhibits Tumor Growth in a Mouse Xenograft Cancer Model In Vivo All above experimental evidences indicated that the anti-PD-1 mAbs might work in mouse cancer models utilizing immune-compromised mice xenografted with human cancer cells, subsequently implanting human PBMCs and applying the mAb treatment to inhibit cancer cell growth in vivo. The experiment was designed as follows. Seven-eight week old SCID-male mice (Vital River Laboratories, China) were inoculated subcutaneously at right flank with $3 \times 10^6$ Hep3B/OS8-PD-L1 cells in 50% Matrigel (BD Biosciences, New Jersey, USA). Fifteen days after tumor inoculation, the mice bearing tumor size between 100-250 mm$^3$ were randomized and divided into three treatment groups. One hundred microliters of pooled PBMCs ($5 \times 10^5$) from 2 healthy donors were injected intratumorally. Three days post PBMC-implanting, anti-PD-1 antibodies (Hu317-IgG4mt2) and human IgG were administered via s.c. at a dose of 10 mg/kg, respectively. Antibody treatment was repeated once every 10 days for a total of 3 times. PBS was injected in a parallel group as negative control. Tumors were measured twice a week using a caliper starting on day 7. Tumor volumes were calculated using the following formula: $[D \times (d^2)]/2$, in which D represents the large diameter of the tumor, and d represents the small diameter. All animal studies were performed following Beigene Animal Care and Use Procedure.

Figure 11:
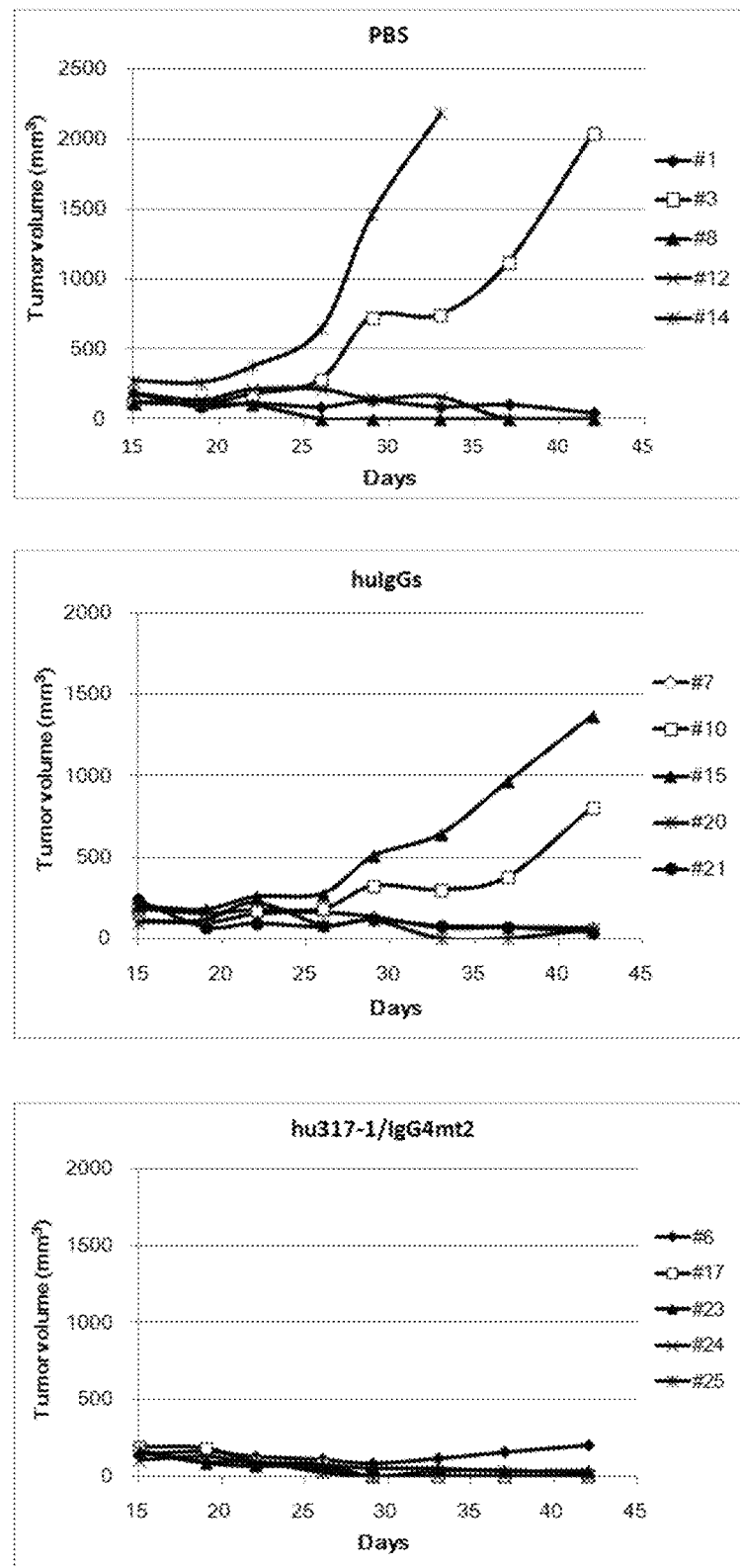
FIG. 11. Individual tumor growth curves in three treatment groups, vehicle (PBS), human IgGs (huIgGs) and anti-PD-1 mAb (hu317-1/IgG4mt2). Each curve represents a tumor growth path, the tumor-bearing mice coded by numbers indicated on the right of each panel. Hep3B/OS8/PD-L1 cells (established from hepatocellular carcinoma line Hep3B) were seeded at Day 1, PBMCs were implanted at Day 15 and three doses of hu317-1/IgG4mt2 were injected at Day 18, 28 and 38, respectively. Methods described in Example 12.

In the in vivo study, although 60% of tumors in the control groups were auto-regressed, the rest of in vivo experiment is still quite informative, which were presented in FIG. 11. In the control groups, either vehicle-treated or human IgG (huIgG)-treated group, each has 40% tumors (2 of 5 mice) outgrowing larger than the baseline at starting point. The two tumors in PBS-treated group grew much larger (above 2,000 mm$^3$, one tumor-bearing mouse was terminated earlier due to passing tumor size limit by protocol). The two tumors in huIgG-treated group grew to the size of 800 and 1,370 mm3, significantly above the average baseline of 164 mm$^3$ though smaller than the PBS-treated tumors. On the other hand, in the anti-PD-1 mAb (hu317-1/IgG4mt2)-treated group, tumors were either completely regressed or close to baseline size (one tumor=200 mm$^3$, which grew back slowly after regressed to 50% of baseline at two weeks from PBMC implanting). The results indicated that the anti-PD-1 mAb described above can activate human immune cells inhibiting tumor cells growth in the mouse in vivo cancer model, which is consistent to the in vitro experimental results described above.

What is claimed is:

1. An antibody antigen binding domain which specifically binds human PD-1, and comprises complementarity determining region (CDR) 1, CDR2 and CDR3, in a combination selected from (a)-(r) as follows, wherein the antibody (Ab), heavy chain (HC) or light chain (LC) and CDR nomenclature system (Kabat, IMGT or composite) from which the CDR combinations derive are shown in the first column, and residues in bold text are Kabat system, and residues underlined are IMGT system:

| Ab, Chain | | System | CDR1 |
|---|---|---|---|
| mu317 HC | (a) | Kabat | GFSLTSYGVH<br>SEQ ID NO: 11, res. 6-10 |
| | (b) | IMGT | SEQ ID NO: 11, res. 1-8 |
| | (c) | Comp. | SEQ ID NO: 11 |
| mu317 LC | (d) | Kabat | KASQSVSNDVA<br>SEQ ID NO: 14- |
| | (e) | IMGT | SEQ ID NO: 14, res. 4-9 |
| | (f) | Comp. | SEQ ID NO: 14 |
| 317-4B6 HC | (g) | Kabat | GFSLTSYGVH<br>SEQ ID NO: 11, res. 6-10 |
| | (h) | IMGT | SEQ ID NO: 11, res. 1-8 |
| | (i) | Comp. | SEQ ID NO: 11 |
| 317-4B6 LC | (j) | Kabat | KSSESVSNDVA<br>SEQ ID NO: 34 |
| | (k) | IMGT | SEQ ID NO: 34, res. 4-9 |
| | (l) | Comp. | SEQ ID NO: 34 |
| 317-1H HC | (m) | Kabat | GFSLTSYGVH<br>SEQ ID NO: 11, res. 6-10 |
| | (n) | IMGT | SEQ ID NO: 11, res. 1-8 |
| | (o) | Comp. | SEQ ID NO: 11 |
| 317-4B2 HC | (p) | Kabat | GFSLTSYGVH<br>SEQ ID NO: 11, res. 6-10 |
| | (q) | IMGT | SEQ ID NO: 11, res. 1-8 |
| | (r) | Comp. | SEQ ID NO: 11 |

| Ab, Chain | | System | CDR2 |
|---|---|---|---|
| mu317 HC | (a) | Kabat | VIWAGGSTNYNSALMS<br>SEQ ID NO: 12 |
| | (b) | IMGT | SEQ ID NO: 12, res. 2-8 |
| | (c) | Comp. | SEQ ID NO: 12 |
| mu317 LC | (d) | Kabat | YAFHRFT<br>SEQ ID NO: 15 |
| | (e) | IMGT | SEQ ID NO: 15, res. 1-3 |
| | (f) | Comp. | SEQ ID NO: 15 |
| 317-4B6 HC | (g) | Kabat | VIYADGSTNYNPSLKS<br>SEQ ID NO: 32 |
| | (h) | IMGT | SEQ ID NO: 32, res. 2-8 |
| | (i) | Comp. | SEQ ID NO: 32 |
| 317-4B6 LC | (j) | Kabat | YAFHRFT<br>SEQ ID NO: 15 |
| | (k) | IMGT | SEQ ID NO: 15, res. 1-3 |
| | (l) | Comp. | SEQ ID NO: 15 |

-continued

| | | | |
|---|---|---|---|
| 317-1H HC | (m) | Kabat | VIWAGGSTNYNPSLKS SEQ ID NO: 59 |
| | (n) | IMGT | SEQ ID NO: 59, res. 2-8 |
| | (o) | Comp. | SEQ ID NO: 59 |
| 317-4B2 HC | (p) | Kabat | VIYAGGSTNYNPSLKS SEQ ID NO: 60 |
| | (q) | IMGT | SEQ ID NO: 60, res.2-8 |
| | (r) | Comp. | SEQ ID NO: 60 |

| Ab, Chain | | System | CDR3 |
|---|---|---|---|
| mu317 HC | (a) | Kabat | ARAYGNYWYIDV SEQ ID NO: 13, res. 3-12 |
| | (b) | IMGT | SEQ ID NO: 13 |
| | (c) | Comp. | SEQ ID NO: 13 |
| mu317 LC | (d) | Kabat | HQAYSSPYT SEQ ID NO: 16 |
| | (e) | IMGT | SEQ ID NO: 16 |
| | (f) | Comp. | SEQ ID NO: 16 |

-continued

| | | | |
|---|---|---|---|
| 317-4B6 HC | (g) | Kabat | ARAYGNYWYIDV SEQ ID NO: 13, res. 3-12 |
| | (h) | IMGT | SEQ ID NO: 13 |
| | (i) | Comp. | SEQ ID NO: 13 |
| 317-4B6 LC | (j) | Kabat | HQAYSSPYT SEQ ID NO: 16 |
| | (k) | IMGT | SEQ ID NO: 16 |
| | (l) | Comp. | SEQ ID NO: 16 |
| 317-1H HC | (m) | Kabat | ARAYGNYWYIDV SEQ ID NO: 13, res. 3-12 |
| | (n) | IMGT | SEQ ID NO: 13 |
| | (o) | Comp. | SEQ ID NO: 13 |
| 317-4B2 HC | (p) | Kabat | ARAYGNYWYIDV SEQ ID NO: 13, res. 3-12 |
| | (q) | IMGT | SEQ ID NO: 13 |
| | (r) | Comp. | SEQ ID NO: 13. |

2. An antibody antigen binding domain according to claim 1 comprising CDR1, CDR2 and CDR3, in combination as follows:

| Ab, Chain | System | CDR1 | CDR2 | CDR3 |
|---|---|---|---|---|
| mu317 HC | (a) Kabat | SEQ ID NO: 11, res. 6-10 | SEQ ID NO: 12 | SEQ ID NO: 13, res. 3-12. |

3. An antibody antigen binding domain according to claim 1 comprising CDR1, CDR2 and CDR3, in combination as follows:

| Ab, Chain | System | CDR1 | CDR2 | CDR3 |
|---|---|---|---|---|
| mu317 HC | (b) IMGT | SEQ ID NO: 11, res. 1-8 | SEQ ID NO: 12, res. 2-8 | SEQ ID NO: 13. |

4. An antibody antigen binding domain according to claim 1 comprising CDR1, CDR2 and CDR3, in combination as follows:

| Ab, Chain | System | CDR1 | CDR2 | CDR3 |
|---|---|---|---|---|
| mu317 HC | (c) Comp. | SEQ ID NO: 11 | SEQ ID NO: 12 | SEQ ID NO: 13. |

5. An antibody antigen binding domain according to claim 1 comprising CDR1, CDR2 and CDR3, in combination as follows:

| Ab, Chain | System | CDR1 | CDR2 | CDR3 |
|---|---|---|---|---|
| mu317 LC | (d) Kabat | SEQ ID NO: 14 | SEQ ID NO: 15 | SEQ ID NO: 16. |

6. An antibody antigen binding domain according to claim 1 comprising CDR1, CDR2 and CDR3, in combination as follows:

| Ab, Chain | System | CDR1 | CDR2 | CDR3 |
|---|---|---|---|---|
| mu317 LC (e) | IMGT | SEQ ID NO: 14, res. 4-9 | SEQ ID NO: 15, res. 1-3 | SEQ ID NO: 16. |

7. An antibody antigen binding domain according to claim 1 comprising CDR1, CDR2 and CDR3, in combination as follows:

| Ab, Chain | System | CDR1 | CDR2 | CDR3 |
|---|---|---|---|---|
| mu317 LC (f) | Comp. | SEQ ID NO: 14 | SEQ ID NO: 15 | SEQ ID NO: 16. |

8. An antibody antigen binding domain according to claim 1 comprising CDR1, CDR2 and CDR3, in combination as follows:

| Ab, Chain | System | CDR1 | CDR2 | CDR3 |
|---|---|---|---|---|
| 317-4B6 HC (g) | Kabat | SEQ ID NO: 11, res. 6-10 | SEQ ID NO: 32 | SEQ ID NO: 13, res. 3-12. |

9. An antibody antigen binding domain according to claim 1 comprising CDR1, CDR2 and CDR3, in combination as follows:

| Ab, Chain | System | CDR1 | CDR2 | CDR3 |
|---|---|---|---|---|
| 317-4B6 HC (h) | IMGT | SEQ ID NO: 11, res. 1-8 | SEQ ID NO: 32 res.2-8 | SEQ ID NO: 13. |

10. An antibody antigen binding domain according to claim 1 comprising CDR1, CDR2 and CDR3, in combination as follows:

| Ab, Chain | System | CDR1 | CDR2 | CDR3 |
|---|---|---|---|---|
| 317-4B6 HC (i) | Comp. | SEQ ID NO: 11 | SEQ ID NO: 32 | SEQ ID NO: 13. |

11. An antibody antigen binding domain according to claim 1 comprising CDR1, CDR2 and CDR3, in combination as follows:

| Ab, Chain | System | CDR1 | CDR2 | CDR3 |
|---|---|---|---|---|
| 317-4B6 LC (j) | Kabat | SEQ ID NO: 34 | SEQ ID NO: 15 | SEQ ID NO: 16. |

12. An antibody antigen binding domain according to claim 1 comprising CDR1, CDR2 and CDR3, in combination as follows:

| Ab, Chain | System | CDR1 | CDR2 | CDR3 |
|---|---|---|---|---|
| 317-4B6 LC (k) | IMGT | SEQ ID NO: 34, res. 4-9 | SEQ ID NO: 15, res.1-3 | SEQ ID NO: 16. |

13. An antibody antigen binding domain according to claim 1 comprising CDR1, CDR2 and CDR3, in combination as follows:

| Ab, Chain | System | CDR1 | CDR2 | CDR3 |
|---|---|---|---|---|
| 317-4B6 LC (l) | Comp. | SEQ ID NO: 34 | SEQ ID NO: 15 | SEQ ID NO: 16. |

14. An antibody antigen binding domain according to claim 1 comprising CDR1, CDR2 and CDR3, in combination as follows:

| Ab, Chain | System | CDR1 | CDR2 | CDR3 |
|---|---|---|---|---|
| 317-1H HC (m) | Kabat | SEQ ID NO: 11, res. 6-10 | SEQ ID NO: 59 | SEQ ID NO: 13, res. 3-12. |

15. An antibody antigen binding domain according to claim 1 comprising CDR1, CDR2 and CDR3, in combination as follows:

| Ab, Chain | System | CDR1 | CDR2 | CDR3 |
|---|---|---|---|---|
| 317-1H HC (n) | IMGT | SEQ ID NO: 11, res. 1-8 | SEQ ID NO: 59, res. 2-8 | SEQ ID NO: 13. |

16. An antibody antigen binding domain according to claim 1 comprising CDR1, CDR2 and CDR3, in combination as follows:

| Ab, Chain | System | CDR1 | CDR2 | CDR3 |
|---|---|---|---|---|
| 317-1H HC (o) | Comp. | SEQ ID NO: 11 | SEQ ID NO: 59 | SEQ ID NO: 13. |

17. An antibody antigen binding domain according to claim 1 comprising CDR1, CDR2 and CDR3, in combination as follows:

| Ab, Chain | System | CDR1 | CDR2 | CDR3 |
|---|---|---|---|---|
| 317-4B2 HC(p) | Kabat | SEQ ID NO: 11, res. 6-10 | SEQ ID NO: 60 | SEQ ID NO: 13, res. 3-12. |

18. An antibody antigen binding domain according to claim 1 comprising CDR1, CDR2 and CDR3, in combination as follows:

| Ab, Chain | System | CDR1 | CDR2 | CDR3 |
|---|---|---|---|---|
| 317-4B2 HC(q) | IMGT | SEQ ID NO: 11, res. 1-8 | SEQ ID NO: 60, res.2-8 | SEQ ID NO: 13. |

19. An antibody antigen binding domain according to claim 1 comprising CDR1, CDR2 and CDR3, in combination as follows:

| Ab, Chain | System | CDR1 | CDR2 | CDR3 |
|---|---|---|---|---|
| 317-4B2 HC(r) | Comp. | SEQ ID NO: 11 | SEQ ID NO: 60 | SEQ ID NO: 13. |

20. An antibody antigen binding domain according to claim 1 comprising a heavy chain variable region (Vh) comprising a CDR1, CDR2 and CDR3 combination selected from (g), (h) and (i), and a light chain variable region (Vk) comprising a CDR1, CDR2 and CDR3 combination selected from (j), (k) and (l).

21. An antibody antigen binding domain according to claim 1 comprising CDR1, CDR2 and CDR3, in a combination select from (c), (f), (i), (l), (o) and (r), as follows:

| Ab, Chain | | CDR1 | CDR2 | CDR3 |
|---|---|---|---|---|
| (c) mu317 HC | | SEQ ID NO: 11 | SEQ ID NO: 12 | SEQ ID NO: 13 |
| (f) mu317 LC | | SEQ ID NO: 14 | SEQ ID NO: 15 | SEQ ID NO: 16 |
| (i) 317-4B6 HC | | SEQ ID NO: 11 | SEQ ID NO: 32 | SEQ ID NO: 13 |
| (l) 317-4B6 LC | | SEQ ID NO: 34 | SEQ ID NO: 15 | SEQ ID NO: 16 |
| (o) 317-1H HC | | SEQ ID NO: 11 | SEQ ID NO: 59 | SEQ ID NO: 13 |
| (r) 317-4B2 HC | | SEQ ID NO: 11 | SEQ ID NO: 60 | SEQ ID NO: 13. |

22. An antibody antigen binding domain according to claim 1 comprising a heavy chain variable region (Vh) or a light chain variable region (Vk), comprising a sequence selected from the group consisting of:

| | |
|---|---|
| mu317 H | (SEQ ID NOS: 4); |
| mu317 L | (SEQ ID NOS: 6); |
| 317-4B6 H | (SEQ ID NOS: 24); |
| 317-4B6 L | (SEQ ID NOS: 26); |
| 317-4B2 H | (SEQ ID NOS: 43); |
| 317-4B2 L | (SEQ ID NOS: 44); |
| 317-4B5 H | (SEQ ID NOS: 45); |
| 317-4B5 L | (SEQ ID NOS: 46); |
| 317-1 H | (SEQ ID NOS: 48); |
| 317-1 L | (SEQ ID NOS: 50); |
| 317-3A1 L | (SEQ ID NOS: 64); |
| 317-3C1 L | (SEQ ID NOS: 65); |
| 317-3E1 L | (SEQ ID NOS: 66); |
| 317-3F1 L | (SEQ ID NOS: 67); |
| 317-3G1 L | (SEQ ID NOS: 68); |
| 317-3H1 L | (SEQ ID NOS: 69); |
| 317-3I1 L | (SEQ ID NOS: 70); |
| 317-4B1 L | (SEQ ID NOS: 71); |
| 317-4B3 L | (SEQ ID NOS: 72); |
| 317-4B4 L | (SEQ ID NOS: 73); or |
| 317-4A2 L | (SEQ ID NOS: 74). |

23. An antibody antigen binding domain according to claim 1 comprising a heavy chain variable region (Vh) and a light chain variable region (Vk) comprising a sequence selected from the group consisting of:

| | |
|---|---|
| mu317 | (SEQ ID NOS: 4 and 6); |
| 317-4B6 | (SEQ ID NOS: 24 and 26) |
| 317-4B2 | (SEQ ID NOS: 43 and 44); |
| 317-4B5 | (SEQ ID NOS: 45 and 46); |
| 317-1 | (SEQ ID NOS: 48 and 50); |
| 317-3A1 | (SEQ ID NOS: 64 and 26); |
| 317-3C1 | (SEQ ID NOS: 65 and 26); |
| 317-3E1 | (SEQ ID NOS: 66 and 26); |
| 317-3F1 | (SEQ ID NOS: 67 and 26); |
| 317-3G1 | (SEQ ID NOS: 68 and 26); |
| 317-3HI | (SEQ ID NOS: 69 and 26); |
| 317-3I1 | (SEQ ID NOS: 70 and 26); |
| 317-4B1 | (SEQ ID NOS: 71 and 26); |
| 317-4B3 | (SEQ ID NOS: 72 and 26); |
| 317-4B4 | (SEQ ID NOS: 73 and 26); or |
| 317-4A2 | (SEQ ID NOS: 74 and 26). |

24. An antibody antigen binding domain according to claim 1 comprising a heavy chain variable region (Vh) or a light chain variable region (Vk) comprising:
317-4B6 H (SEQ ID NOS:24) or 317-4B6 L (SEQ NOS: 26).

25. An antibody antigen binding domain according to claim 1 comprising a heavy chain variable region (Vh) and a light chain variable region (Vk) comprising:
317-4136 H (SEQ ID NOS:24) and 317-4B6 L (SEQ NOS: 26).

26. An antibody antigen binding domain according to claim 1 which specifically binds PD1 residues: K45 and I93 (equivalent to K58 and I106 in SEQ ID NO 2).

27. An antibody antigen binding domain according to claim 1 which induces IL-2 release in PD-1-transformed cells co-cultured with OS8/PD-L1 or OS8/PD-L2 cotransformed cells, and/or inhibits of IL-2 secretion in P3Z-transformed cells co-cultured with PD-L1- or PD-L2-transformed cells, wherein:
  OS8 (SEQ ID NO:89) is a membrane-anchored chimeric Ab constructed by fusing the single chain variable fragment (scFv) of an anti-human CD3 mAb OKT3 to the C-terminal domain (113-220) of mouse CD8α; and
  P3Z (SEQ ID NO:90) is a chimeric PD-1 receptor, constructed by fusing the extracellular and transmembrane domains of human PD-1 to the cytoplasmic domain of human CD3ζ chain.

28. A monoclonal IgG antibody comprising an antibody antigen binding domain according to claim 1.

29. A monoclonal IgG antibody comprising an antibody antigen binding domain according to claim 20.

30. A monoclonal IgG antibody comprising an antibody antigen binding domain according to claim 25.

31. A monoclonal IgG antibody comprising an antibody antigen binding domain according to claim 1 and an IgG4 heavy chain effector or constant domain comprising any of SEQ ID NO:83-88.

32. An IgG antibody comprising an antibody antigen binding domain according to claim 1 and an IgG4 heavy chain effector or constant domain comprising SEQ ID NO 87 or 88.

33. An IgG antibody comprising an antibody antigen binding domain according to claim 20 and an IgG4 heavy chain effector or constant domain comprising SEQ ID NO 87 or 88.

34. An IgG antibody comprising an antibody antigen binding domain according to claim 25 and an IgG4 heavy chain effector or constant domain comprising SEQ ID NO 87 or 88.

35. A method of using an antibody antigen binding domain according to claim 1 comprising the step of administering the domain to a person determined to have cancer or a viral infection or to otherwise be in need of PD-I antagonism.

* * * * *

UNITED STATES PATENT AND TRADEMARK OFFICE
CERTIFICATE OF CORRECTION

| | |
|---|---|
| PATENT NO. | : 8,735,553 B1 |
| APPLICATION NO. | : 14/076214 |
| DATED | : May 27, 2014 |
| INVENTOR(S) | : Kang Li et al. |

It is certified that error appears in the above-identified patent and that said Letters Patent is hereby corrected as shown below:

In the Claims

In Claim 25, Column 106, Line 47, please replace:
"317-4136 H (SEQ ID NOS:24) and 317-4B6 L (SEQ NOS:"
With:
-- 317-4B6 H (SEQ ID NOS:24) and 317-4B6 L (SEQ ID NOS: --.

Signed and Sealed this
Ninth Day of August, 2022

Katherine Kelly Vidal
*Director of the United States Patent and Trademark Office*